US009770476B2

(12) United States Patent
Chabot

(10) Patent No.: US 9,770,476 B2
(45) Date of Patent: Sep. 26, 2017

(54) FUNCTIONAL FOODS AND BEVERAGES WITH SYNERGISTIC PROPERTIES TO PROMOTE HOMEOSTASIS

(75) Inventor: Sophie Chabot, St-Jean-Port-Joli (CA)

(73) Assignee: Justbio Inc., La Pocatiere (CA)

( * ) Notice: Subject to any disclaimer, the term of this patent is extended or adjusted under 35 U.S.C. 154(b) by 988 days.

(21) Appl. No.: 13/983,197

(22) PCT Filed: Feb. 1, 2012

(86) PCT No.: PCT/CA2012/000090
§ 371 (c)(1),
(2), (4) Date: Aug. 1, 2013

(87) PCT Pub. No.: WO2012/103637
PCT Pub. Date: Aug. 9, 2012

(65) Prior Publication Data
US 2013/0310449 A1 Nov. 21, 2013

Related U.S. Application Data

(60) Provisional application No. 61/438,747, filed on Feb. 2, 2011, provisional application No. 61/472,298, filed on Apr. 6, 2011.

(51) Int. Cl.
| A61K 36/28 | (2006.01) |
| A61K 36/53 | (2006.01) |
| A61K 36/539 | (2006.01) |
| A61K 36/73 | (2006.01) |
| A61K 36/734 | (2006.01) |
| G01N 33/50 | (2006.01) |
| A23L 2/39 | (2006.01) |
| A23L 2/52 | (2006.01) |
| A61K 31/05 | (2006.01) |
| A61K 31/352 | (2006.01) |
| A23L 33/10 | (2016.01) |

(52) U.S. Cl.
CPC ............... *A61K 36/28* (2013.01); *A23L 2/39* (2013.01); *A23L 2/52* (2013.01); *A23L 33/10* (2016.08); *A61K 31/05* (2013.01); *A61K 31/352* (2013.01); *A61K 36/53* (2013.01); *A61K 36/539* (2013.01); *A61K 36/73* (2013.01); *A61K 36/734* (2013.01); *G01N 33/502* (2013.01); *G01N 2500/10* (2013.01); *G01N 2800/7009* (2013.01)

(58) Field of Classification Search
None
See application file for complete search history.

(56) References Cited

U.S. PATENT DOCUMENTS

| 6,299,925 B1 | 10/2001 | Xiong et al. | |
| 2005/0048143 A1 | 3/2005 | McAnalley et al. | |
| 2005/0175720 A1* | 8/2005 | McKenzie | A61K 35/60 424/732 |
| 2005/0266018 A1* | 12/2005 | Boreyko | A61K 33/04 424/195.17 |
| 2006/0024385 A1* | 2/2006 | Pedersen | A23L 33/195 424/725 |
| 2008/0166313 A1* | 7/2008 | Jochim | A61K 8/97 424/74 |
| 2010/0021533 A1 | 1/2010 | Mazed et al. | |

FOREIGN PATENT DOCUMENTS

| CN | 101455363 A | 6/2009 |
| WO | 2010/027344 A1 | 3/2010 |

OTHER PUBLICATIONS

Candan (J. of Ethnopharm. (2003), vol. 87, pp. 215-220).*
Theriault (Food Chem. (2006), vol. 98, pp. 490-501).*
Venskutonis (Fitoterapia (2007), vol. 78, pp. 162-165).*
Wang (J. Agric. Food Chem. (2000), vol. 48, pp. 140-146).*
Legault (Journal of Medicinal Food (2010), vol. 13, No. 2, pp. 460-468).*
Blanchet, Julie et al., "Resveratrol, a red wine polyphenol, protects dopaminergic neurons in MPTP-treated mice," Progress in Neuro-Psychopharmacology & Biological Psychiatry 32 (2008) 1243-1250.
Bu, So Young et al., "Dried Plum Polyphenols Inhibit Osteoclastogenesis by Downregulating NFATc1 and Inflammatory Mediators," Calcif Tissue Int (2008) 82:475-488.
Dulloo, Abdul G. et al., "Efficacy of a green tea extract nigh in catechin polyphenols and caffeine in increasing 24-h energy expenditure and fat oxidation in humans," Am J Clin Nutr 1999; 70:1040-5.
Fujihara, Takashi et al., High-Molecular-Weight Polyphenols from Oolong Tea and Black Tea: Purification, Some Properties, and Role in Increasing Mitochondrial Membrane Potential, Biosci. Biotechnol. Biochem., 71 (3), 711-719, 2007.
Ghanta, Srijani et al., "Oxidative DNA Damage Preventive Activity and Antioxidant Potential of *Stevia rebaudiana* (Bertoni) Bertoni, a Natural Sweetener," J. Agric. Food Chem. 2007, 55, pp. 10962-10967.
Gong, Jianfeng et al., "Epithelial-specific blockade of MyD88-dependent pathway causes spontaneous small intestinal inflammation," Clinical Immunology (2010) 136, pp. 245-256.
Gribar, Steven C. et al., "The role of epithelial Toll-like receptor signaling in the pathogenesis of intestinal inflammation," Journal of Leukocyte Biology, vol. 83, Mar. 2008, pp. 493-498.
Hermann, F. et al., "Dark chocolate improves endothelial and platelet function," Scientific Letter, Heart 2006;92:119-120.
Hirao, Kouji et al., "Tea catechins reduce inflammatory reactions via mitogen-activated protein kinase pathways in toll-like receptor 2 ligand-stimulated dental pulp cells," Life Sciences 86 (2010) 654-660.
Jacobs, David R. et al., "Food synergy: an operational concept for understanding nutrition," Am J Clin Nutr 2009; 89 (suppl):1543S-8S.
Kanzler, H. et al., "Therapeutic targeting of innate immunity with Toll-like receptor agonists and antagonists," Nat Med. May 2007; 13(5):552-9 (Abstract).

(Continued)

*Primary Examiner* — Susan Hoffman

(74) *Attorney, Agent, or Firm* — Eversheds Sutherland (US) LLP

(57) ABSTRACT

The present invention provides compositions having synergistic antioxidant properties in the modulation of Toll-like receptor signaling for the promotion of homeostasis, immunity, energy conservation, protection of neural cells and anti-inflammatory responses, said compositions comprising plant and/or fruit extracts and a natural sweetener with high oxidation potential as defined by ORAC value.

7 Claims, 47 Drawing Sheets

(56) References Cited

OTHER PUBLICATIONS

Leonarduzzi, G. et al., "Targeting tissue oxidative damage by means of cell signalling modulators: the antioxidant concept revisited," Pharmacol Ther. Nov. 2010; 128(2):336-74 (Abstract).

Manach, Claudine et al., "Polyphenols and prevention of cardiovascular diseases," Current Opinion in Lipidology 2005, 16:77-84.

McDougall, Gordon J. et al., "The inhibitory effects of berry polyphenols on digestive enzymes," BioFactors 23 (2005) 189-195.

Mélanie, Gauthier et al., Full Length Research Paper, "Polyphenol-rich beverages promote a sustainable and renewable generation of energy and prevent neurotoxicity," academicJournals, International Journal of Nutrition and Metabolism, vol. 5(4), Apr. 2013 (ISSN 2141-2499), pp. xxx-xxx.

Messina, Mark, et al., "Reductionism and the arrowing nutrition perspective: Time for reevaluation and emphasis on food synergy," Journal of the American Dietetic Association, Dec. 2001, vol. 101, No. 12, pp. 1416-1419.

Ohno, Hideki et al., "The Supplementation of Oligonol, the New Lychee Fruit-derived Polyphenol Converting into a Low-molecular form, Has a Positive Effect on Fatigue during Regular Track-and-field Training in Young Athletes," Adv. Exerc. Sports Physiol., vol. 13, No. 4, pp. 93-99, 2008.

PCT International Preliminary Report on Patentability for PCT/CA2012/000090 dated Jun. 3, 2013.

PCT International Search Report for PCT/CA2012/000090 dated May 29, 2012.

PCT Written Opinion for PCT/CA2012/000090 dated May 29, 2012.

Shibolet, Oren et al., "TLRs in the Gut. IV. Negative regulation of Toll-like receptors and intestinal homeostasis: addition by subtraction," Am J Physiol Gastrointest Liver Physiol 292: G1469-G1473, 2007.

Singh, Manjeet et al., "Challenges for Research on Polyphenols from Foods in Alzheimer's Disease: Bioavailability, Metabolism, and Cellular and Molecular Mechanisms," Journal Agricultural and Food Chemistry, 2008, vol. 56, pp. 4855-4873.

Ulrich-Merzenich, Gudrun et al., "Synergy research: Vitamins and secondary plant components in the maintenance of the redox-homeostasis and in cell signaling," ScienceDirect, Phytomedicine 16 (2009) 2-16.

Wells, Jerry M. et al., "The role of innate signaling in the homeostasis of tolerance and immunity in the intestine," International Journal of Medical Microbiology 300 (2010) pp. 41-48.

Youn, Hyung S. et al., "Suppression of MyD88- and TRIF-dependent signaling pathways of toll-like receptor by (−)- epigallocatechin-3-gallate, a polyphenol component of green tea," Biochemical Pharmacology 72 (2006) 850-859.

Burdulis, et al., "Comparative study of anthocyanin composition, antimicrobial and antioxidant activity in bilberry (*Vaccinium myrtillus* I.) and blueberry (*Vaccinium corymbosum* I.) fruits," Acta Poloniae Pharmaceutica—Drug Research, vol. 65, No. 4, pp. 399-408, 2009.

Liu, et al., "Extraction optimization, purificatiom and antioxidant activity of procyanidins from hawthorn (*C. pinnatifida* Bge. var. major) fruits," Food Chemistry 119 1656-1662, (2010).

Moller, et al., "Dietary antioxidants and beneficial effect on oxidatively damaged DNA," Free Radical Biology & Medicine 41 (2006) 388-415.

Phillips, et al., "Total antioxidant content of alternatives to refined sugar," Journal of the American Dietetic Association, 2009; 109:64-71.

Ratnam, et al., "Role of antioxidants in prophylaxis and therapy: A pharmaceutical perspective," Journal of Controlled Release 113 (2006) 189-207.

Rifkin, et al., "Toll-like receptors, endogenous ligands, and systemic autoimmune disease," Immunological Reviews, 2005, vol. 204:27-42.

Scalbert, et al., Polyphenols: antioxidants and beyond 1-3, The American Journal of Clinical Nutrition, 2005; 81 (suppl):215S-217S.

Shang, et al., "The genus scutellaria an ethnopharmacological and phytochemical review," Journal of Ethnopharmacology 128 (2010) 279-313.

Sokol-Letowska, et al., "Antioxidant activity of the phenolic compounds of hawthorn, pine and skullcap," Food Chemistry 103 (2007) 853-859.

Valentova, et al., "Biosafety, antioxidant status, and metabolites in urine after consumption of dried cranberry juice in healthy women: a pilot double-blind placebo-controlled trial," Journal of Agricultural and Food Chemistry, 2007, 55, 3217-3224.

Vattem, et al., "Cranberry phenolics-mediated antioxidant enzyme response in oxidatively stressed porcine muscle," Process Biochemistry 40 (2005) 2225-2238.

\* cited by examiner

FIGURE 45

SUMMARY of RESULTS

| BEVERAGE | ANTIOXYDANT (anti-ROS) 1=low antioxydant 10= high antioxydant | Energy LIFT | Energy DEPLETION | Energy CONSERVATION | Mucosal TLR2 regulation | NEURO-protection dopaminergic system | CALMING effect | Mucosal TOXICITY (Cell death) |
|---|---|---|---|---|---|---|---|---|
| Formulation 1 | 10 time and dose-dependent | yes | no | yes | yes | yes | yes | no |
| Formulation 2 | 7 time and dose-dependent | yes | no | yes | yes | yes | no | no |
| Competitor 8 | 2 | no | no | yes | no | no | no | no |
| Competitor 9 | 1 | no | yes | no | no | no | no | yes |
| Competitor 3 | 8 Not time and dose-dependent | no | no | yes | yes | yes | no | no |
| Competitor 1 | 5 | yes | no | yes | slight | no | no | no |
| Competitor 2 | 1 | no | no | yes | no | no | no | no |

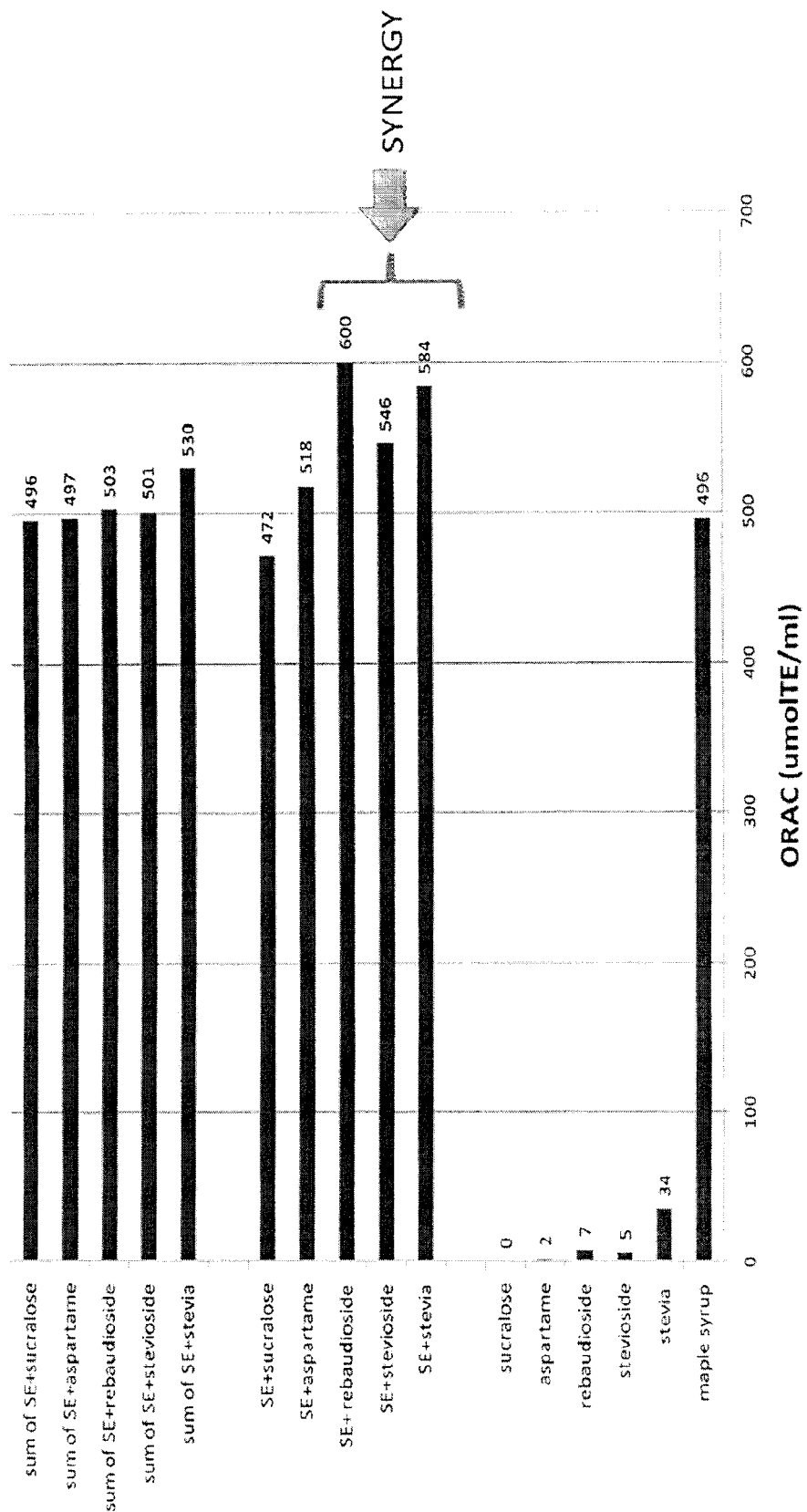

FUNCTIONAL FOODS AND BEVERAGES WITH SYNERGISTIC PROPERTIES TO PROMOTE HOMEOSTASIS

CROSS-REFERENCE TO RELATED APPLICATIONS

This application is a §371 US national stage application of International Application Number PCT/CA2012/000090 filed Feb. 1, 2012, which claims priority from U.S. provisional applications No. 61/438,747 filed Feb. 2, 2011 and 61/472,298 filed Apr. 6, 2011, the contents of which are hereby incorporated by reference in their entireties.

FIELD OF THE INVENTION

The present invention relates to the fields of functional foods, functional beverages and sweeteners useful for the maintenance of homeostasis and energy levels in mammals. More specifically, the present invention relates to functional foods and beverages that can contribute to the maintenance of health and wellness through mechanisms that involve interactions between epithelial cells of the mucosa with both the immune system and the dopaminergic nervous system of the submucosa as well as ATP and ROS generated from cellular responses. Such foods and beverages contribute to reducing the risks of chronic diseases such as cancers, cardiovascular diseases, neurodegenerative diseases, chronic inflammatory diseases, autoimmune diseases and diabetes.

BACKGROUND OF THE INVENTION

Adaptation

Evolution is driven by a process called adaptation whereby an organism becomes better able to live in its habitat. Adaptedness is the state of being adapted, the degree to which an organism is able to live and reproduce in a given set of habitats. It is acknowledged that best adapted organisms will have the best chance of survival. Adaptedness is best reached through the body's ability to maintain a state of equilibrium, known as homeostasis, which involves the preservation of physiological functions such as body's temperature, respiratory rate, and blood chemistry, within tightly controlled limits.

Homeostasis

Homeostasis is defined as a balanced physiological state essential for adaptation. Homeostasis is a state in which everything within the cell is in equilibrium and functioning properly. Homeostasis conservation in human body depends on the delicate balance between cell's capacity to maintain metabolism and demand. In order to prevent diseases and other dysfunctions, tissues in our body accomplishes many metabolic reactions to maintain a constancy of environment for the vitality and well-being. At the cell level, to maintain equilibrium or homeostasis, the cell membranes must be in continuous interaction with both the internal (intracellular) environment and the external (extracellular) environment. When the homeostasis of any component is disturbed, the interaction permits automatic readjustment by giving rise to stimuli that result in restoration of metabolic process. The state of homeostasis requires a good transport of important nutrient for the cell to continue to function properly.

Mechanisms of Homeostasis

In General:

Homeostasis processes are involved in the regulation of gut/mucosal epithelial functions and integrity, glucose level/insulin resistance, energy levels, endocrine/stress hormones levels, oxidative stress (respiration), immune/inflammatory state, neurological functions and mitochondria functions. Molecular mechanisms regulating homeostasis involve, among others, TLR activation, calcium influx, ATP production, inflammatory cytokines production, neurotransmitter release, hormonal production, and reactive oxygen species (ROS) production.

Mitochondria-Driven Homeostasis:

Intake of oxygen and nutrients regulate the physiological responses of adaptation. These responses are carried out mainly by mitochondria of eukaryotic cells, also know as the cell's power producers. Through glycolysis, a process that converts glucose into pyruvate, the energy fuel adenosine triphosphate (ATP) is released. Pyruvate is then used by the mitochondria to generate more ATP, representing 90% of all ATP generated, and reactive oxygen species (ROS) through the reduction of the oxygen from the electron transport chain. ROS include the superoxide, oxygen singlet, hydrogen peroxide and hydroxyl. Intracellular ROS, the majority of which is derived from mitochondria (Finkel and Holbrook, 2000), can act as signaling molecules and play important roles in homeostasis (D'Autréaux and Toledano, 2007). However, excessive production of ROS can lead to a situation known as oxidative stress, resulting in a significant damage to cell structures, a process known to be involved in ageing (Finkel and Holbrook, 2000). Oxidative stress plays a role in the pathogenesis of diseases such as diabetes, atherosclerosis, chronic inflammations or cancer (Crimi et al., 2006). In addition to act as a power house, mitochondria also function as signaling platforms to regulate innate protective mechanisms (West et al, 2011). It is not known whether mitochondria activities, through ATP and ROS generation, also drive adaptation.

Toll-Like-Receptors and Homeostasis:

Toll-like receptors (TLRs) are evolutionary-conserved type I transmembrane proteins that act as key regulators of innate defense mechanisms essential to the protection and survival of the organism. Mucosal surfaces, exposed to food, represent critical physical and functional interfaces between the body's internal and external world. TLRs are abundantly expressed at mucosal surfaces, especially in the buccal cavity (Wang et al, 2009) and in villus and crypt intestinal epithelial cells at their apical poles (Didierlaurent at al, 2002; Ortega-Cava 2003). In the general intestinal mucosa, TLRs play a homeostatic role, maintaining the epithelial barrier and preventing responses to TLR agonists on luminal microorganisms (Backhed et al, 2005; Rakoff-Nahoum et al 2004; Abreu 2010). Indeed, deregulation of TLR signaling in the gut can result in chronic inflammatory and excessive and even destructive repair responses that may be associated with diseases like colon cancer and inflammatory bowel diseases (Abreu 2010, Cario 2010). Particularly, the role of mucosal TLR2 in homeostasis is important because it plays a role in gate keeping functions of intestinal epithelial cells (Chabot et al, 2006) and controls mucosal inflammation by regulating epithelial barrier function (Cario et al, 2007, 2008). Although there is evidence that TLR1/2/4 signaling induces mitochondrial ROS generation through TRAF6 and ECSIT interaction to augment macrophage bactericidal activity (West et al, 2011), it is not known whether TLRs also regulate mitochondria-driven homeostasis. A recent study of TLR evolution shows a clear signature of positive selection in their rates of substitution across primates, suggesting TLRs may also play a significant role in adaptation (Wlasiuk and Nachman, 2010)

Neurotransmission and Homeostasis:

Maintaining balanced levels of neurotransmitters contribute to homeostasis. Dopamine (DA) is the key neurotransmitter that regulates the reward, motivation and reinforcement center of the central nervous system (CNS), as well as the hypothalamic-pituitary-adrenal (HPA) axis, known to control stress responses. DA is involved in many motivational behaviors including rewarding, motivation, food intake, food reward, addiction and motor control. Striatum and nucleus accumbens (NAcc) are brain structures where DA is produced, and they are referred sites of control of food reward. It is well documented that DA production in striatum and NAcc is excessive following binge intake of sugar and fat. There is also modification in Ach and opioids systems such as those observed in drug abuse. Binge eating, associated to obesity, afflicting a large proportion of the American adult population, is also associated with depression, anxiety and substance abuse. Serotonin, the neurotransmitter that plays a role in depression and anxiety through the regulation of mood, can also affect dopamine release in the MLDS brain regions.

Active Ingredients

Adaptogens: The concept of "adaptogens" is thousands of years old, and was long considered an important feature of ancient medical systems in parts of Asia and in northern Europe. Although pharmacological evidence is still missing, herbalists claim that adaptogens derived from plants exert a normalizing effect on the body without any risk of creating an unbalanced state, by inducing healthy functions while decreasing unhealthy responses triggered by stress. For that reason, adaptogens are believed to increase resistance to stress, trauma, anxiety and fatigue. It is believed that many antioxidants are indeed adaptogenic. Studies demonstrated that some adaptogenic plants can modulate TLR activity. For example, it was recently shown that the polyphenol epigallocatechin-3-gallate isolated from green tea, have been shown to down regulate TLR4 signal transduction (Byun et al 2010). Also, it was shown that dioscorin, a glycoprotein from *Dioscorea alata*, is a novel TLR4 activator and induces macrophage activation via typical TLR4-signaling pathways (Fu et al 2006). Another study demonstrated that 9,10-Dihydro-2,5-dimethoxyphenanthrene-1,7-diol, a phenanthrene isolated from *Eulophia ochreata* of the Orchidaceae family, blocked TLR4-dependent NF-kappaB-regulated inflammatory cytokine production (Datla et al, 2010). It is not known whether plant adaptogens can affect mitochondrial activity through TLR modulation to promote homeostasis.

Antioxidants: Antioxidants are described as molecules capable of inhibiting the oxidation of other molecules. Oxidation is a chemical reaction that transfers electrons from a substance to an oxidizing agent that can produce free radicals, which are toxic byproducts of cell metabolism that can start chain reactions that damage cells. Antioxidants terminate these chain reactions by removing free radical intermediates, and inhibit other oxidation reactions. Antioxidants are often reducing agents such as thiols, ascorbic acid or polyphenols. Although oxidation reactions are crucial for life, they can also be damaging; hence, plants and animals maintain complex systems of multiple types of antioxidants, such as glutathione, vitamin C, and vitamin E as well as enzymes such as catalase, superoxide dismutase and various peroxidases. Low levels of antioxidants, or inhibition of the antioxidant enzymes, cause oxidative stress and may damage or kill cells. The human body naturally produces antioxidant molecules but this process is not totally effective and that effectiveness declines with age. The fundamental nutritional benefit of fruit and vegetables in the prevention of diseases—especially in the light of the current "anti-aging wave" has directed the attention of scientists and consumers to a variety of berry fruits and their constituents. Many berries have a long tradition in European and North American folk medicine. Based on these experiences and due to the growing interest the number of food supplements on the market containing fruit powders, juice concentrates or extracts of these fruits has increased considerably. Advertising for these products mainly focuses on the phenolic compounds, especially the anthocyanins and proanthocyanidins and their preventive effects. Most of the preparations are combinations, e.g. of extracts of different fruits with vitamins and trace elements, etc. which are labeled in a way which does not allow a comparison of the products (Krenn et al, 2007). Antioxidant-rich food include berries (blueberries, blackberries, raspberries, strawberries and cranberries), beans (small red, kidney, pinto and black beans), fruits (apples, avocados, cherries, pears, pineapple, oranges, plums, kiwi), vegetables (Artichoke, spinach, red cabbage, potatoes, broccoli), beverages (green tea, coffee, red wine, fruit juices), nuts (walnuts, pistachios, pecans, hazelnuts and almonds), many herbs and spices, grains, and dark chocolate. Diets deficient in antioxidants can accelerate cell death, mitochondrial decay contributing to the development of chronic diseases, and other dysfunction. Antioxidant deficiency increases oxidative stress, and consequently leads to mitochondrial dysfunction and age-associated diseases, including metabolic syndrome.

Polyphenols: Polyphenols occur ubiquitously in plant foods and structurally have variations in the C ring that characterizes the different types namely, flavonols, flavones, isoflavones, flavonones, flavanol and anthocyanins. Polyphenols are present in large amount of fruits and vegetables as secondary plants metabolites and have a significant impact in preventing many diseases in human (Heim, Tagliaferro, & Bobilya, 2002). Polyphenols are potential adaptogens. It is a widely distributed compound in plants and not only have proprieties associated with food quality such as color and aroma, but also may have potential health benefits, including reduction of cancer risk (Macheix, Fleuriet, & Billot, 1990). According to Thériault at al. (2005), maple syrup (*Acer saccharum*) contains antioxidant and antiradical activities due to the presence of phenolic compounds. Cranberry polyphenolics, like other dietary polyphenolics, may induce activation mitochondrial apoptosis pathway. This anticancer property lead to tumor cells to apoptosis. The possible effects of cranberry on expression of genes controlling steps in the mitochondrial apoptosis pathway are currently under investigation. The main groups of polyphenols with their individual compounds and food sources are summarized in *J. Agric. Food Chem*. Vol. 56, No. 13, 2008, in FIG. 1 at page 4858, which is incorporated herein by reference.

Anthocyanins: Anthocyanins are polyphenolic compounds that belongs to the flavonoid family. They are colored (blue-red) pigments abundant in many fruits, vegetables and flowers. They are known to have antioxidant activity (Zafra-Stone et al, 2007). It is easy to presume that anthocyanins are also potential adaptogens. They readily donate hydrogen to form relatively stable unpaired-electron structures, and chelate transition metals such as iron. In the context of the nervous system, anthocyanins have been shown to improve motor and cognitive functions in experimental animals, and to prevent ROS-mediated apoptotic death in neurons (Levites et al., 2002). When mitochondrial proteins integrity is threatened, this may contribute to neurodegenerative disorders along with other apoptogenic mitochondrial disorders. There is evidence that spoiled cytochrome c, a protein in the electron transport chain, can lead to these disorders, and increase oxidative stress, respiratory chain dysfunction, and apoptotic cell death. Moreover, dopamine oxidation in neurons can result in the production of ROS and increase oxidative stress, reduce cytochrome c properties, and, by interfering with normal cytochrome redox cycling, may contribute to dopaminergic neurodegeneration (Mazzio et al. 2004). Yao and Vieira (2007) show that anthocyanins from *Vaccinium* species are potent inhibitors of dopamine oxidative forms.

Antioxidants and Prevention of Diseases

Antioxidants are said to be extremely good for us in many ways, helping to prevent and keep under control some serious illnesses. Recent research has shown that antioxidants can help with human health and lifestyles in many ways. Enhancement of antioxidant defenses through dietary supplementation is a reasonable and practical approach to help the body fight off chronic diseases such as cancer, cardiovascular diseases, neurodegenerative diseases, chronic inflammatory diseases, and diabetes (Finkel and Holbrook, 2000). Antioxidants help prevent the physiopathology of these diseases which involves the excessive and chronic presence of inflammatory mediators, oxidative stress and cell death. Antioxidants also help slowing down the ageing process and the development of age-related diseases (Finkel and Holbrook, 2000).

The Invention

It has now been found that the combination of antioxidant extracts can mutually potentiate their antioxidant potential. Combinations of antioxidant sweeteners such as maple syrup and a herbal extract (plants and/or herbs) and/or a plant-product extract (fruits and/or vegetables) having antioxidant properties have never been studied. The present invention demonstrates the synergistic effect of these combinations on antioxidant capacity of functional foods or beverages formulations.

It has further been found that combinations of antioxidant-rich extracts possess synergistic effects to modulate mechanisms regulating homeostasis, thereby helping to sustain homeostasis.

It is found that antioxidant-rich formulations developed by Applicant regulate TLR2-dependent oxidative and energetic mitochondrial responses in oral mucosal cells to promote homeostasis, providing important scientific evidence for their role as regulators of adaptation.

SUMMARY OF THE INVENTION

In a first aspect, the invention relates to the potentiated antioxidant potential of a composition comprising the following ingredients: an antioxidant herbal extract, an antioxidant plant-product extract; and a natural sweetener having antioxidant properties. This combination creates synergy to potentiate the formulation's antioxidant potential.

Particularly, there is provided a composition having synergistic antioxidant properties, essentially consisting of an antioxidant sweetener, an antioxidant plant-product extract and an antioxidant herbal extract, and optionally, a natural flavor or aroma.

More particularly, there is provided a composition having synergistic antioxidant properties, consisting of: an antioxidant sweetener, an antioxidant plant-product extract and an antioxidant herbal extract; and a natural flavor or aroma.

This invention proposes that the composition of a natural sweetener such as maple syrup, honey, corn syrup, stevia (or a steviol glycosides such as, for example, Stevioside or Rebaudioside A) or agave with an antioxidant herbal extract and an antioxidant plant-product extract potentiates the antioxidant potential of the extracts to produce a potent antioxidant functional food product.

In a further aspect of the invention, there is provided a method for maintaining/promoting or recovering homeostasis in a mammal comprising the step of administering a composition as defined above. In particular, oral ingestion is favored as a mode of administration. There is also provided the use of the composition as defined above for the maintenance/promotion or recovery of homeostasis in a mammal. Particularly, the mammal is a human.

In a further aspect of the invention, there is provided a method for the maintenance of homeostasis in a mammal, the method comprising the steps of: ingesting a composition as defined above that is a TLR modulator. Particularly, TLR modulator acts on TLR-expressing cells to release MIP3alpha, in turn, to affect at least one process involving: dopamine; ATP; inflammatory cytokines such as IL-6 and IL-10; or reduce reactive oxygen species or cell death.

Still, more particularly, with respect to the above-mentioned aspects, the composition is a liquid or a solid, more particularly an ingestible solid or liquid, most particularly a solid food or a liquid food (i.e. beverage).

In a further aspect of the invention, there is provided a method for preventing inflammation in a mammal comprising the steps of: ingesting a composition as defined above. There is also provided a use of the composition as defined above to prevent inflammation.

In a further aspect of the invention, there is provided a method for protecting or maintaining mucosal immunity in a mammal comprising the steps of: ingesting a composition as defined above. There is also provided the use of the composition as defined above for the protection or maintenance of mucosal immunity in a mammal.

In a further aspect of the invention, there is provided a method for the conservation of ATP levels in a cell of a mammal comprising the steps of: ingesting a composition as defined above. There is also provided the use of the composition as defined above for the conservation of ATP reserves in a cell of a mammal.

In a further aspect of the invention, there is provided a method for blocking energy release from a cell of a mammal comprising the steps of: ingesting a composition as defined above. The is also provided the use of the composition as defined above for blocking energy release from a cell of a mammal.

In a further aspect of the invention, there is provided a method for raising energy levels in a cell of a mammal comprising the steps of: ingesting a composition as defined above. There is also provided the use of a composition as defined above for increasing the energy levels of a cell in a mammal.

In a further aspect of the invention, there is provided a method for protecting a neural cell in a mammal comprising the steps of: ingesting a composition as defined above. There is also provided the use of the composition as defined above for the protection of a neural cell in a mammal.

In a further aspect of the invention, there is provided a method for the identification of a food or a food ingredient useful for the maintenance of homeostasis in a mammal, the method comprising the steps of:

measuring the TLR activity of said food or food ingredient;

whereby said food or food ingredient is a TLR modulator when said TLR induces a release of one or more of: IL-10, IL-6, MIP3α, dopamine and ATP; or a decrease in cell death or reactive oxygen species (ROS).

In an further aspect of the invention, there is provided a transwell assay for the identification of a TLR2 modulator, the assay comprising:
  a) in a top well, incubating a layer of TLR-expressing cells with a test agent;
  b) in a bottom well in contact with said top chamber, incubating a layer of sub-epithelial cells sensitive to MIP3α;
  c) measuring the presence of IL-6 or IL-10; or identifying an increase in ATP; or measuring a decrease in ROS; or a decrease in cell-death from cells in said bottom well;
wherein the presence of one of said response from step c) is indicative that said test agent is a potential TLR2 modulator.

In a further aspect of the invention, there is provided a method for the identification of a synergistic antioxidant composition, the method comprising the steps of:
  measuring the antioxidant potential of each component individually;
  measuring the antioxidant potential of the components when combined; and
  comparing the antioxidant potential of the combination versus the individual components;
wherein said combination has synergistic antioxidant properties when the antioxidant potential of the combination is higher than the sum of the antioxidant potential of the individual components.

DETAILED DESCRIPTION OF THE INVENTION

Brief Description of the Drawings

FIG. 45 is a table that summarizes results obtained for all formulations tested.

FIG. 46 shows the antioxidant potential of maple syrup (SE), stevia, steviol glycosides (stevioside, rebaudioside A), aspartame and sucralose, individually or in combination. The results are representative of 3 separate experiments.

ABBREVIATIONS

Figure 1:
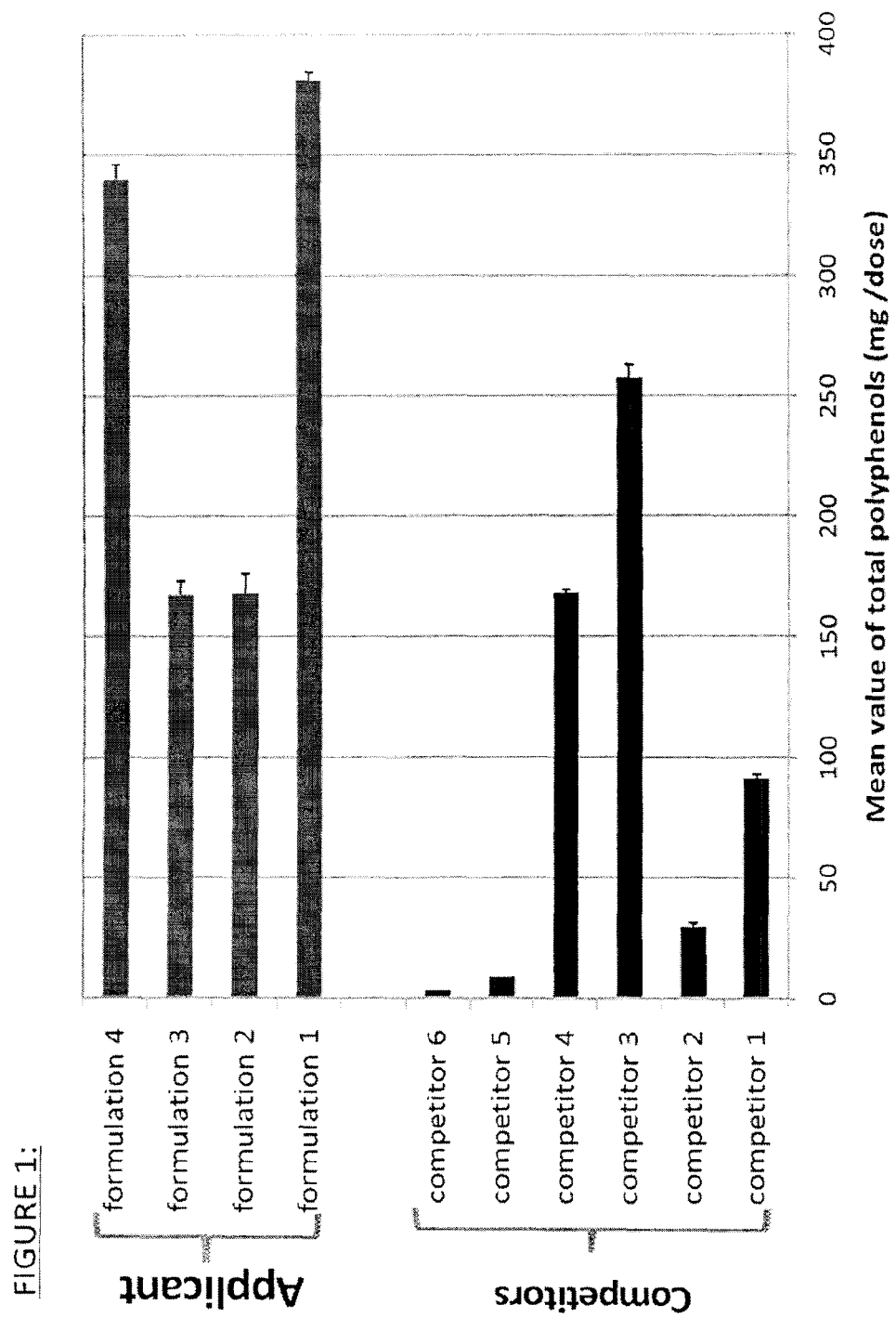
FIG. 1 shows the levels of polyphenols per dose present in various formulations.

The term "ECSIT" means evolutionarily conserved signaling intermediate in Toll pathways The term "ORAC" means Oxygen Radical Absorbance Capacity and is expressed in ORAC value when measured in μmol Trolox equivalent (TE/ml).

The term "TRAF6" means TNF receptor associated factor (TRAF) 6.

Definitions

In the present description, a number of terms are extensively used. In order to provide a clear and consistent understanding of the specification and claims, including the scope to be given such terms, the following definitions are provided.

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

The term "concentrate" means a composition comprising substantially all the same ingredients as the native fruit/vegetable/herb but in at a higher concentration i.e. where a portion or all of the water/solvent has been removed.

The term "extract" are used herein means a type of concentrate where certain active compounds are enriched when compared to other compounds in the native fruit/vegetable/herb composition.

The term "subject" or "patient" as used herein refers to an animal, preferably a mammal, and most preferably a human who is the object of treatment, observation or experiment.

"Mammals" includes humans, domestic animals such as laboratory animals and household pets, (e.g. cats, dogs, swine, cattle, sheep, goats, horses, rabbits), and non-domestic animals such as wildlife and the like.

The term "herbal extract" as used herein defines an extract that is obtained from a plant, or a herb, including flowers, stems, roots, seeds and leaves.

The term "plant-product" as used herein defines an extract that is obtained from the product of a plant such as, for example, a fruit or a vegetable, or a seed.

The compounds and extracts described herein can be formulated as ingestible compositions by formulation with additives such as physiologically acceptable excipients, physiologically acceptable carriers, and physiologically acceptable vehicles, or as nutraceutical or nutritional formulations with additives such as nutraceutically or nutritionally acceptable excipients, nutraceutically or nutritionally acceptable carriers, and nutraceutically or nutritionally acceptable vehicles. As used herein, the term "physiologically acceptable" refers to molecular entities and compositions that are physiologically tolerable and do not typically produce an allergic or similar unwanted reaction, such as gastric upset, dizziness and the like, when administered to human. The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for injectable solutions.

The compounds, compositions and extracts of the present invention can be prepared as nutritional formulations such as foods, including medical or functional foods and dietary supplements. A "medical or functional food" is defined as being consumed as part of a usual diet but which has been demonstrated to have physiological benefits and/or to reduce the risk of a disease or condition such as a chronic disease, beyond basic nutritional functions. A "dietary supplement" is defined as a product that is intended to supplement the human diet and is typically provided in the form of a pill, capsule, tablet, or like formulation. By way of example, but not limitation, a dietary supplement may include one or more of the following ingredients: vitamins, minerals, herbs, botanicals, amino acids, dietary substances intended to supplement the diet by increasing total dietary intake, and concentrates, metabolites, constituents, extracts or combinations of any of the foregoing. Dietary supplements may also be incorporated into food stuffs, such as functional foods designed to promote health or to prevent disease or disorders. If administered as a medicinal preparation, the composition can be administered, either as a prophylaxis or treatment, to a patient in any of a number of methods. The subject compositions may be administered alone or in combination with other pharmaceutical agents and can be combined with a physiologically acceptable carrier thereof. The effective amount and method of administration and aim of the particular formulation can vary based on the individual subject, the stage of the disease or condition, and other factors evident to one skilled in the art. In the case of a pharmaceutical formulation as well as a nutraceutical formulation, during the course of the treatment, the concentration of the subject compositions may be monitored (for example, blood plasma levels may be monitored) to insure that the desired level is maintained.

The term "nutraceutical" has been used to refer to any substance that is a food or a part of a food and provides medical or health benefits, including the prevention and treatment of disease or condition. Thus, a nutraceutical is a product isolated or purified from foods that is generally sold in medicinal forms not usually associated with foods. A nutraceutical is demonstrated to have a physiological benefit or provide protection against chronic disease. Hence, compositions falling under the label "nutraceutical" may range from isolated nutrients, dietary supplements and specific diets to genetically engineered designer foods, herbal products, and processed foods such as cereals, soups and beverages. In a more technical sense, the term has been used to refer to a product isolated or purified from foods, and generally sold in medicinal forms not usually associated with food and demonstrated to have a physiological benefit or provide protection against chronic disease. Suitable nutraceutically acceptable excipients may include liquid solutions such as a solution comprising a vegetable- and/or animal- and/or fish-derived oil.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds, compositions and extracts of the present invention may be administered as either a food or a food supplement. For example, when provided as a food, the extracts of the present invention are combined with material primarily made up of protein, carbohydrate and/or fat that is used in the body, preferably a human body, to sustain growth, repair, and vital processes, and to furnish energy. When provided as a food supplement, the compositions comprise selected substances such that they can be eaten at or about the same time as a food. The food supplements are generally eaten within about one hour before or after the food is eaten, typically within about one-half hour before or after the food is eaten, preferably within about 15 minutes of when the food is eaten, and further preferably within one to five minutes of the time the food is eaten. The food supplement can also be eaten at the same time as the food, or even with the food.

A "natural product" refers to naturally-occurring compounds that are end products of secondary metabolism; often, they are unique compounds for particular organisms or classes of organisms. An "all-natural product" refers to a product made with and/or from only natural compounds or products.

"Organic certification", "organic certifiable" or the like refers to a certification process for producers of organic food and other organic agricultural products. In general, any business directly involved in food production can be certified, including seed suppliers, farmers, food processors, retailers and restaurants. Requirements vary from country to country, and generally involve a set of production standards for growing, storage, processing, packaging and shipping that include, for example: avoidance of most synthetic chemical inputs (e.g. fertilizer, pesticides, antibiotics, food additives), genetically modified organisms, irradiation, and the use of sewage sludge; use of farmland that has been free from synthetic chemicals for a number of years (often, three or more); keeping detailed written production and sales records (audit trail); maintaining strict physical separation of organic products from non-certified products; and undergoing periodic on-site inspections. In some countries, certification is overseen by the government, and commercial use of the term organic is legally restricted.

An "organic food" refers to a food made with ingredients derived from crops obtained from organic farming and made in a way that limits or excludes the use of synthetic materials during production. Organic agricultural methods are internationally regulated and legally enforced based in large part on the standards set by the International Federation of Organic Agriculture Movements (IFOAM). For greater clarity, unless otherwise specified the use herein of the term "organic" preceding any plant, herb, animal or food product thereof refers to a product made with ingredients derived from crops obtained from organic farming and made in a way that limits or excludes the use of synthetic materials during production.

"As used herein, the phrase "sweetening compounds", "sweetener compounds", "sweetener" or the like generally refers to a natural additive which increases the basic taste of sweetness of a product to be ingested and can be considered as a sugar substitute (with or without additional calories).

"Antioxidant compounds" refers to any molecules capable of slowing or preventing the oxidation of other molecules that may cause oxidative stress and may damage or kill cells. Oxidative stress is thought to be associated with many human diseases.

A "food additive" refers to any substance added to foods during processing thereof to improve characteristics such as color, texture, flavor, and/or conservation. A "food supplement", "dietary supplement" or "nutritional supplement", refers to a preparation intended to provide nutrients, such as vitamins, minerals, fiber, fatty acids or amino acids, that may be missing or may not consumed in sufficient quantities in an individual's diet.

"Medical food" refers to any food that is specially formulated and intended for the dietary management of a disease that has distinctive nutritional needs that cannot be met by normal diet a/one.

A "functional food" is similar in appearance to, or may be, a conventional food that is consumed as part of a usual diet, and is demonstrated to have physiological benefits and/or reduce the risk of chronic disease beyond basic nutritional functions, i.e. they contain a bioactive compound.

"Synergy" is the condition where a combination of ingredients generates a higher activity (chemical and/or biological) than the sum of their individual ingredients for that same activity.

DETAILED DESCRIPTION OF PARTICULAR EMBODIMENTS

Because maple syrup and other natural sweeteners of the present invention has sweetening potential with antioxidant activity, it can be of special interest to the food industry, for example, as a food additive, a food supplement, and/or a functional food.

Therefore, in a first aspect, the invention relates to the potentiated antioxidant potential of a natural health products formulated with a combination having the following main ingredients: at least one of an antioxidant herbal extract, at least one of an antioxidant fruit extract; and at least one of a natural sweetener having antioxidant properties. This combination creates synergy to potentiate the formulation's antioxidant potential. This invention proposes that the combination of a natural sweetener having antioxidant activity such as maple syrup, honey, corn syrup, coconut sugar, Stevia or steviol glycosides (such as, for example, stevioside or Rebaudioside A) or agave in combination with an antioxidant plant extract and an antioxidant fruit extract potentiates the anti-oxidant potential of the fruit and plant extracts to produce, a potent antioxidant functional food product.

In a further aspect, there is provided a composition having synergistic antioxidant properties, comprising: an antioxidant sweetener, an antioxidant fruit extract and an antioxidant plant extract, in such proportions that each component potentiates the antioxidant effect of other component. Particularly, there is provided a composition having synergistic antioxidant properties, essentially consisting of: an antioxidant sweetener, an antioxidant fruit extract and an antioxidant plant extract, in such proportions that each component potentiates the antioxidant effect of other component. More particularly, there is provided, there is provided a composition having synergistic antioxidant properties, consisting of: an antioxidant sweetener, an antioxidant fruit extract and an antioxidant plant extract, in such proportions that each component potentiates the antioxidant effect of other component; and a flavor or aroma.

Food Format

Particularly, with respect to the above-mentioned aspects, the functional food products to which this invention can apply to include functional ingredients is selected from the group consisting of: liquid or solid food, formulated for oral intake. Particularly, the liquid food can be in the form of a functional beverage or in the form of a solid in concentrated form (such as a tablet, capsule, caplet or a powder) to be dissolved in water (such as plain water, carbonized water, source water or mineral water) prior to consumption. Particularly, the solid food can be in the form of a capsule for direct ingestion, or a bar or may take a semi-solid form (such as a pudding or yogurt). In the latter case, the combination can be formulated as nanoparticles to stay in suspension and be protected from the other ingredients.

Particularly, the composition may further comprise flavor or aroma, more particularly, the flavor or aroma is natural.

Antioxidant Synergistic Food Combinations

In a further aspect of the invention, there is provided a method for the identification of synergistic antioxidant compositions, the method comprising the steps of:

measuring the antioxidant potential of each component individually;

measuring the antioxidant potential of the components when combined; and comparing the antioxidant potential of the combination versus the individual components;

wherein said combination has synergistic antioxidant properties when the antioxidant potential of the combination is higher than the sum of the antioxidant potential; of the individual components.

Antioxidant Fruit/Vegetables Extracts:

Anthocyanins contained in blueberry, bilberry, cranberry, elderberry, raspberry seeds and strawberry can reduce age-induced oxidative stress, modulate inflammatory responses, and cal also improve neuronal and cognitive brain functions, ocular health, and protect genomic DNA integrity (Zafra-Stone et al, 2007). Applicant's invention can involve any fruit/vegetable extract containing at least one fruit/vegetable extract with antioxidant property.

Fruits and vegetables and their extract that have high antioxidant properties may be selected from: Acai, apple, apricot, avocado, banana, bakeapple, blackberry, blueberry, cherry, chokeberry, cloudberry, cranberry, current, dates, elderberry, fig, dogberry, gooseberry, grapefruit, grape, guava, raspberry, strawberry, kiwi, lemon, lime, makiang, maloud, mango, mango steam, melon, nectarine, noni fruit, orange, papaya, peach, pear, pineapple, plum, pomegranate, prune, raisin, rosehip, tangerine, watermelon, alfalfa seed sprouted, artichoke, arrugula, asparagus, lima bean, bean, beet, broccoli, cabbage, carrot, cauliflower, celery, chive, coriander, corn, cucumber, eggplant, fennel, leek, lemon balm, lettuce, mushroom, pea, pepper, tomato, pumpkin, radish, soy bean, spinach, squash, sweet potato.

Red wine is considered herein to be a fruit extract since it comes from grapes and contains many of the grape's polyphenols and other functional molecules.

This category also includes leguminous such as peas and lentil, particularly chick peas, cow peas, broad peas, and chocolate.

Plant/Herbs and Antioxidant:

The herbal extracts used in Applicant's functional drinks contain vitamins, polysaccharides, polyphenols (tannins, flavonoids), terpenes, alkaloides and organic acids (succinic, cafeic, chlorogenic, geranic). For details, refer to the table below or plant/herb file. Applicant's invention can involve any plant/herb extract containing at least one plant/herb extract with antioxidant property.

Antioxidant plant or herbal extracts or spices may be selected from: basil, dill weed, marjoram, oregano, peppermint, sage, savory, cardamon, chili, cinnamon, cloves, cumin, curry, garlic, ginger, Juniper plant, mustard, nutmeg, onion, paprika, parsley, pepper, poppy seed, rosemary, thyme, turmeric, vanilla beans, tarragon.

Teas are also included in the definition of herb/plant extract such as black tea, green tea, white tea, Labrador tea. Cereals can also be considered as plant/herb extract, such as, for example: rice, bran or sorghum.

Non-Exhaustive List of Herbal Extracts:

| English | Latin |
| --- | --- |
| Dandeleon root | Taraxacum officinale |
| Bilberry leaf | Vaccinium myrtillus |
| Galega leaf | Galega officinalis |
| Echinacea | Echinacea purpurea |
| Nettle | Urtica dioica |

-continued

| English | Latin |
| --- | --- |
| Sage | Salvia officinalis |
| Thyme | Thymus vulgaris |
| Lavender | Lavandula angustifolia |
| Hawthorn | Cratagus oxycantha |
| Verbena | Lippia citriodora |
| Rosemary | Rosmarinus officinalis L. |
| Lemon balm | Melissa officinalis |
| Peppermint leaf | Mentha × piperita |
| Oat | Avena sativa |
| Marshmallow root | Athaea officinalis |
| Red raspberry leaf | Rubus idaeus |
| Astragalus | Astragalus menbranaceus |
| Fennel seed | Foeniculum vulgare |
| Skullcaps | Scutellaria laterifolia |
| Yarrow | Achillea millefolium |
| Hyssop | Hyssopus officinalis |
| Motherwort | Leonurus cardiaca |
| Labrador tea | Ledum palustre |
| Garden angelica | Angelica archangelica L. |
| Winter Cherry | Withania somnifera |
| Fenugreek | Trigonella foenum-graecum |

Figure 47:
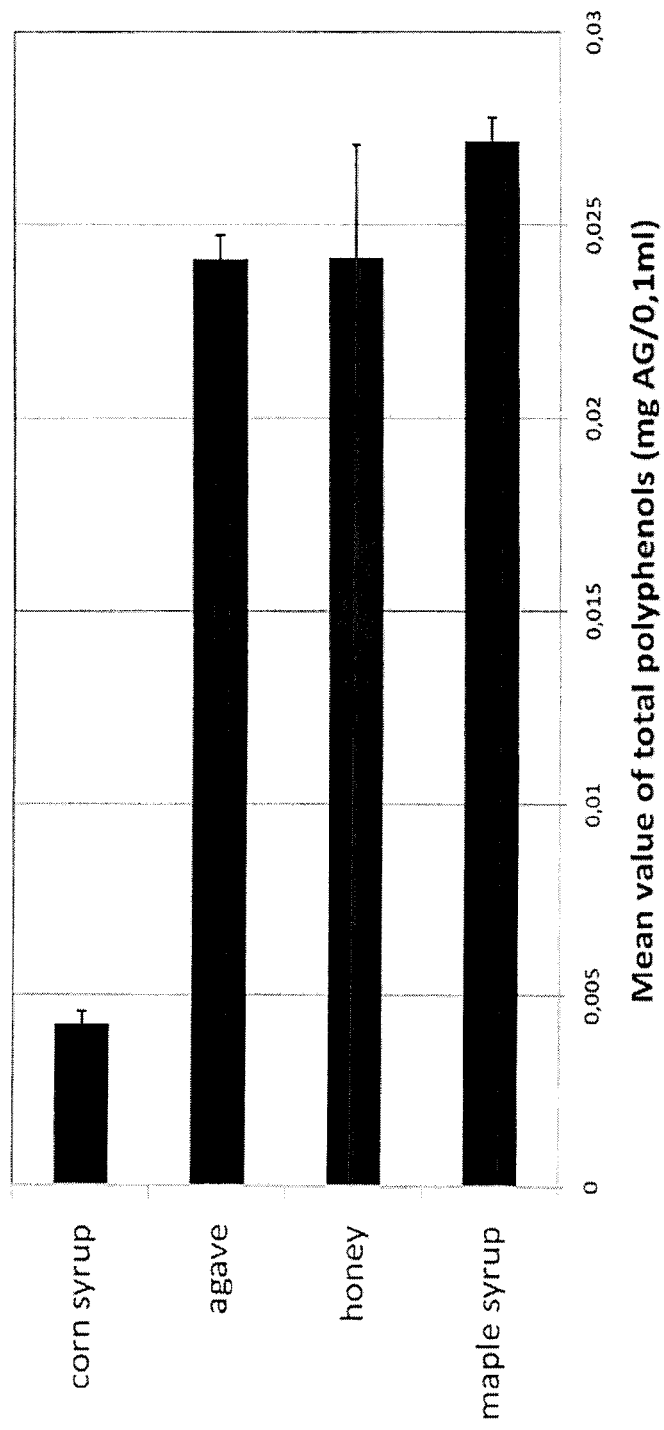
FIG. 47 shows the levels of polyphenols for different anti-oxidant sweeteners The results are representative of 3 separate experiments.

Anti-Oxidant Natural Sweeteners:

There is an increasing interest for natural sweeteners. This interest stems partially from increasing consumer demand for natural products, but also from the rise of a variety of businesses selling natural products and requiring suppliers of such products to certify that natural ingredients are used in any products being supplied. Sweeteners are divided into two major categories: nutritive and non-nutritive sweeteners. Nutritive sweeteners include sugar cane, high fructose corn syrup (HFCS), agave syrup, honey, and maple syrup. Non-nutritive sweeteners provide no energy (zero-calorie) and are further divided into two separate groups. You can have artificial/synthetic or natural non-nutritive sweeteners. These non-nutritive sweeteners are used in diet food products as sugar alternatives. Artificial or synthetic sweeteners that will be used in this study are aspartame and sucralose. The only natural zero-calorie sweetener is stevia, a sweetening extract rich in stevioside and rebaudioside A derived from the plant Stevie Rebaudiana. Once absorbed by the body, stevioside and rebaudioside A from stevia extract is metabolized into steviol. The molecular composition of each sweetener is also shown which involves various levels of sucrose, fructose, glucose, sucralose or maltose and the presence of other molecules with antioxidant and anti-inflammatory properties such as polyphenols (see FIG. 47). Since glucose is the main source of energy for brain cells, we will also use a glucose solution as the control of reference for sugar in our experiments.

Irrespective of the fact of whether a sweetener is nutritive or non-nutritive, or natural or artificial, it has been found by Applicant that only the following sweeteners have potent anti-oxidant activity that can synergize the anti-oxidant potential of other extracts such as from plants, vegetables or fruits. Such sweeteners are selected from: maple syrup, honey, coconut sugar, agave, corn syrup or stevia (or steviol glycosides such as stevioside or Rebaudioside A).

Particularly, the invention proposes that the composition comprises an anti-oxidant sweetener selected from the group consisting of: maple syrup, honey, agave or stevia (or steviol glycosides such as stevioside or Rebaudioside A). More particularly, the composition comprises maple syrup, honey, stevia, stevioside or Rebaudioside A. Most particularly, the composition comprises maple syrup or honey.

Maple Syrup:

Maple products obtained from the sap of maple tress (*Acer saccharum*) are typically viewed as sweeteners with energetic and sugar-containing nutritional potentials. However, maple syrup, native to North America, is much more than a concentrated sugar solution. It contains organic acids, amino acids, minerals, and a wide variety of unidentified compounds chemicals formed during the evaporation process that contribute to color and taste. It is non-obvious for the food industry to consider maple-derived ingredients for dietary products for individuals with diabetic and obesity problems.

Health Benefits of Maple Syrup:

Functional properties of maple syrup are numerous. There is now evidence that it also has anti-cancer properties, possibly due to its antioxidant properties. Various studies related to maple sap and maple syrup from Quebec showed that phenolic compounds (see Table 2) interfere with three essential phenomena involved in the development of tumors: oxidation, inflammation and angiogenesis, the process of developing new blood vessels (Béliveau et al, 2006, Legault J. et al, 2007).

TABLE 2

Table 1, Typical Organic Components of Maple Sap

| Component | Function of Total Organic Content[a,b] | Actual Concentration in Sap |
|---|---|---|
| Sucrose | 98.0-100% | 2-2.5% |
| Glucose | 0-0.17% | 0-0.004% |
| Phenolic compounds | 0-4.55 ppm | 0-0.1 ppm |
| Primary amines | 0.5-36.1 ppm | 0.01-0.9 ppm |
| Peptides | 0.4-18.6 ppm | 0.01-0.41 ppm |
| Amino acids | 0-11.3 ppm | 0-0.25 ppm |
| Protein | 0-50.9 ppm | 0-1.2 ppm |
| Other organic acids | 0-45 ppm | 0-1 ppm |

[a]The total solids in the sap are 1.0-5.4% and the pH of the sap is 3.9-7.9.
[b]The data are from ref 1, Appendix 2 and are used with permission.

Another study demonstrated that maple sap and syrup can inhibit nitric oxide overproduction and can have antiproliferative effect in cells in vitro (Legault et al, 2010). Recently, a research group identified 20 compounds, 13 of which were newly discovered (Li et al, 2010). Several of these antioxidant compounds newly identified have also been reported to have anti-cancer, anti-bacterial, and anti-diabetic properties. Maple syrup contains important quantity of abcissic acid, a phytohormone that stimulates insulin release through pancreatic cells and that increases sensitivity of fat cells to insulin, which makes it a potent weapon against metabolic syndrome and diabetes according to researchers from Rhode Island University. There is evidence that dietary abcissic acid can help ameliorate glucose tolerance and obesity-related inflammation in mice fed with high fat diets, and that it may also play a role in reducing the risk of atherosclerosis and IBD by suppressing the inflammatory conditions related with these diseases (Guri et al., 2010). Anti-hyperglycemic activity of maples products has been proposed, because the compound acertannin, known to have that activity has been isolated from maple leaves.

Specific Formulations

Particularly, there is provided a composition comprising: extract of Lemon balm, extract of Skullcaps (*Scutellaria*), blueberry concentrate, cranberry concentrate and maple syrup. More particularly, there is provided to use of such a composition for the relief of nervousness or sleeplessness due to mental stress.

Particularly, there is provided a composition comprising: extract of Hawthorn, extract of Skullcaps, apple concentrate, cranberry concentrate and maple syrup. More particularly, there is provided to use of such a composition for supporting cardiovascular health in adults and helping relieve nervousness.

Particularly, there is provided a composition comprising: extract of Skullcaps, extract of Raspberry bush, Yarrow, apple concentrate, cranberry concentrate and maple syrup. More particularly, there is provided to use of such a composition for the maintenance of women's health, particularly for the relief of menstrual pain.

Particularly, there is provided a composition comprising: extract of Thyme, extract of Hyssop, apple concentrate, cranberry concentrate and maple syrup. More particularly, there is provided to use of such a composition for the maintenance of digestive health, particularly for the relief of flatulent dyspensia and/or colics.

Use for the Maintenance of Homeostasis

In a further aspect of the invention, there is provided a method for the maintenance of homeostasis in a mammal, the method comprising the steps of: ingesting a food or a composition that is a TLR modulator. Particularly, the food or composition is as defined herein.

Method for the Identification of Foods Useful for Homeostasis

In a further aspect of the invention, there is provided a method for the identification of a food or a food ingredient useful for the maintenance of homeostasis in a mammal, the method comprising the steps of:

measuring the TLR activity by said food or food ingredient;

whereby said food or food ingredient is a TLR modulator when said TLR modulates the release of one of: IL10, IL6, MIP3α, dopamine and ATP; or a decrease in cell death or reactive oxygen species (ROS).

Inflammation and Homeostasis

Chronic Inflammation:

Research by scientists at the University of California, San Diego, and Switzerland's University of Fribourg discovered that inflammation provoked by immune cells called macrophages leads to insulin resistance and then to type II diabetes. Their research also showed that obesity without inflammation doesn't result in insulin resistance. Neurodegenerative diseases are characterized by the loss of either specific neurons or the impairment of specific neurotransmission function. Parkinson's disease is characterized by the progressive loss of dopaminergic neurons in the substantia nigra. Neuroinflammation is believed to contribute to the pathogenesis of PD and neurodegeneration is associated with activated microglia. Alzheimer's disease (AD) is characterized by the accumulation of extracellular amyloid plaques and intracellular neurofibrillary tangles leading to dysfunction mainly to cholinergic neurons. Various cytokines (IL-1, IL-6 and TNF-alpha) are especially elevated in AD patients. Huntington's disease (HD) is characterized by the progressive loss of neurons of the basal ganglia region including striatal cells. The pathogenesis of HD appears to involve chronic ATP depletion, oxidative stress and mitochondrial dysfunction. These cell conditions are known to produce pro-inflammatory responses. Amyotrophic lateral sclerosis (ALS) is characterized by the progressive loss of motor neurons in the central nervous system (brain and spinal cord) that control voluntary muscle movement.

Use Against Inflammation:

In a further aspect of the invention, there is provided a method for preventing inflammation in a mammal, the method comprising the steps of: ingesting a food or a composition that is TLR modulator. Particularly, the food or composition is as defined herein.

Toll-Like Receptors (TLRs)

TLRs are evolutionary-conserved type I transmembrane proteins (TLR1-11) that can recognize specific patterns of various types of molecules of bacterial, viral, parasitic, fungal or host origin. Thus, TLRs are versatile but selective. TLR activation triggers signaling cascades that result in the transcription of a multitude of inflammatory and immunomodulatory genes such as cytokines, chemokines and co-stimulatory molecules critical in determining the fate of immune responses. For that reason, TLRs are often considered critical linkers of innate and adaptive immunity. TLRs are abundantly present in immune cells that have the capacity to present antigens to lymphocytes in order to control the fate of the immune responses. Immune TLR-expressing cells include dendritic cells, macrophages, NK cells, and microglia located in the central nervous system.

TLRs in Mucosal Epithelia:

TLRs are present on epithelial cells of mucosal surfaces. For example. TLRs are abundantly expressed at mucosal surfaces, in the buccal cavity in taste bud cells. Recent evidence shows that epithelial TLR2 and TLR4 are involved in gatekeeping functions of the mucosa (Chabot et al, 2006). They demonstrated that activation of TLR2 mediates mucosal uptake of particles by the follicle-associated epithelium of intestinal Peyer's patches, which results in enhanced numbers of subepithelial dendritic cells (DCs) located into the FAE (Chabot et al, 2006, 2007, 2008, Anasova et al, 2008), suggesting that TLR2 activation causes the release of signals that attracts DC to take up particles that are transported across the FAE. Interactions between epithelial cells (ECs) and DCs provide an important bridge critical in determining the fate of immune responses. ECs "educate" sub-epithelial DCs through mechanisms that include the release of soluble mediators, such as the DC-attracting chemokine MIP3alpha. The release of MIP3alpha is also induced upon TLR2 activation. Although villus and crypt epithelial cells express TLRs at their apical poles in vivo, the intestinal mucosa of healthy individuals nevertheless coexists with the commensal microflora without chronic inflammation. It is thought that sensing of commensal bacteria through epithelial TLRs in vivo contributes to TLR-dependent intestinal homeostasis observed in vivo. Expression of TLR2, TLR3 and TLR4 has been shown in a human salivary gland cell line and their expressed was enhanced in labial salivary glands of patients with Sjögren's syndrome. Activation of intestinal epithelial TLR results in the release of IL-6, IL-10, and TNFalpha (de Kivit et al, 2011).

TLRs and Homeostasis:

TLRs participate in maintenance of tissue homeostasis and responses to injury. In the gut, the role of TLR has been associated with intestinal development, epithelial cell homeostasis and gut repair mechanisms. Indeed, deregulation of TLR signaling in the gut can result in chronic inflammation and excessive and even destructive repair responses that may be associated with diseases like colon cancer and inflammatory bowel diseases. Several negative regulators of TLR signaling that include IRAK-M, Tollip, SIGIRR, A20, Nod and PPARgamma contribute to control their activation in the intestinal epithelium in order to avoid prolonged and excessive activation of TLRs leading to uncontrolled inflammation detrimental to the host. In the pancreas, TLR signaling through the adaptor protein Myd88 has been shown to mediate a homeostatic effect on beta cells primarily in the setting of injury. The role of TLR2 in mucosal homeostasis is of particular interest because it appears to play a specific role in gatekeeping functions of mucosal intestinal epithelial cells (Chabot et al, 2006). A recent study demonstrates that TLR2 act as a transporting receptor that triggers uptake of TLR ligand across intestinal epithelial cells from the apical side to the basolateral side of the epithelial barrier by exosome-associated transcellular transcytosis (Bu et al, 2010). Studies aimed to determine the functional relevance of TLR to control tight junction-associated intestinal epithelial barrier integrity to balance mucosal homeostasis against inflammatory stress-induced damage show that oral intake of TLR2 ligand significantly inhibited mucosal inflammation and apoptosis by impacting epithelial integrity in vivo. This study suggests that TLR2 controls mucosal inflammation by regulating epithelial barrier function (Cario et al, 2007, 2008). A recent study shows that TLR activation affect gap junctional intercellular communication by modulating connexin-43 synthesis, suggesting that TLR2 regulates epithelial barrier functions through this mechanism (Ey et al, 2009). The role of TLR2 in regulating mucosal homeostasis is further confirmed in interleukin-10 deficient mice that develop experimental colitis. These studies suggest that TLR2 contributes to the anti-inflammatory action of IL-10 since IL-10 deficient mice lack TGF-beta/Smad-mediated TLR2 degradation that inhibits proinflammatory gene expression in intestinal epithelial cells under chronic inflammatory conditions. The protective role of TLR2 is further demonstrated using TLR2-deficient mice to study the development of colitis-associated colorectal cancer. Indeed, TLR2-deficient developed more and larger colorectal tumors (Lowe et al, 2010). Finally, TLR2 plays a role in glucose homeostasis since it was shown to be involved in insulin resistance and pancreatic beta cell function. Data show that glucose tolerance, insulin sensitivity and insulin secretion were improved in TLR2-deficient mice under high-fat diet, while tissue inflammation is reduced (Ehses et al., 2010). This study further suggest that TLR2 plays a role in the regulation of glucose homeostasis and the regulation of tissue inflammation.

TLRs in Diseases:

Among the TLRs, TLR2 and TLR4 play a critical role in the pathogenesis of diabetes, obesity and neurodegenerative diseases demonstrated in both clinical and experimental conditions.

Plant/Herbs/Food and TLRs:

Plant/herb-derived molecules can impact the TLR system. Recent evidence supports the search for plant/herb-derived TLR antagonists, as potential anti-inflammatory agents. It has been shown that some plant/herb-derived compounds can activate both innate and adaptive immunity through toll-like receptors signaling pathways and particularly the toll-like receptor 4 (TLR4) signaling pathway. TLR4 is a promising molecular target for immune-modulating drugs, and TLR4 agonists are of therapeutic potential for treating immune diseases and cancers. Several medicinal herb-derived components have recently been reported to act via TLR4-dependent pathways, suggesting that medicinal plant/herbs are potential resources for identifying TLR4 activators. Interestingly, anticancer drug Paclitaxel from Pacific yew tree interacts with human MD-2 and activates dendritic cells through TLR4. In 2006, scientists have discovered that dioscorin, a glycoprotein from *Dioscorea alata*, is a novel TLR4 activator and induces macrophage activation via typical TLR4-signaling pathways (Fu et al 2006). Datia et al (2010) showed that 9,10-Dihydro-2,5-dimethoxyphenanthrene-1,7-diol, a phenanthrene isolated from *Eulophia ochreata*, one of the Orchidaceae family, blocked signals generated by TLR4 activation, as shown by down-regulation of NF-kappaB-regulated inflammatory cytokines. It is known that the intake of glucose or a high-fat, high-carbohydrate meal induces an increase in inflammation and oxidative stress in circulating mononuclear cells (MNCs) of normal-weight subjects. A recent study has shown that the combination of glucose or water and the HFHC meal induced oxidative and inflammatory stress and an increase in TLR expression and plasma endotoxin concentrations. In contrast, orange juice intake with the HFHC meal prevented meal-induced oxidative and inflammatory stress, including the increase in endotoxin and TLR expression (Ghanim et al. 2010). Saponines from plant can suppress TLR4-mediated inflammatory cytokine production and NF-κB activation specifically by inhibiting TLR4 ligand binding to TLR4-MD-2. This is the case for saponine from *Glycyrrhizae Radix* (Honda et al. 2010). In 2009, Mirsha et al have shown that aqueous *rhodiola imbricata* rhizome extract induced TLR-4 expression and intracellular granzyme-B in treated splenocytes while the same extract stimulated IL-1beta, IL-6, and TNF-alpha in human peripheral blood mononuclear cells suggesting that aqueous rhodiola extract could be used in modulating the immune system of immunocompromised individuals. From a mode of action standpoint, to activate the downstream signaling pathways and subsequently induce immune responses, ligand-induced dimerization of TLR4 is required. A 2006 study implies that phytochemicals consumed on a daily basis can contribute to the activation of immune inflammatory responses by activating TLR receptors. This study showed that TLR 4 receptors are the molecular target of curcuma. Curcumin and sesquiterpene lactone inhibit both ligand-induced and ligand-independent dimerization of TLR4 (Young et al. 2006). Plant derived polyphenols, in particular the polyphenol epigallocatechin-3-gallate isolated from green tea have been shown to downregulate TLR4 signal transduction (Byun et al 2010).

TLRs and Immune Tolerance:

Immune tolerance is the process by which the immune system remains unresponsive to antigens that can be self or foreign in nature. There are 3 forms of immune tolerance: central, peripheral and acquired. Oral tolerance is the most important form of acquired tolerance and involves the suppression of specific immune responses to antigens administered orally that are not threatening to the organism, such as food or commensal flora. Dendritic cells (DCs), that act as the commander-in-chief of the immune system, can become tolerant to antigens and known as tolerogenic DCs. TLR2 activation of tolerogenic DCs results in enhanced anti-inflammatory responses and TLR2 expression.

IL-6:

IL-6 is a pro-inflammatory cytokine. IL-6 is pleiotropic cytokine involved in the physiology of virtually every organ system. Recent studies suggest that IL a very important regulator of Treg/Th17 balance. Moreover, IL-6 has neuro-specific activities including the modulation of the hypothalamic-pituitary-adrenal (HPA) function that plays a major role in regulating stress. IL-6 affects the CNS in that it activates the HPA axis and increases brain tryptophan and serotonin metabolism. It has been proposed that IL-6 could be a biomarker for aging and that it could link inflammation, obesity, stress and coronary heart diseases. Preclinical animals models have provided evidence that specific blockade of IL-6 may be an effective treatment for chronic inflammatory and autoimmune disease.

IL-10:

IL-10 is an anti-inflammatory cytokine that regulates the inflammatory responses. The interaction of IL-10 with its receptor can have various outcomes such as the induction of a cellular anti-viral state, the inhibition of pro-inflammatory response, the induction of apoptosis, and the modulation of cell growth. Mice deficient in IL-10 develop a chronic inflammatory bowel disease (IBD) that predominates in the colon and shares histopathological features with human IBD and TLR4 appears to contribute to the development of this condition. Importantly, IL-10 plays a crucial role in peripheral immune tolerance and in the control of epithelial homeostasis. Interestingly, IL-10-deficient mice lacking also the serotonin reuptake transporter have even more severe intestinal inflammation compared to mice with the serotonin reuptake transporter, suggesting that IL-10 also plays a role in neuroimmune interactions. Boosting IL-10 production is thought to be an effective therapeutic approach for autoimmune diseases and chronic inflammatory diseases.

Methods to Measure Antioxidant Potential

The antioxidant potential of any products can be measured using methods such as the chemical measure of high oxygen radical absorbance (ORAC) and the biochemical release of reactive oxygen species (ROS) from cells. (See materials and methods).

Use for Energy Lift

Mitochondrial Energy Production:

Mitochondria provide energy for basic metabolic processes through cell respiratory. This process can extract energy from organic substances in oxygen presence. In order to use the food we eat, our body must degrade the food into smaller molecules. After this, the cells will use these molecules, either as a source of energy, or as materials to construct other molecules. The first stage of degradation, digestion takes place in our intestinal cells. The digestion in our intestinal cells is the first step of degradation. Through the action of enzymes, the larger ingested molecules are degraded in intestinal cells. Proteins are degraded into amino acids, the polysaccharides into carbohydrates, fats into fatty acids and glycerol. Subsequently, small molecules derived from food will enter into the cell's cytosol and will begin their progressive oxidation. Carbohydrates and fats are the main sources of energy for most organisms, including humans. In the cytosol, each glucose molecule undergoes a series of chemical reactions called glycolysis which then the result is a molecule of pyruvate. The pyruvate can enter in the Kreb's cycle in mitochondria. For this research, we will focus on reactions confined to the mitochondria. It is in the membranes of mitochondria that much energy is produced. More than 90% of our cellular energy is produce by mitochondria. Carbohydrates and fats are the main sources of energy for most organisms, including humans. Furthermore, mitochondria provide essential metabolism such as heme biosynthesis, function in calcium and iron homeostasis, and play a key role in programmed cell death.

Diet and Mitochondrial Decay:

Diets deficient in nutrients can accelerate mitochondrial decay and contribute to neurodegeneration, and other dysfunction. Nutrient deficiency increase ROS and oxidative stress, and consequently leading to mitochondrial dysfunction and age-associated diseases, including metabolic syndrome. Vitamins, minerals and other metabolites play a key role as cofactors for the synthesis of mitochondrial enzymes and support mitochondrial function, including ATP synthesis.

Mitochondrial Nutrients:

Liu and al. (2009) ranked the <<mitochondrial nutrients>> in four groups according their beneficial functions. Mitochondrial nutrients can perform a numbers of beneficial functions: 1) prevent oxidant production or scavenge free radicals to eliminate oxidative stress in mitochondria; 2) act as enzyme inducers, can enhance antioxidant 3) enhance mitochondrial metabolism, by repairing and degrading mitochondria, and by increasing mitochondrial biogenesis; 4) protect mitochondrial enzymes and/or stimulate mitochondrial enzyme activity by elevating substrate and cofactor levels. They also classified mitochondrial nutrients into the following three groups: 1) antioxidants, such as coenzyme Q, lipoic acid (LA), glutathione, and α-tocopherol; 2) energy enhancers and others, such as carnitine/acetyl-Lcarnitine, creatine, pyruvate, and choline; and 3) cofactors and their precursors, such as lipoic acid, coenzyme Q, and the B vitamins.

Calcium Signaling and Energy Production:

Mitochondria play a key role in cellular $Ca^{2+}$ homeostasis. Mitochondria have an important influence in regulation of intracellular $Ca^{2+}$ in both normal and pathological cell function. This latter accumulate calcium and release them during certain cellular events. $Ca^{2+}$ act as second messenger in neurotransmitters release from neurons, and is implicated in contraction of all muscle cell types. Extracellular $Ca^{2+}$ maintains the potential difference across cell membranes. Many enzymes require also $Ca^{2+}$ ions as a cofactor. In mitochondria, the calcium can directly up-regulate enzymes of Kreb's cycle and other OXPHOS enzymes, resulting in faster respiratory chain activity and higher ATP output. ATP increase allows meet the cellular ATP demand. Thus any perturbation in mitochondrial or cytosolic $Ca^{2+}$ homeostasis will have heavy consequence for cell function, and the level of ATP synthesis. In the cell, there are also and important coordination between endoplasmic reticulum and mitochondria in order to regulate mitochondria morphology. Perturbation in this relation can lead to $Ca^{2+}$ overload and mitochondria fission, fragmentation, and apoptosis. It seems that $Ca^{2+}$ plays opposite roles intervening such a physiological stimulus ATP synthesis and can become a pathological stimulus for ROS generation, cytochrome c release, and apoptosis.

Energy Conservation and Homeostasis:

Meditation is used as an energy conservation technique. Highly experienced yogi have the capacity to meditate for very long periods of time without eating. Not much is known about the mechanisms underlying this enhanced capacity of energy conservation. If the body as a whole is functioning in a healthy and relaxed manner, it has the resources to fight a specific illness. Since meditation, with its ability to restore and maintain a general state of homeostasis, acts as the command post, this may be all you need to turn around a serious illness. Meditation works because it restores the body to a state of homeostasis, in which the systems within the body are at rest or operating within sustainable limits. The body is quite capable of operating outside the state of balance. We can run a marathon, for example, or eat a massive meal, without suffering unduly. However, when this occurs, these systems in the body are stressed. If the body is stressed for too long, damage takes place and pathologies start to occur. In fact, sickness can be easily defined as a state of imbalance in one or more of the systems in the body. The body is always striving to return to homeostasis. Not only do systems work best when in balance, but this is also the optimum state for self-repair and growth.

Functional drinks that induce a meditative state have not been described. This invention provides the first evidence that a meditative state does not necessitate a first input from the "spirit", and that it can be induced via the intake of a functional drink designed to induce a state of energy conservation.

In a further aspect of the invention, there is provided a method to provide an energy lift in a mammal, the method comprising the steps of ingesting a food or a composition as defined herein.

Use for Neuroprotection

ATP and Neurotransmission:

In addition to its energetic role, ATP serves an important function in neurotransmission. Indeed, ATP signalling is crucial for communication from taste bud cells and the gustatory nerves that are in contact with the taste bud cells of the tongue. These gustatory nerves communicate with the brain center to regions that are involved in reward mechanisms. The dopaminergic system is an important regulator of this reward center that involves in particular the ventral forebrain structures, such as the hypothalamus, the amygdala, and the nucleus accumbens.

In a further aspect of the invention, there is provided a method for the protection of the nervous system in a mammal, the method comprising the steps of: ingesting a food or a composition as defined herein.

Use for Cardioprotection

In accordance with a further aspect of the invention, there is provided a composition useful for use in cardioprotection in a mammal, wherein the composition has anti-atherosclerotic activity, anti-hypertensive activity, and anti-arteriosclerosis activity. Particularly, due to the presence of berry anthocyanins, formulations 1 and 2 may act as cardioprotectant by maintaining vascular permeability, reducing inflammatory vascular responses, platelet aggregation and by offering superior vascular protection.

Use for Homeostasis

In accordance with a further aspect of the invention, there is provided a composition useful for use in maintaining, preserving or recovering homeostasis in a mammal, wherein the composition has TLR2 activity. Particularly, due to the presence of plant/berry polyphenols and berry anthocyanins, formulations 1 and 2 may act as TLR2 inhibitors and homeostasis promoters.

The present invention is illustrated in further details by the following non-limiting examples.

EXAMPLES

Material and Methods

Formulations:

Table 3 describes the composition and associated usage of each formulations developed by Applicant. As indicated, Formulation 1 is an adaptogenic formulation used for the relief of nervousness or sleeplessness due to mental stress, while Formulation 2 is for the maintenance of cardiovascular functions.

Table 4 described the ingredients of the formulations and competitors used in this study. Ingredients are listed in order of proportion, from the most abundant to least abundant.

Molecules that may act as potential active ingredient present in each formulation developed by Applicant and their reported beneficial effects are described in Tables 5, 6, 7 and 8. Note that other potential molecules may be present in trace or undetectable amount, and are not listed in the tables.

TABLE 3

Beverage Composition (per dose of ready-to-drink 300 ml) and associated usage

| Formulation 1 | Formulation 2 | Formulation 3 | Formulation 4 |
|---|---|---|---|
| Herbal mix containing: Limon balm 1-2 g/L *Scutellaria* 0.5-1.5 g Blueberry concentrate 5-15 g Cranberry concentrate 1-5 g Maple syrup 10-20 g Natural aroma 0.01-0.1 g | Herbal mix containing: Hawthorn 1-2 g *Scutellaria* 0.3-1 g Apple concentrate 10-20 g Maple syrup 5-10 g Cranberry concentrate 1-5 g Natural aroma 0.01-0.1 g | Herbal mix containing: *Scutellaria* 0.50-1.5 g Raspberry bush 0.5-1.5 g Yarrow 0.2-0.8 g Apple concentrate 2-10 g Cranberry concentrate 1-5 g Maple syrup 10-20 g Natural aroma 0.01-0.1 g | Herbal mix containing: Thyme 1-2 g Hysop 2-4 g Apple concentrate 10-20 g Cranberry concentrate 1-5 g Maple syrup 5-10 g Natural aroma 0.01-0.1 g |
| Use: Helps relieve nervousness, and sleep aid in case of restlessness or insomnia due to mental stress Relaxation formula with energizing potential | Use: Helps support cardiovascular health in adults and helps relieve nervousness. Cardioprotective formula with energizing potental | Use: Helps maintain women's health. Helps relieve menstruation pain. Formula for hormonal balance, for women only | Use: Digestive tonic. Helps relieve abdominal discomfort due to flatulent dyspepsia and colics. Formula used as an alternative to dairy-based probiotics |

TABLE 4

Ready-to-drink formulations from Applicant and competitors and their ingredients per dose

| | Formulations | | | | | | |
|---|---|---|---|---|---|---|---|
| | Formulation 1 | Formulation 2 | Competitor 1 | Competitor 2 | Competitor 3 | Competitor 8 | Competitor 9 |
| Ingredients (listed in order of proportion from most abundant to least abundant) | Herbal extract containing: lemon balm 1.21 g (melissa officinalis) skullcap 0.73 g (*scutellaria laterifolia*) maple syrup blueberry concentrate cranberry concentrate natural aroma | Herbal extract containing: hawthorn 1.25 g (crategus oxyacantha) skullcap 0.44 g (*scutellaria laterifolia*) maple syrup cranberry concentrate apple concentrate natural aroma | Green tea (from real brewed green tea concentrate) Raw sugarcane Pomegranate juice from concentrate Natural flavor Citric acid Ascorbic acid (vitamin C) Sodium citrate | Glucose-fructose Citric acid Concentrated tea from tea leaves Potassium citrate Natural lemon flavor | Fruit juice from concentrate - grape apple pomegranate cranberry blueberry lemon elderberry blackberry Natural flavour Ascorbic acid (Vitamin C) | Glucose-fructose Coca-cola mix Caramel colour Phosphoric acid Natural flavour caffeine | Taurine 1000 mg Glucuronolactone 600 mg Caffeine 80 mg Niacin (niacinamide) 18 mg Pantothenic acid (calcium d-pantothenate) 6 mg Vitamine B6 (pyridoxine HCl) 2 mg Riboflavine 1.65 mg Vitmaine B12 (cyanocobalamine) 1 mcg Sucrose Glucose Citric acid Inositol Natural aroma caramel |

TABLE 5

Formulation 1 ingredients

| Ingredients | Potential detectable molecules | Reported Beneficial Effects |
|---|---|---|
| Herbal infusion *Melissa officinalis* *Scutellaria laterifolia* | *Melissa* extract Polyphenols Flavonoids: Apigenin (A) and luteolin (L) *Scutellaria* extract Polyphenols Flavonoids: Wogonin (W), Baicalein (B1), Baicalin (B2) | Monoamine transporter activator (A, L) Anti-cancer (A, L) Autophagia (cellular dormancy/energy conservation) (A) inhibitor of cytochrome 450 (A, B1) Prevent renal damage due to cyclosporin (A) anxiolytic (A, W) antioxidant (L) anti-septic shock (L) neuroprotective in MS (L) anti-inflammatory (B1) enhance liver health (W, B2) muscle relaxant (W) prolyl endopeptidase inhibitor, affect GABA receptors (B2) |

TABLE 5-continued

Formulation 1 ingredients

| Ingredients | Potential detectable molecules | Reported Beneficial Effects |
| --- | --- | --- |
| Cranberry concentrate *Vaccinum macrocarpum* | Polyphenols Flavonoids: Proanthocyanins (P), Anthocyanins (AN) | Antioxidant activity (AN) Effect on urinary tract infections (P) Dental health Favorable Glycemic Response of Type 2 Diabetics |
| Blueberry concentrate *Vaccinum* spp. | Polyphenols Flavonoids: Anthocyanins (AN) | anti-cancer (AN) anti-hypercholesterolemia (AN) anti-hyperglycemic (AN) anti-diabetic (AN) anti-inflammatory (AN) anti-microbial (anti-fungal, anti-viral) (AN) neuroprotective (reduction of cognitive decline) (AN) Cardioprotection (AN) |
| Maple syrup *Acer saccharum* | Phytohormones Abcisic acid (AB) | Ameliorate inflammatory bowel disease (AB) ameliorates atherosclerosis (AB) ameliorates glucose tolerance and diabetes (AB) ameliorate obesity-related inflammation (AB) |

TABLE 6

Formulation 2 ingredients

| Ingredients | Potential detectable molecules | Reported Beneficial Effects |
| --- | --- | --- |
| Herbal infusion *Crataegus oxyacantha* *Scutellaria laterifolia* | *Crataegus* extract(CE) Polyphenols Flavonoids (F): Proanthocyanins (P), Quercetin (Q), Hyperoside (3-O-galactoside of quercetin, H), Rutin (flavonoid glycoside, R), Vitexin (apigenin flavone glucoside, V) *Scutellaria* extract Polyphenols Flavonoids: Wogonin (W), Baicalein (B1), Baicalin (B2) | Hypotensive effect(CE) Treatment for various cardiovascular conditions(F, H, V, Q) Beneficial effect on blood lipids(CE) Antioxidant activity(P, Q, H) Inhibitor of cytochrome 450 (B1) Anti-inflammatory (B1) Enhance liver health (W, B2) Muscle relaxant (W) Prolyl endopeptidase inhibitor, affect GABA receptors (B2) |
| Apple concentrate | Polyphenols Flavonoids: Proanthocyanins (P) | Beneficial effect on blood lipids (polyphenol in general) |
| Cranberry concentrate *Vaccinum macrocarpum* | Polyphenols Flavonoids: Proanthocyanins (P), Anthocyanins (AN) Flavonols (F), Quercetin (Q) Stilbenes: Resveratrol(R) Phenolic acids: Ellagic acid (EL) | Antioxidant activity (P, AN, F, Q, R, EL) Effect on urinary tract infections (P) Anti-cancer activity (Q, EL) Limit the development of vascular diseases(R) Dental health Anti-inflammatory (R) Favorable Glycemic Response of Type 2 Diabetics |
| Maple syrup *Acer saccharum* | Phytohormones Abcisic acid (AB) | Ameliorate inflammatory bowel disease (AB) ameliorates atherosclerosis (AB) ameliorates glucose tolerance and diabetes (AB) ameliorate obesity-related inflammation (AB) |

TABLE 7

Formulation 3 ingredients

| Ingredients | Potential detectable molecules | Reported Beneficial Effects |
| --- | --- | --- |
| Herbal infusion *Achillea millefolium* *Scutellaria laterifolia* *Rubus idaeus* | *Achillea* extract(AE) Polyphenols Flavonoids: Luteolin (L) Tannins (T) Phenolic acids Salicylic acid (SA) Alkaloid Achilleine, betaine, trigonelline, betonicide, stachydrine, and moschatine *Rubus* extract(RE) Polyphenols Flavonoids: Luteolin (L), Quercetin (Q), Kaempferol (K) Tannins Phenolic acids | Anti-inflammatory (AE) Antiangiogenic activity, cancer treatment(GA) Relaxant activity (RE) Antioxidant activity (Q) Inhibitor of cytochrome 450 (B1) anti-inflammatory (B1) enhance liver health (W, B2) muscle relaxant (W) prolyl endopeptidase inhibitor, affect GABA receptors (B2) |

TABLE 7-continued

Formulation 3 ingredients

| Ingredients | Potential detectable molecules | Reported Beneficial Effects |
|---|---|---|
| | Salicylic acid (SA), Ellagic acid (EL), Gallic acid (GA) | |
| | *Scutellaria* extract | |
| | Polyphenols | |
| | Flavonoids: Wogonin (W), Baicalein (B1), Baicalin (B2) | |
| Apple concentrate | Undetectable Polyphenols | Beneficial effect on blood lipids (phenolic compounds) |
| Cranberry concentrate *Vaccinum macrocarpum* | Undetectable Polyphenols | Favorable Glycemic Response of Type 2 Diabetics |
| Maple syrup *Acer saccharum* | Phytohormones<br>Abcisic acid (AB) | Ameliorate inflammatory bowel disease (AB)<br>ameliorates atherosclerosis (AB)<br>ameliorates glucose tolerance and diabetes (AB,)<br>ameliorate obesity-related inflammation (AB) |

TABLE 8

Formulation 4 ingredients

| Ingredients | Potential detectable molecules | Reported Beneficial Effects |
|---|---|---|
| Herbal infusion *Thymus vulgaris* *Hyssopus officinalis* | *Thymus* extract (TE)<br>Polyphenols<br>Flavonoids: Luteolin (L), Hispidulin (H)<br>Phenolic acids<br>Caffeic acid and rosmarinic acid<br>*Hyssopus* extract(HE)<br>Flavonoids: apigenin (A), quercetin (Q), diosmin (D), luteolin (L)<br>Phenolic acids<br>Chlorogenic, protocatechuic, ferulic, syringic, p-hydroxybenzoic and caffeic acids | Antioxidant activity(PA, H, F)<br>Antitussive action (TE)<br>antifungal and anti-bacterial properties(HE)<br>Anti-diabetes(reduced hyperglycemia)<br>Prevents the ascorbic acid oxidation(F)<br>Anti-cancer (H) |
| Apple concentrate | Polyphenols<br>Flavonoids: Proanthocyanins (P), Quercetin (Q) exclusively in peel, Catechin (C), Epicatechin (C), Cyanidin-3-galactoside-C3 (C3)<br>Phenolic acids<br>Chlorogenic acid (CH), Coumaric acid (CO), Gallic acid (GA)<br>Organic acids | Reduced risk for cancer, especially Jung cancer(F)<br>Positively associated with general pulmonary health(F)<br>Reduced risk of cardiovascular disease(F)<br>Reduced risk of Type II diabetes(Q)<br>Antioxidant activity(F, VC, C3, CA, CH, GA)<br>Beneficial effect on blood lipids(phenolic compounds) |
| Cranberry concentrate *Vaccinum macrocarpum* | Undetectable Polyphenols | Dental health<br>Favorable Glycemic Response of Type 2 Diabetics |
| Maple syrup *Acer saccharum* | Phytohormones<br>Abcisic acid (AB) | Ameliorate inflammatory bowel disease (AB)<br>ameliorates atherosclerosis (AB)<br>ameliorates glucose tolerance and diabetes (AB)<br>ameliorate obesity-related inflammation (AB) |

Polyphenol Detection

Total amount of polyphenols were measured by spectrophotometry using an adaptation of a protocol already described by Grubesic et al, 2005. Extraction of polyphenols was done by acidified methanol. 50% Folin (Sigma-Aldrich) was added to extracts, and absorbance was measured at 760 nm. Galic acid (GA) was used as positive control and results are expressed as mg equivalent GA pas 100 ml of extract.

Anthocyanin Detection

Anthocyanin levels were measured by HPLC and were performed by an independent laboratory.

Determination of Mitochondrial Activity:

Cell lines (CAL27, SH-SY5Y) used for this assay were plated in plaque assays at a density of 50,000-100,000 cells per well. Colorimetric MTT (3-(4,5-dimethylthiazol-2-yl)-2,5-diphenyl tetrazolium bromide) was dissolved in HBSS buffer to obtain a final concentration of 0.5 mg/ml per well. Cell plates were incubated for 2 hours at 37° C. Conditioned medium was then removed, and acid-isopropanol (0.04N HCl in isopropanol) was added to all wells. HCL was used as positive control to induce cell death. Plates were read at 530 nm/630 nm in a Synergy Biotek machine. The amount of dark blue crystals determined by spectrophotometry serves as an estimate for the number of mitochondria and hence the number of living cells in the test sample. This method is an adaptation of a previously described assay (Mossman, 1983).

Determination of the Antioxidant Capacity:

The antioxidant capacity of formulations and beverages was determined with the ORAC (Oxygen Radical Absorbance Capacity) test. ORAC assays were performed as previously described (Prior et al, 2005). This assay determines the ability of a sample to block the oxidation of fluorescein (40 nM) induced by 20 mM of [2,2-Azobis(2- methylpropionamide)dihydrochloride (AAPH), based on the oxidation of fluorescein by peroxyl radicals revealed by a reduction of emitted fluorescence over time. These free radicals are generated by the exposition of fluororescein to AAPH. A delay of this AAPH-induced oxidation reveals an antioxidant property. The oxidation process is a kinetic reaction that is measured fluorescence levels (excitation: 485 nm, emission: 528 nm) over time using a Synergy HT (Biotek) microplate reader. Area under the curves (AUC) from each compound tested are calculated and compared to the blank and the control of reference the vitamin E analog 6-Hydroxy-2,5,7,8 Teramethylchromane-2-carboxylic acid (Trolox). ORAC values are expressed as μmol of Trolox equivalent per ml (μmol TE/ml) of compound tested.

Cell Lines, Cultures and Reagents:

All cell lines were obtained from the American Type Culture Collection (ATCC, Manassas, US). Table 9 below describes the cell lines used and their culture condition. In some experiments, cells were transferred to a 96 wells plate and treated with different concentration of TLR2 agonist synthetic triacylated lipoprotein PAM3CSK4 (InvivoGen) starting by 500 ng/ml final concentration to activate TLR2.

secreted from cells were measured from conditioned cell culture supernatants. Both intracellular and secreted ATP using measured using an ATP determination kit purchased from Invitrogen (Molecular Probes). ATP levels were detected at luminescence 560 nm. ATP levels were normalized to untreated control and were expressed as % ATP levels.

Sample Collection (Saliva):

Saliva samples were collected from fasting 25-55 year old healthy volunteer individuals (men and women) who have the following profile: do not smoke, have no addictions, normal weight, active, exercizing at least 2-3 times a week. Volunteer were given 20 ml-size samples of various formulations that they had to drink on separate days, first thing in the morning. Before swallowing, sample formulations were kept in the mouth for at 15-20 seconds, after which saliva was collected over the next 5 minutes. Saliva samples were frozen immediately.

Detection of Salivary Dopamine

Levels of dopamine in human saliva samples were measured using a "Dopamine ELISA" kit by following the instructions provided by the company (Genway Biotech, CA).

TABLE 9

Cells lines and culture conditions

| Human cell line | Cell type | Culture condition |
|---|---|---|
| CAL27 | Tongue squamous epithelial cell carcinoma (ATCC CRL-2095) | Cells were grown in DMEM high-glucose 4.5 g/L culture medium containing 2 mM L-glutamine, 1 mM sodium pyruvate, 10% fetal bovine serum, and 100 ug/ml Pen/Strep. |
| SY-SH5T | Neuroblastoma that exhibit moderate levels of dopamine beta hydroxylase activity (ATCC CRL-2266) | Cells were grown in EMEM/F12 culture medium containing 10% fetal bovine serum. |
| HEK 293 | HEK-null: Primary embryonal kidney cells transformed by sheared human adenovirus type 5 DNA transfected with plasmid pUNO-mcs (Invivogen), HEK-TLR2: Primary embryonal kidney cells transformed by sheared human adenovirus type 5 DNA cotransfected with hTLR2 and CD14 genes (Invivogen). HEK-TLR4: Primary embryonal kidney cells transformed by sheared human adenovirus type 5 DNA cotransfected with hTLR4A, MD2, and CD14 genes (Invivogen). | Cells were grown in DMEM high-glucose 4.5 g/L culture medium containing 2 mM L-glutamine, 1 mM sodium pyruvate, 10% fetal bovine serum, 50 ug/ml Pen/Strep, 100 ug/ml Normocin and 10 ug/ml blasticidin. For HEK-TLR2, 50 ug/ml HygroGold was also added. |

Measurement of ROS Production:

Cellular ROS levels were obtained by measuring the oxidation of $CM-H_2DCFDA$ (5-(and 6)-chloromethyl-20, 70-dichlorodihydrofluresceindiacetate; Invitrogen) a cell-permeant indicator. Cal27, HEK 293 and SH-SY5Y were plated in 96 well plates at a cell density of 25000 cells per well. Cells were treated for 1 hour with 5 μM $CM-H_2DCFDA$. After removing the CDFDA solution, cells were treated with various adaptogenic formulations prepared with ROS buffer (HBSS containing 2% FBS). After 30 min of exposure with samples, a first reading was taken using the synergy HT (Biotek) plate reader. Various concentrations of AAPH (100 mM, 40 mM, 16 mM, 6.4 mM and 2.5 mM) were then added, and readings (excitation: 485 nm, emission: 530 nm) were taken every 30 minutes for 2 hours. The fluorescence intensity is an indicator of $H_2O_2$ intracellular level so values are expressed in Relative Fluorescence Unit (RFU).

Detection of ATP:

ATP intracellular levels were measured from whole cell lysates obtained through a freeze-thaw cycle, whereas ATP Statistical Analysis Statistical analysis was performed using GRAPH PRISM software. Experiments were done in triplicate. All data are presented as mean±SEM. Statistical analysis was done by using a Dunett comparison multiple tests, One-way ANOVA. Results were considered significant when $p \leq 0.05$.

Examples of Various Formulations of the Functional Food Products for the Present Invention Table 3 shows the constitution of functional formulations developed by Applicant. The four beverages are composed of three main natural ingredients: antioxidant herbal extract, antioxidant fruit extract and maple syrup. Traces of natural aroma are also present in each beverage. Formulations are 100% natural.

Formulation 1

This formulation described in Table 5 targets specifically the nervous system. Ingredients of this drink have been selected based on traditional uses reported in herbalism literature. Both scientific data and herbal medicine data provide evidence that this beverage may promote a relaxed state of the nervous system and the body in general. This beverage can be viewed as an anti-stress formula.

Formulation 2

This formulation described in Table 6 specifically targets the maintenance of cardiovascular functions. Ingredients of this drink have been selected based on traditional uses reported in herbalism literature. Both scientific data and herbal medicine data provide evidence that this beverage may have beneficial actions on the heart and blood vessel, helps in soothing nervous tension, and stimulates the immune system.

Formulation 3
Physiological Impact

This formulation described in Table 7 specifically targets women health. Ingredients of this drink have been selected based on traditional uses reported in herbalism literature. Both scientific data and herbal medicine data provide evidence that this beverage may have the ability to contribute to the wellness of women from puberty to post-menopause. Here is a literature review summarizing the herbalism and scientific review of the potential health benefits of the plants and fruits included in the beverage.

Formulation 4

This formulation described in Table 8 specifically targets the maintenance of a healthy digestive system. Ingredients of this drink have been selected based on traditional uses reported in herbalism literature. Both scientific data and herbal medicine data provide evidence that this beverage may have the ability to stimulate digestion and to help soothing digestive problems.

Results

Data presented in FIG. 1 shows that Formulation 1 and Formulation 4 developed by Applicant have the highest levels of polyphenols, followed by competitor 3. Formulation 2, formulation 3, and competitor 4 had comparable levels of polyphenols. Competitor 1 and 2 had low levels of polyphenols where as competitor 5 and competitor 6 had no significant levels of polyphenols. Values are expressed as mean mg/dose+/−SEM of n=6. Gallic acid was used to make the standard curve.

Figure 2:
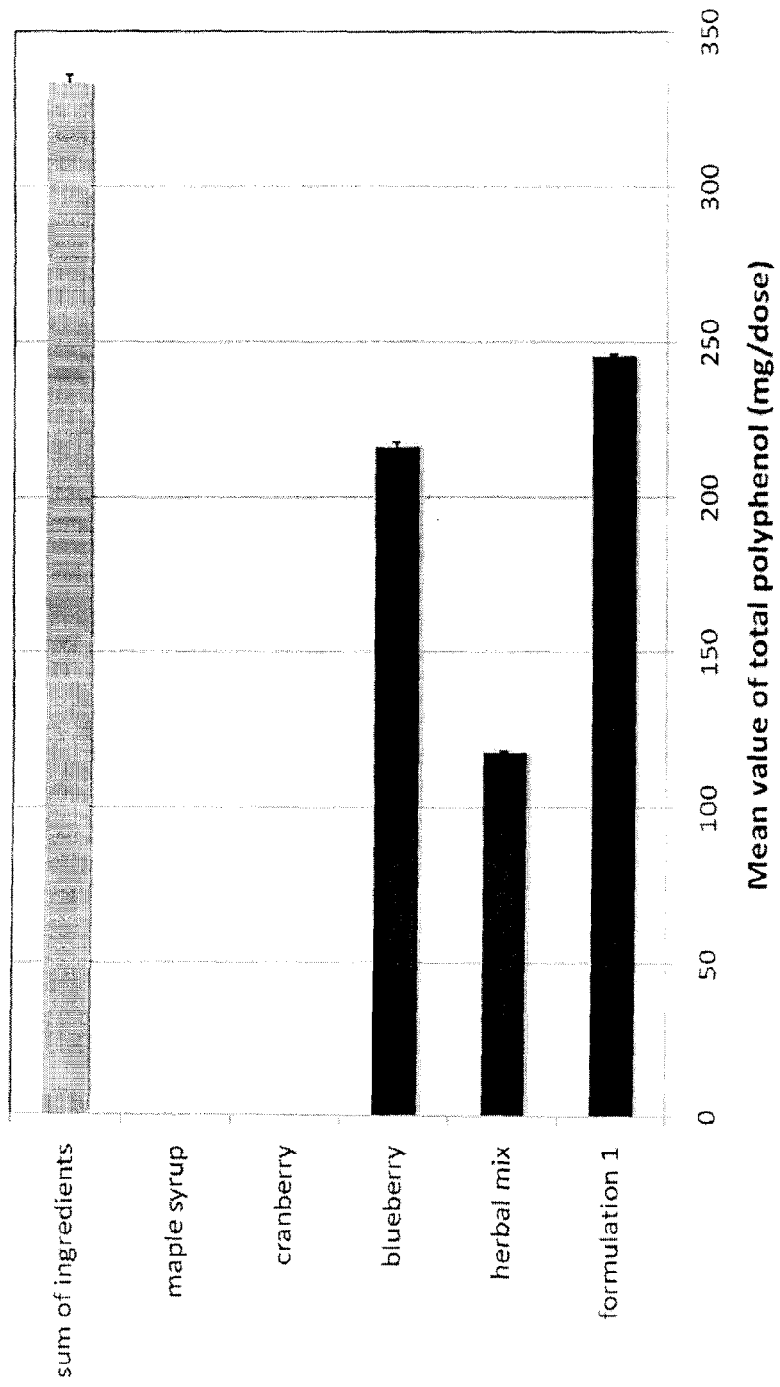
FIG. 2 shows levels of total polyphenols of each ingredient present in the amount used for one dose of formulation 1. Values are expressed as mean+/−SEM of n=3.
Figure 3:
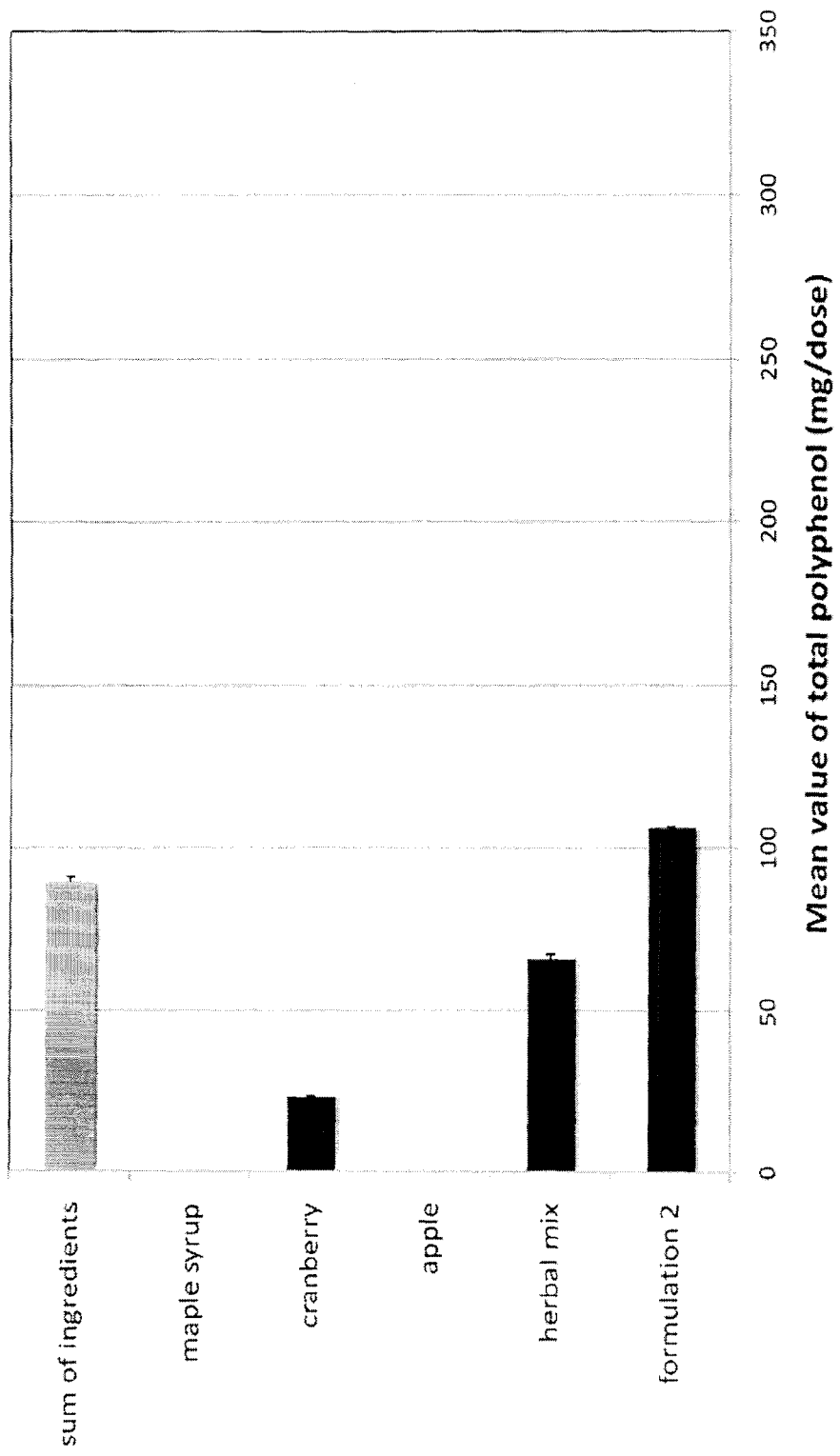
FIG. 3 shows levels of total polyphenols of each ingredient present in the amount used for one dose of formulation 2. Values are expressed as mean+/−SEM of n=3.
Figure 4:
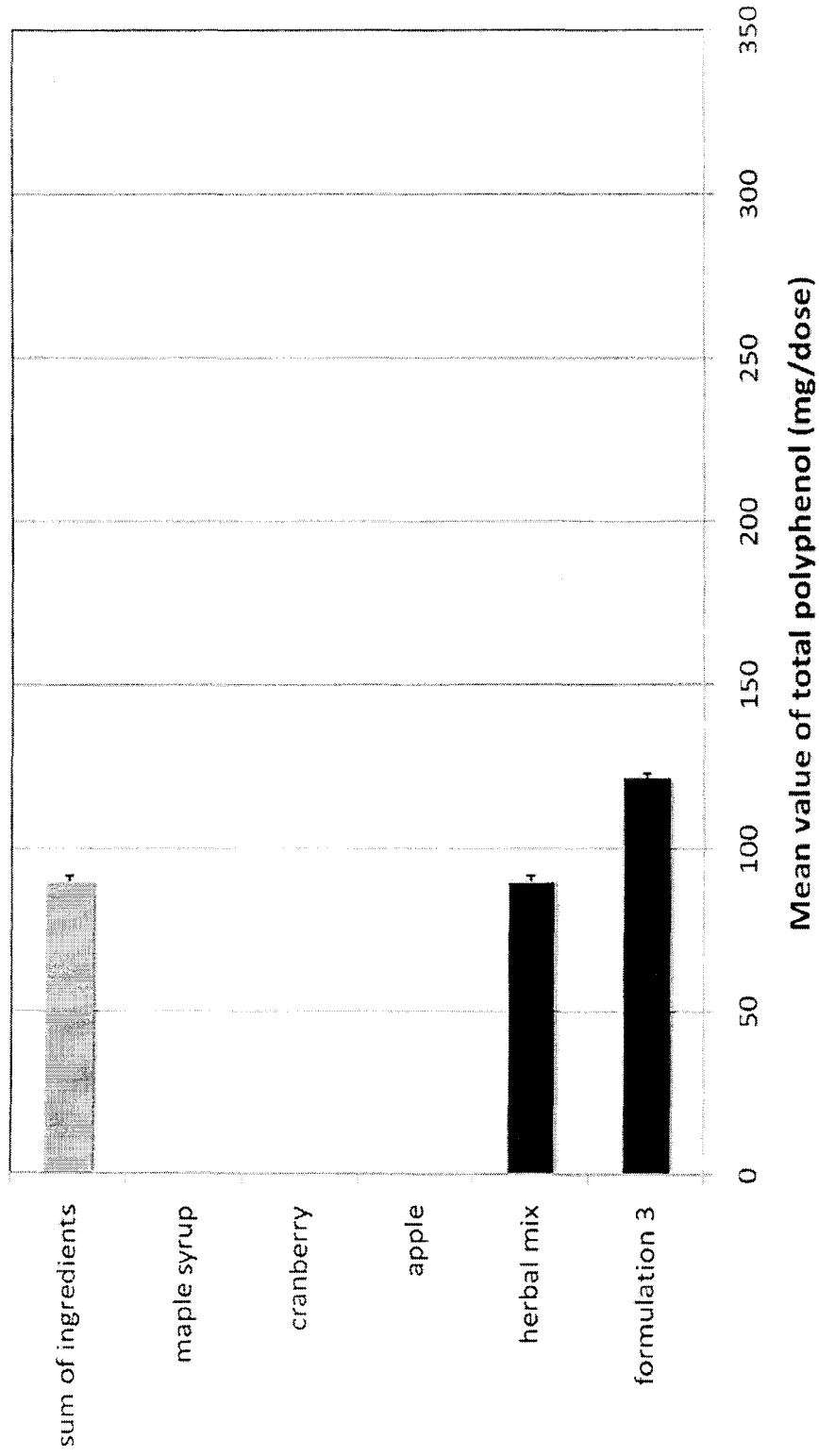
FIG. 4 shows levels of total polyphenols of each ingredient present in the amount used for one dose of formulation 3. Values are expressed as mean+/−SEM of n=3.
Figure 5:
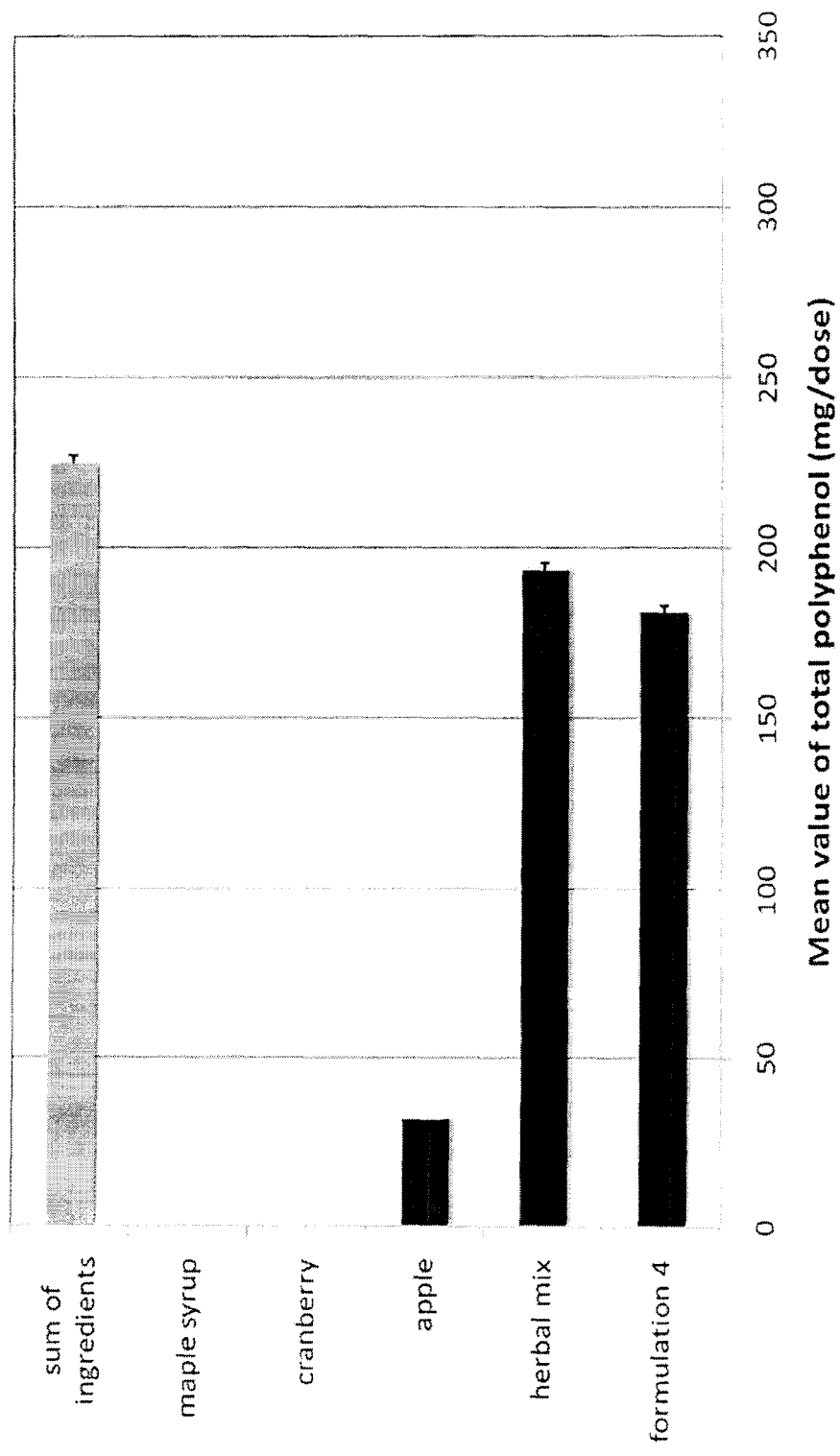
FIG. 5 shows levels of total polyphenols of each ingredient present in the amount used for one dose of formulation 4. Values are expressed as mean+/−SEM of n=3.

FIG. 2 shows that the herbal mix and blueberry concentrate of formulation 1 contained significant levels of polyphenols, whereas maple syrup and cranberry concentrate did not. FIG. 3 shows that maple syrup and apple concentrate of formulation 2 do not contain significant levels of polyphenols. FIG. 4 shows levels of total polyphenols of each ingredient present in the amount used for one dose of formulation 3. FIG. 5 shows levels of total polyphenols of each ingredient present in the amount used for one dose of formulation 4. The herbal mix and apple concentrate contained significant levels of polyphenols, whereas maple syrup and cranberry concentrate did not. For each of the formulations presented in FIGS. 2-5, the ingredients, when combined together, do not cause the formation of additional polyphenols since the amount of polyphenols present in formulation 1 is not greater than the sum of ingredients.

Figure 6:
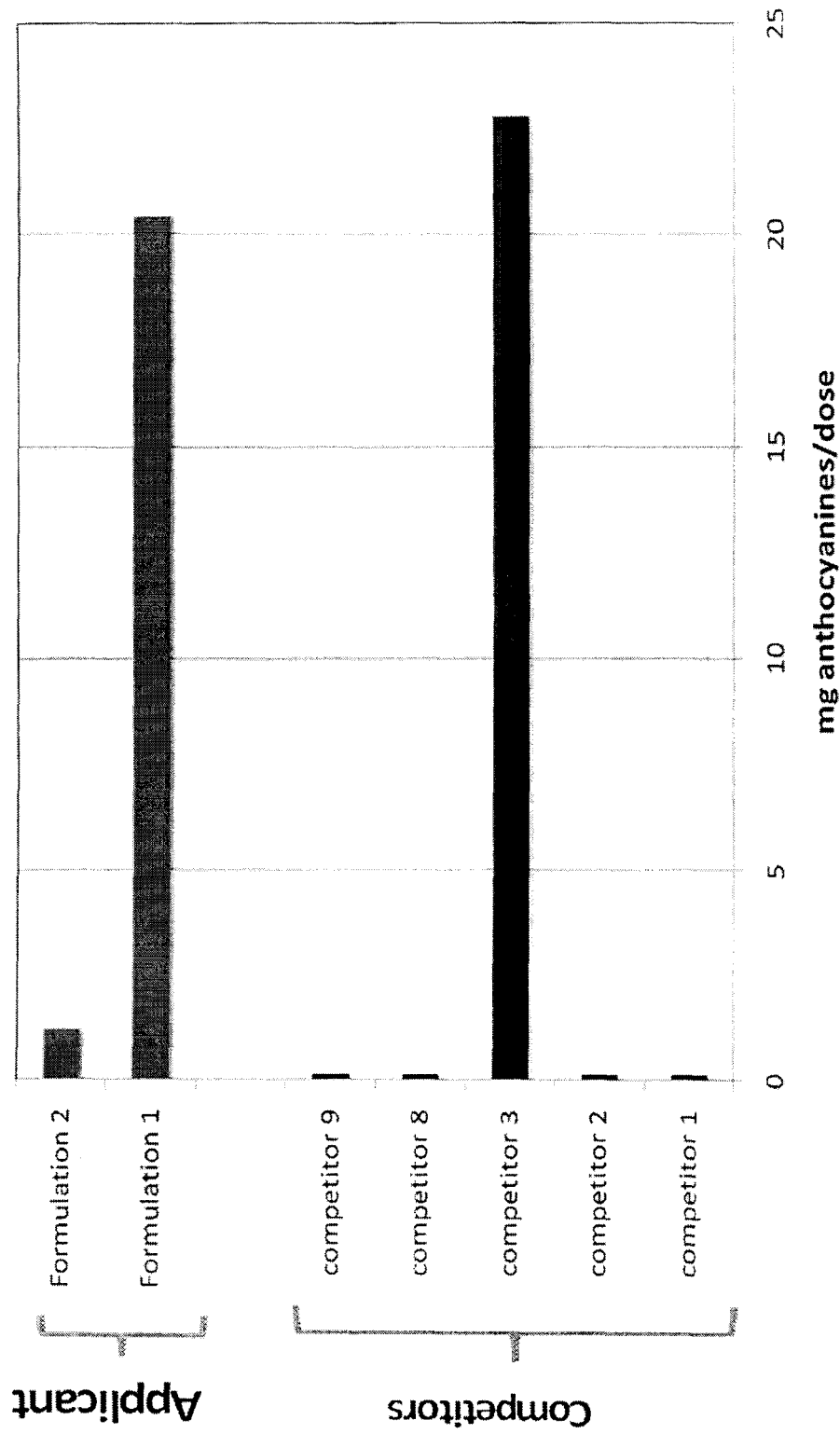
FIG. 6 shows the amount of anthocyanins per dose present in various formulations.

FIG. 6 shows the amount of anthocyanins per dose present in various formulations. Formulation 1 developed by Applicant and competitor 3 had the highest levels of anthocyanins. Formulation 2 had low, but detectable levels of anthocyanins.

Figure 7:
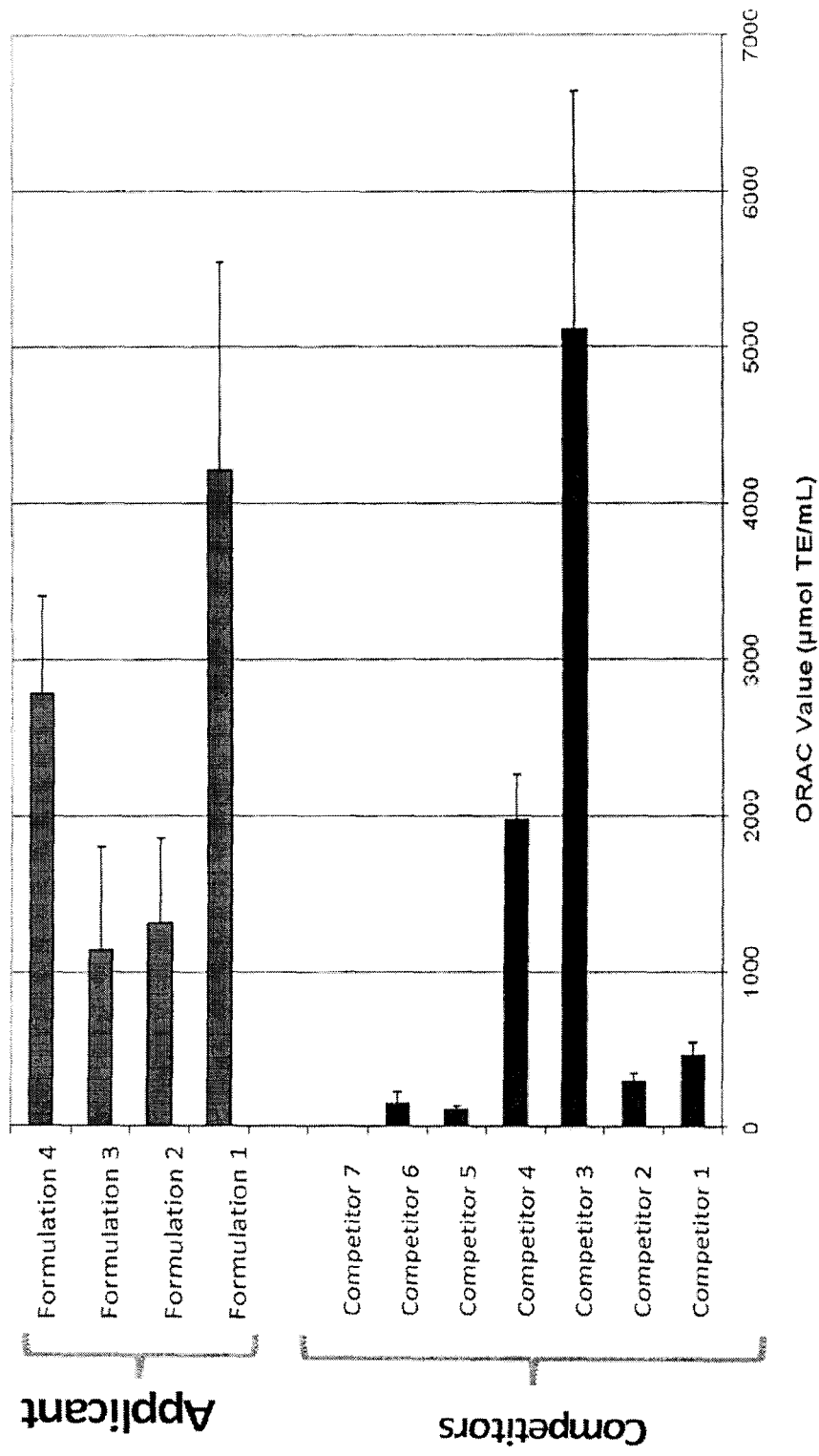
FIG. 7 shows that functional beverages developed by Applicant have high anti-oxidant chemical capacity when compared to various competitors as shown by oxygen-radical-antioxidant capacity (ORAC) value. ORAC values (mean±SD of 3 independent experiments) are expressed as μmol Trolox equivalent (TE)/ml.
Figure 8:
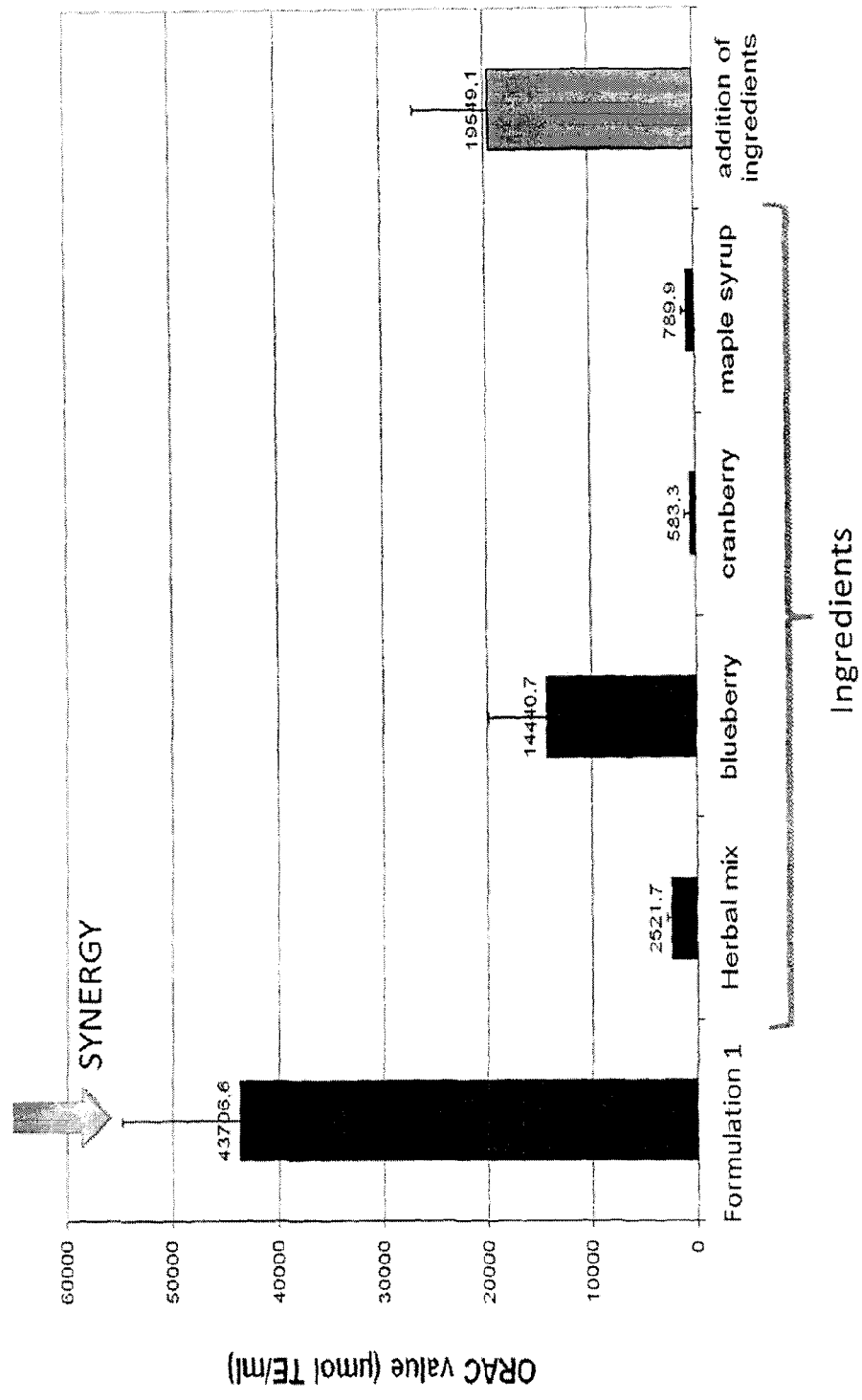
FIG. 8 shows the synergistic effect of ingredients of Formulation 1 to enhance the antioxidant potential of beverages as shown by ORAC value. ORAC values (mean±SD of 3 independent experiments) are expressed as μmol Trolox equivalent (TE)/ml.
Figure 9:
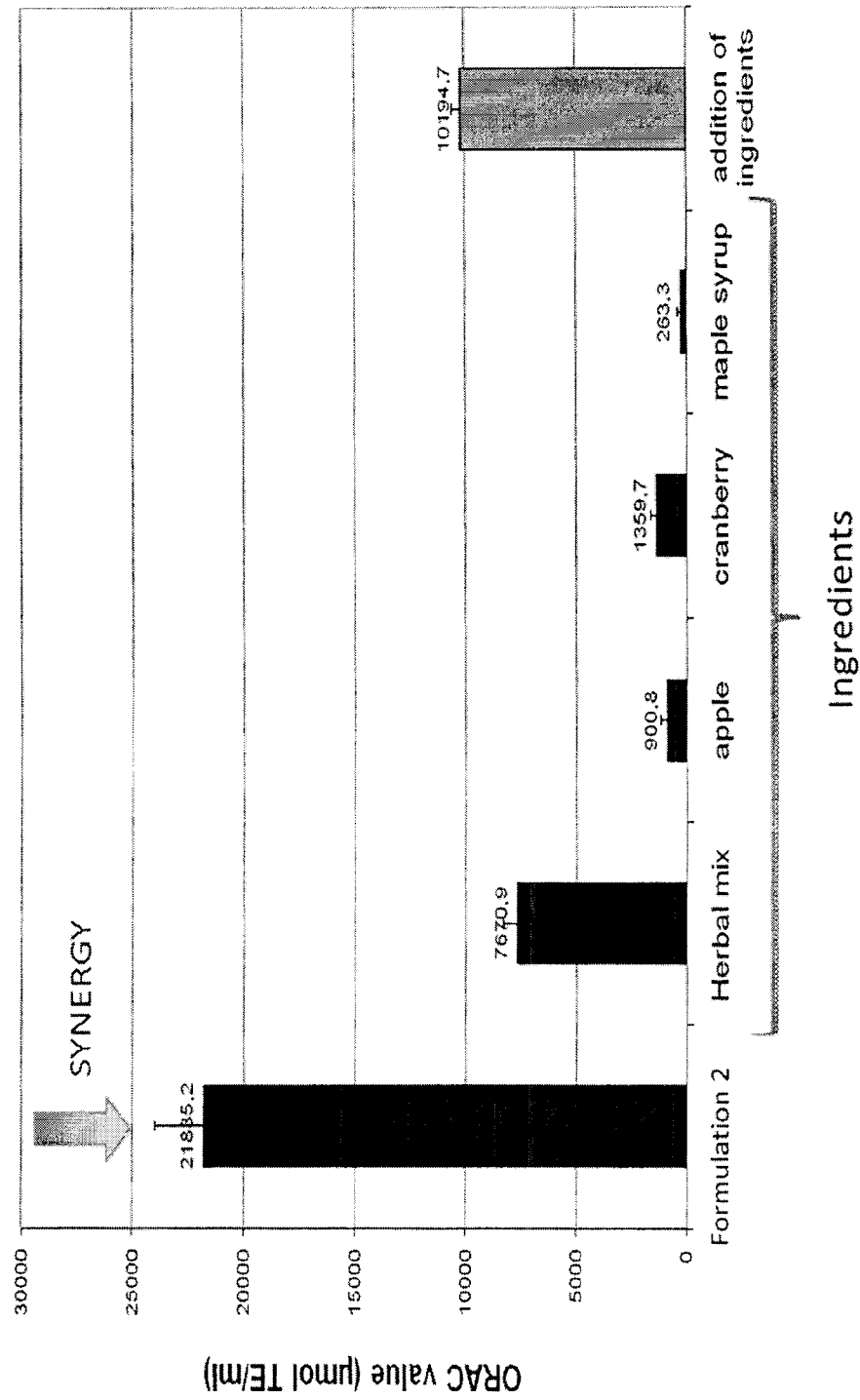
FIG. 9 shows the synergistic effect of ingredients of Formulation 2 to enhance the antioxidant potential of beverages as shown by ORAC value. ORAC values (mean±SD of 3 independent experiments) are expressed as μmol Trolox equivalent (TE)/ml.
Figure 10:
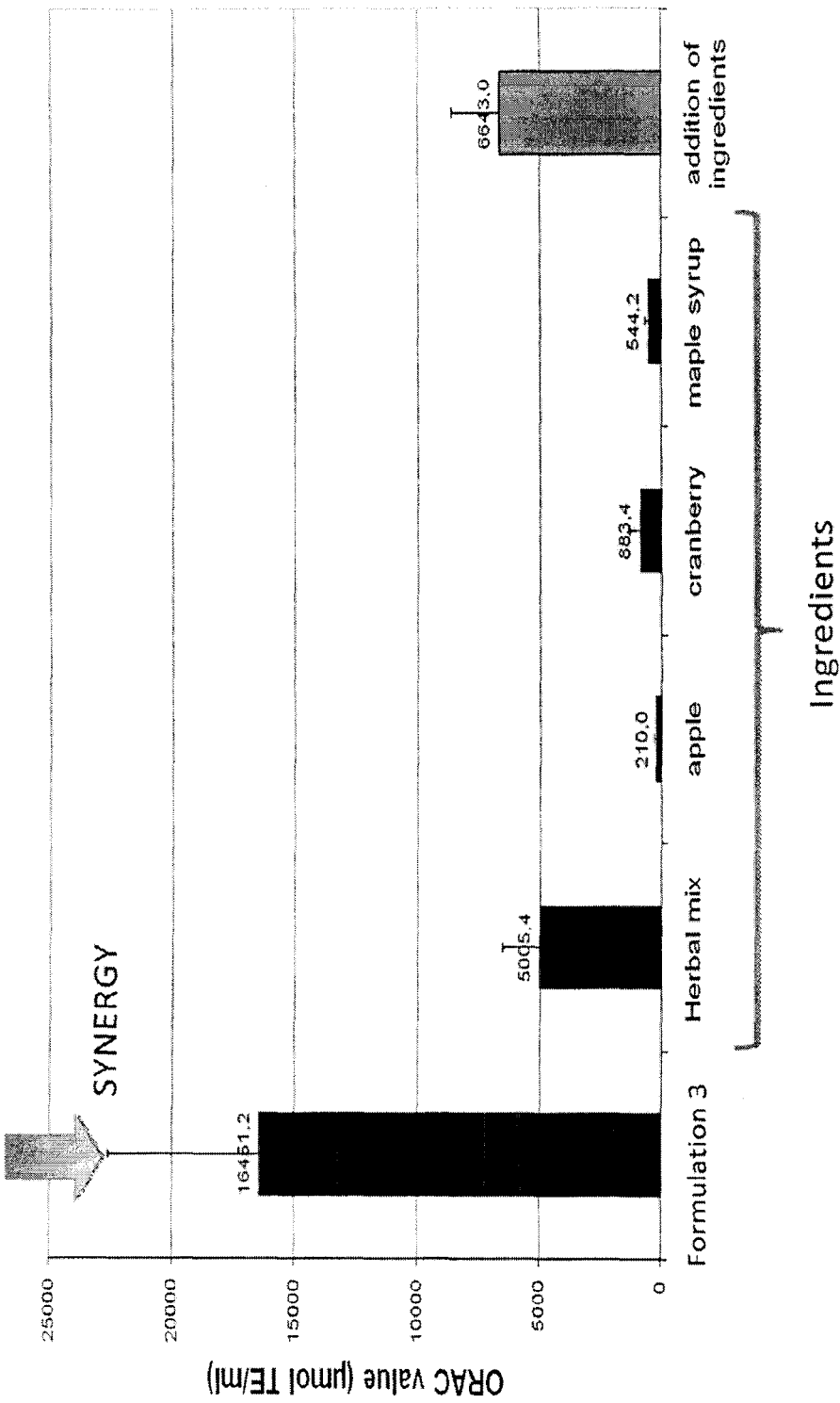
FIG. 10 shows the synergistic effect of ingredients of Formulation 3 to enhance the antioxidant potential of beverages as shown by ORAC value. ORAC values (mean±SD of 3 independent experiments) are expressed as μmol Trolox equivalent (TE)/ml.
Figure 11:
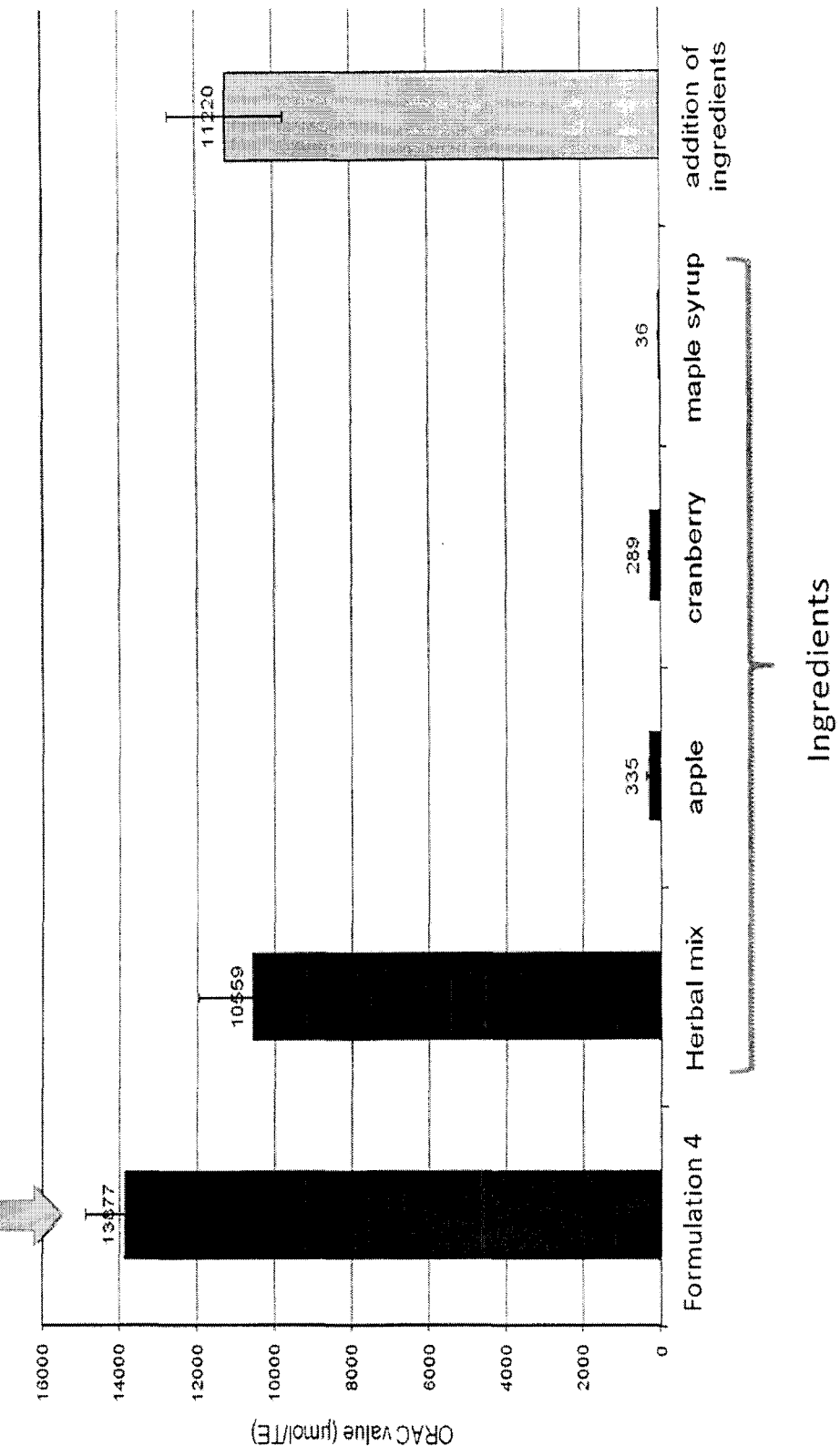
FIG. 11 shows the synergistic effect of ingredients of Formulation 4 to enhance the antioxidant potential of beverages as shown by ORAC value. ORAC values (mean±SD of 3 independent experiments) are expressed as μmol Trolox equivalent (TE)/ml.

FIG. 7 shows that functional beverages developed by Applicant have high anti-oxidant chemical capacity when compared to various competitors as shown by oxygen-radical-antioxidant capacity (ORAC) value. Formulation 1, formulation 4 and competitor 3 have the highest antioxidant potential compared to the other formulations tested. Formulation 2, formulation 3 and competitor 4 have high antioxydant potential, whereas competitors 1, 2, 5, 6 and 7 had low to undetectable antioxydant potentials. Interestingly, the ORAC profile was comparable to that of the polyphenol profile (FIG. 1), suggesting that polyphenols are mainly responsible for this property.

FIGS. 8, 9, 10 and 11 show the synergistic effect of ingredients of Formulations 1, 2, 3 and 4 respectively to enhance the antioxidant potential of beverages as shown by ORAC value.

Figure 12:
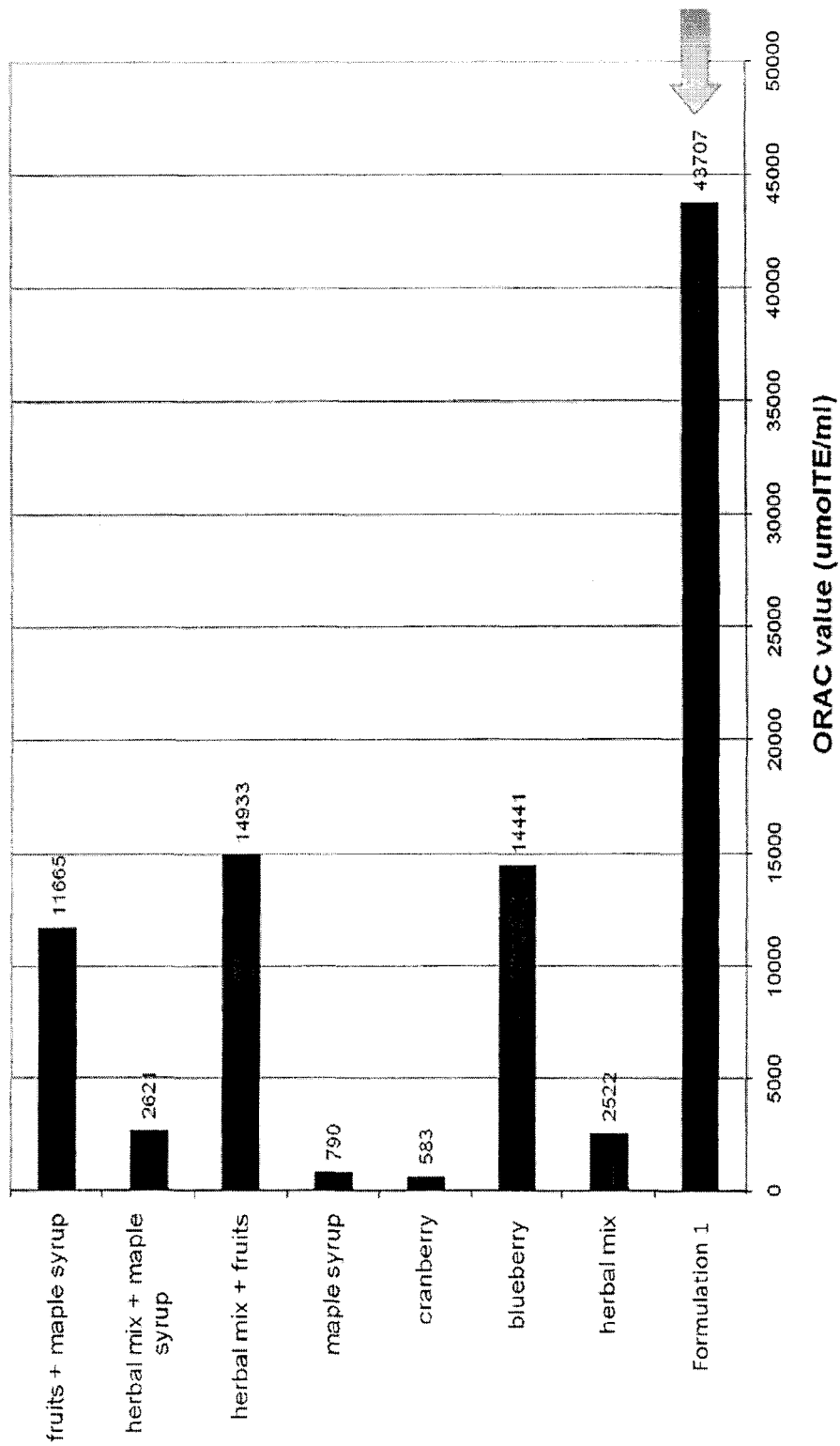
FIG. 12 shows that the combination of three types of ingredients (herbal extract, fruit extract and maple syrup) provides the synergistic effect of Formulation 1. ORAC values are representative of two separate experiments and are expressed as μmol Trolox equivalent (TE)/ml.
Figure 13:
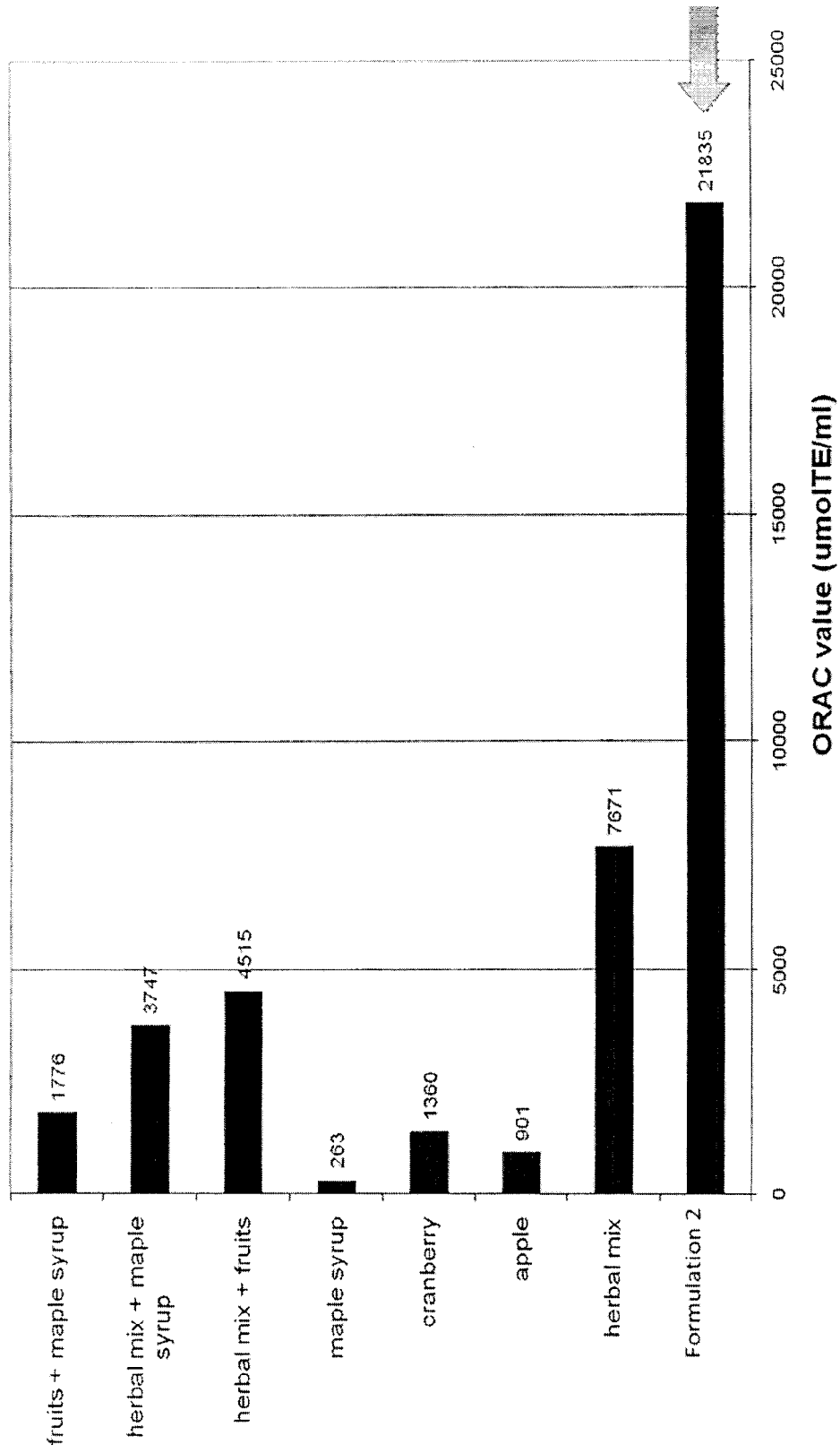
FIG. 13 shows that the combination of three types of ingredients (herbal extract, fruit extract and maple syrup) provides the synergistic effect of Formulation 2. ORAC values are representative of two separate experiments and are expressed as μmol Trolox equivalent (TE)/ml.

FIGS. 12 and 13 show that the combination of three types of ingredients (herbal extract, fruit extract and maple syrup) provides the synergistic effect of Formulations 1 and 2 respectively.

Figure 14:
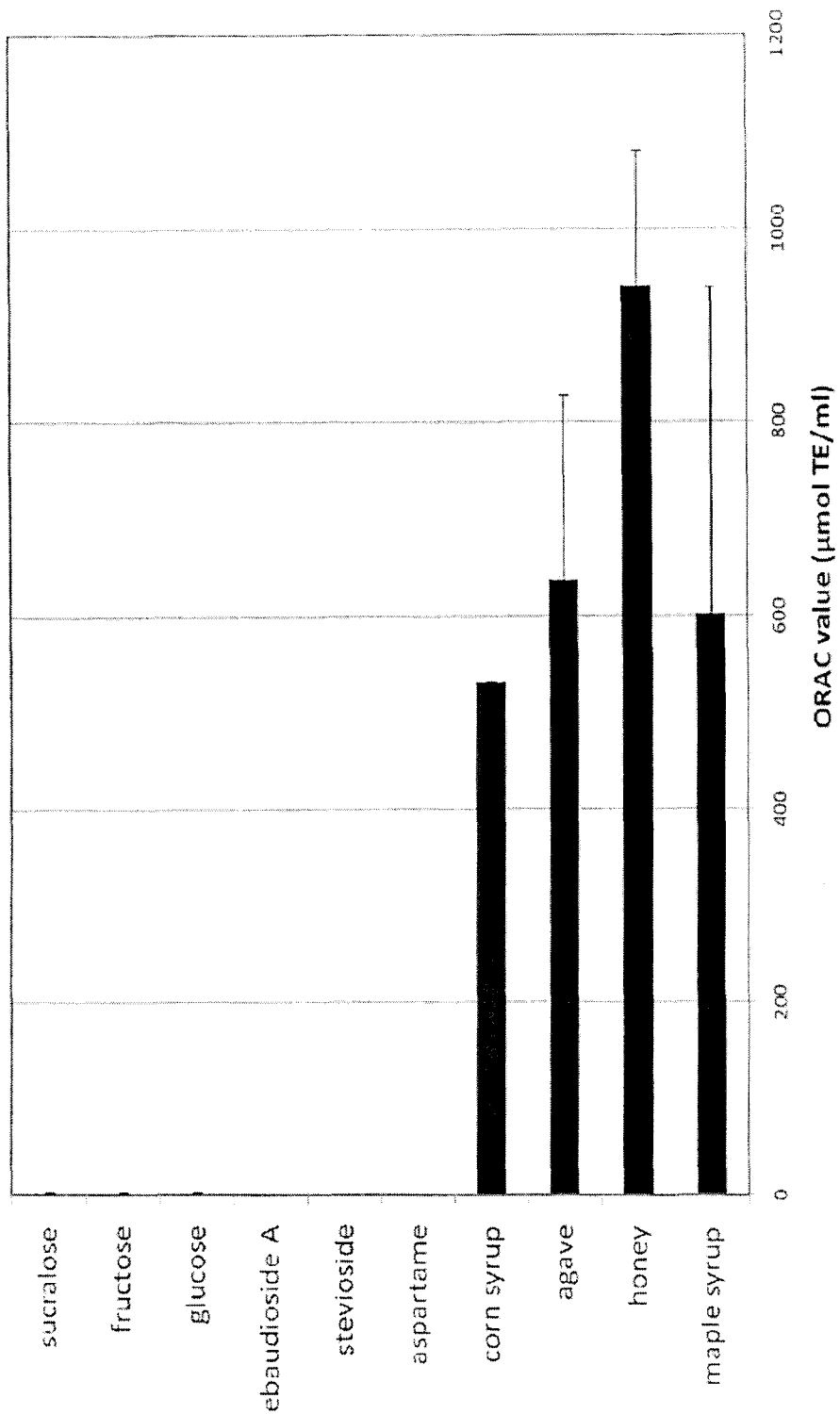
FIG. 14 shows the antioxidant potential of sweeteners at the same molarity as shown by their ORAC value. ORAC values (n=5) were normalized to the respective sweetening power of each sweetener, and are expressed as μmol Trolox equivalent (TE)/ml.

FIG. 14 shows the antioxidant potential of different sweeteners when assessed at the same molarity [0.2M] as shown by their ORAC value. The nutritive natural sweeteners with antioxidant properties include maple syrup, agave, honey and cord syrup. Given this data, formulations developed by Applicant could be composed of any of these 4 antioxidant sweeteners.

Figure 15:
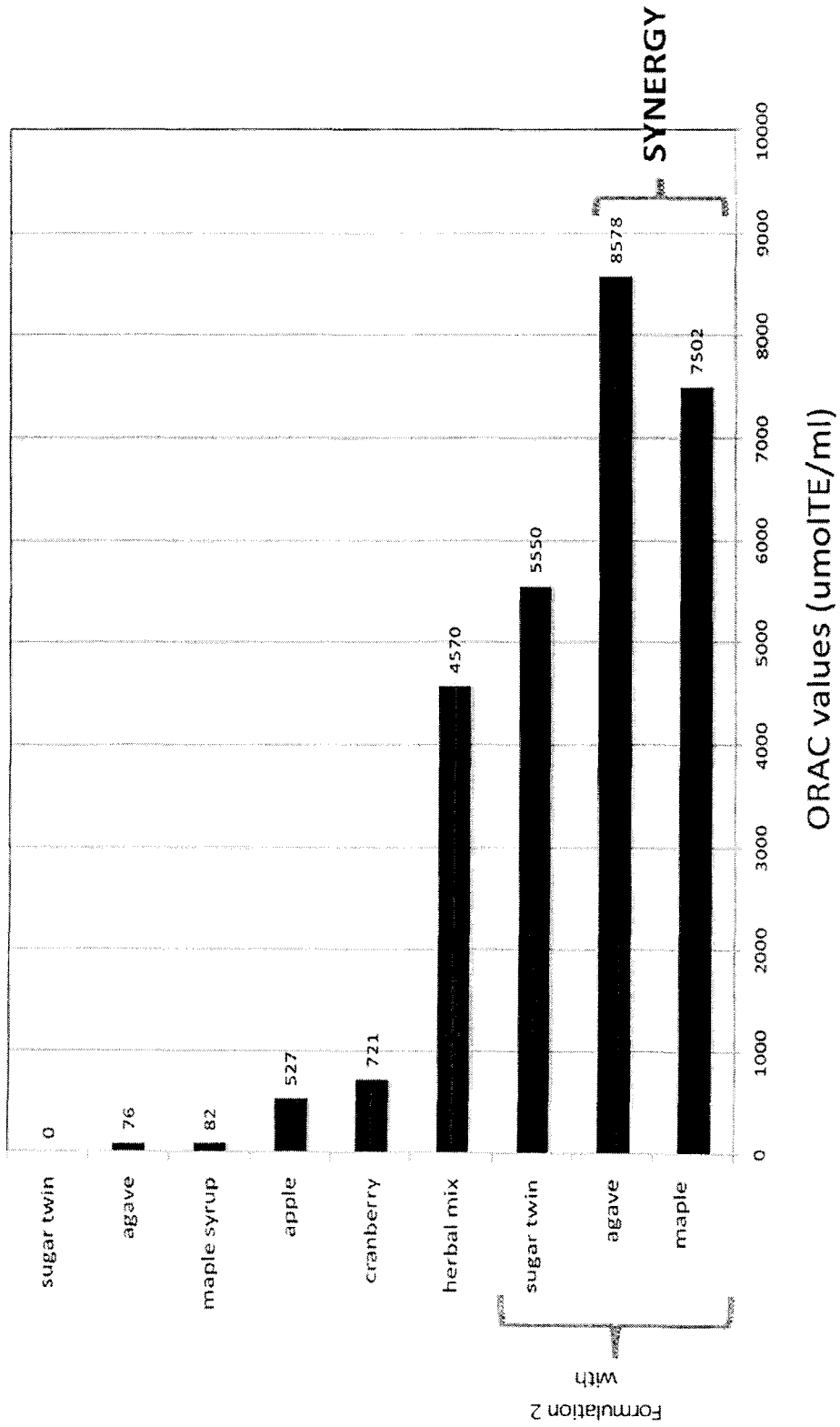
FIG. 15 shows that agave, another natural sweetener with antioxidant property, can also produce synergy when formulated with the herbal and fruit extracts. ORAC values are expressed as μmol Trolox equivalent (TE)/ml.

FIG. 15 shows that agave, another natural sweetener with antioxidant property, can also produce synergy when formulated with the herbal and fruit extracts.

Figure 16:
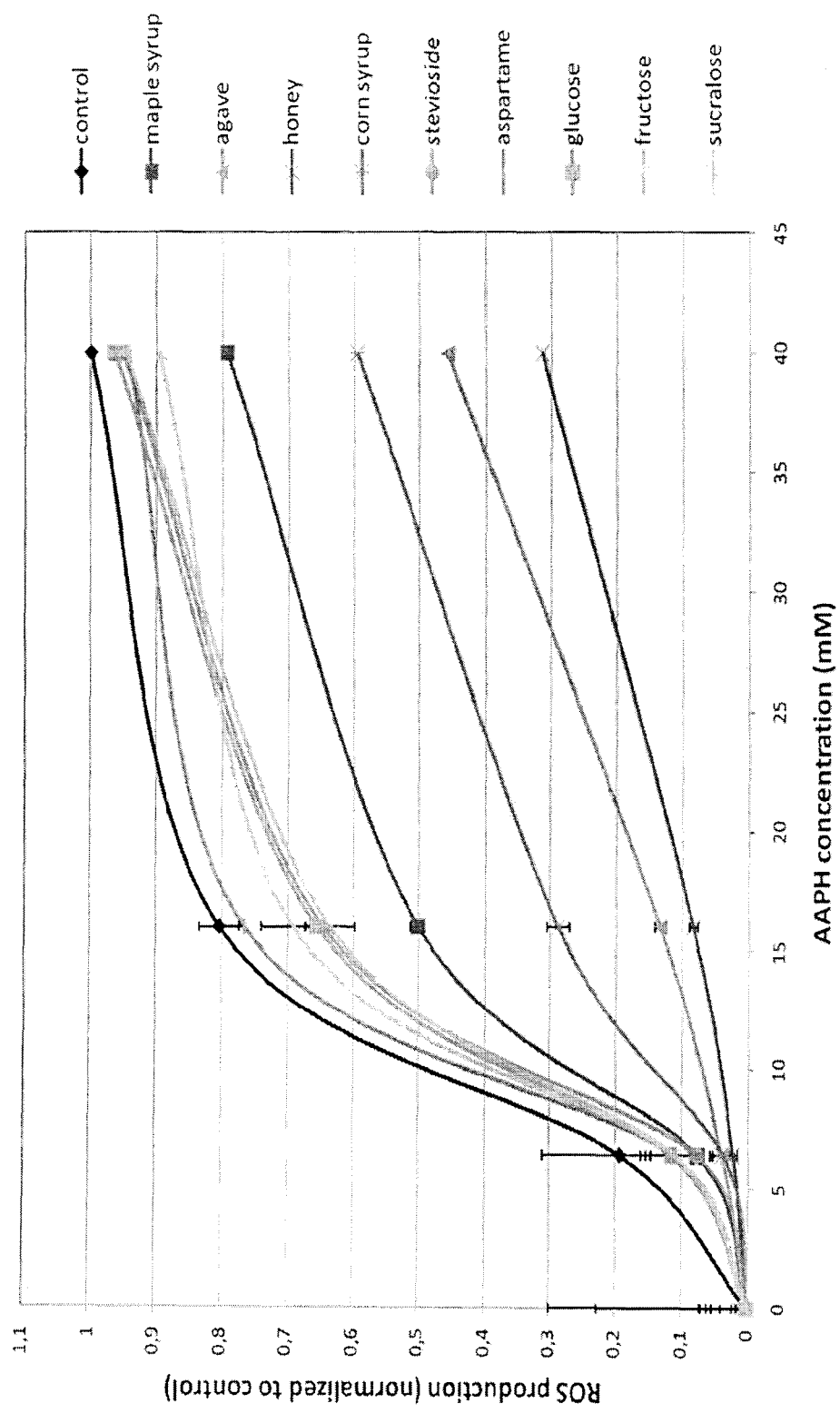
FIG. 16 shows the anti-ROS potential in tongue epithelial cells of sweeteners at the same molarity. Values obtained from 3 separate experiments were normalized to the respective sweetening power of each sweetener tested and are expressed as Relative Fluorescence Unit (RFU).

FIG. 16 shows the anti-ROS potential in tongue epithelial cells of sweeteners when assessed at the same molarity [0.2M]. Data show that honey, agave, maple syrup and corn syrup have high biochemical antioxidant potential when compared to other sweeteners as shown by a reduction in ROS levels after 60 minutes exposed to various concentrations of AAPH. This data suggests the use of sweeteners with high antioxidant potential could be used in the formulations proposed.

Figure 17:
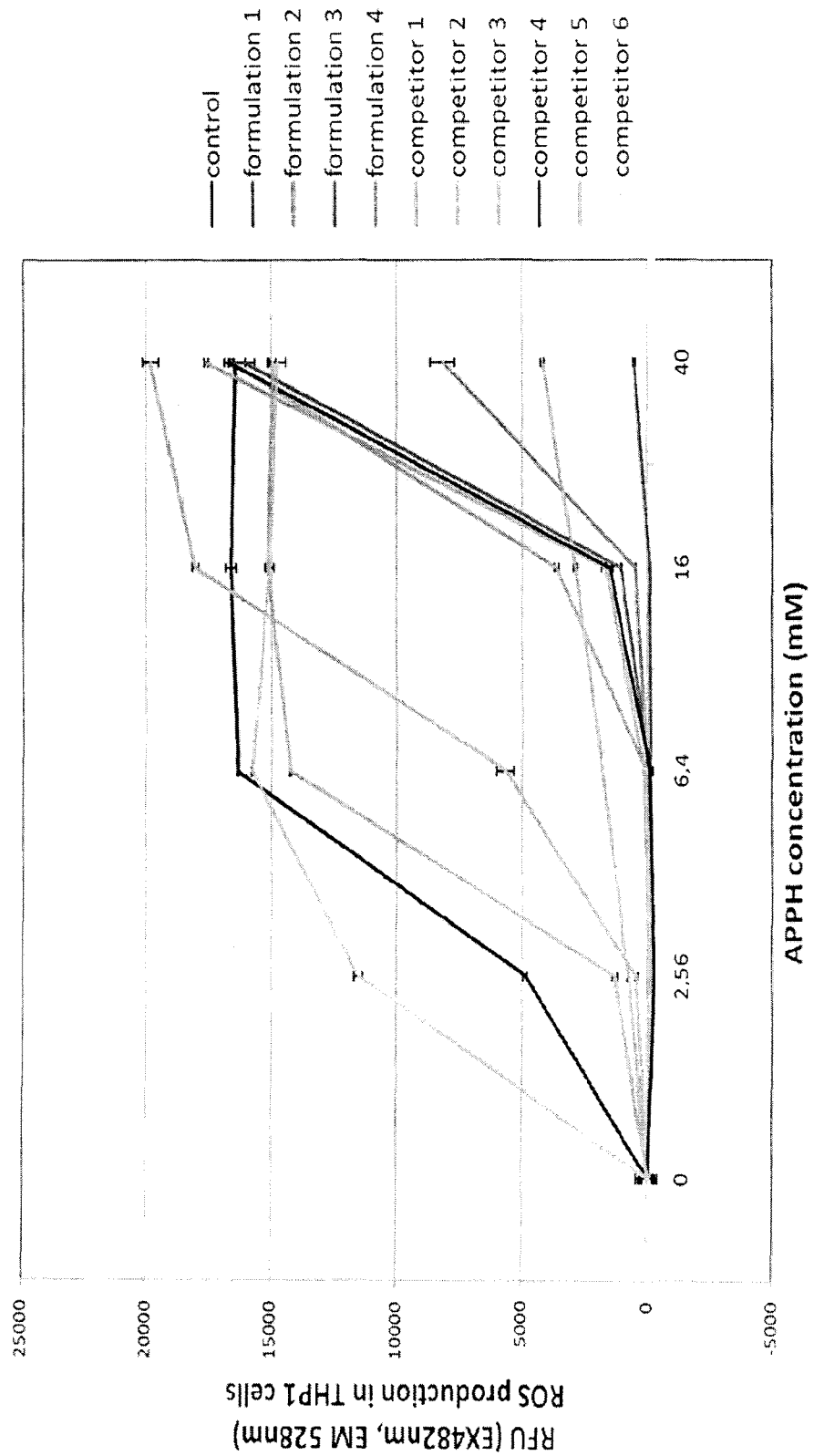
FIG. 17 shows that formulations, used as functional beverages, developed by Applicant have higher antioxidant biochemical potential than most competitors. Values of ROS production are expressed as mean+/−SEM of Relative Fluorescence Unit for n=3.

FIG. 17 shows that formulations, used as functional beverages, developed by Applicant have higher antioxidant biochemical potential than most competitors, except for competitor 1, 3 and 4, as shown by a reduction in ROS production after 120 minutes in THP1 cells in suspension using various concentrations of ROS inducer AAPH. Formulation 1 had the highest antioxidant potential. Since whole formulations never come in contact with monocytic cells, THP-1 cells were only used as model of ROS production.

Figure 18:
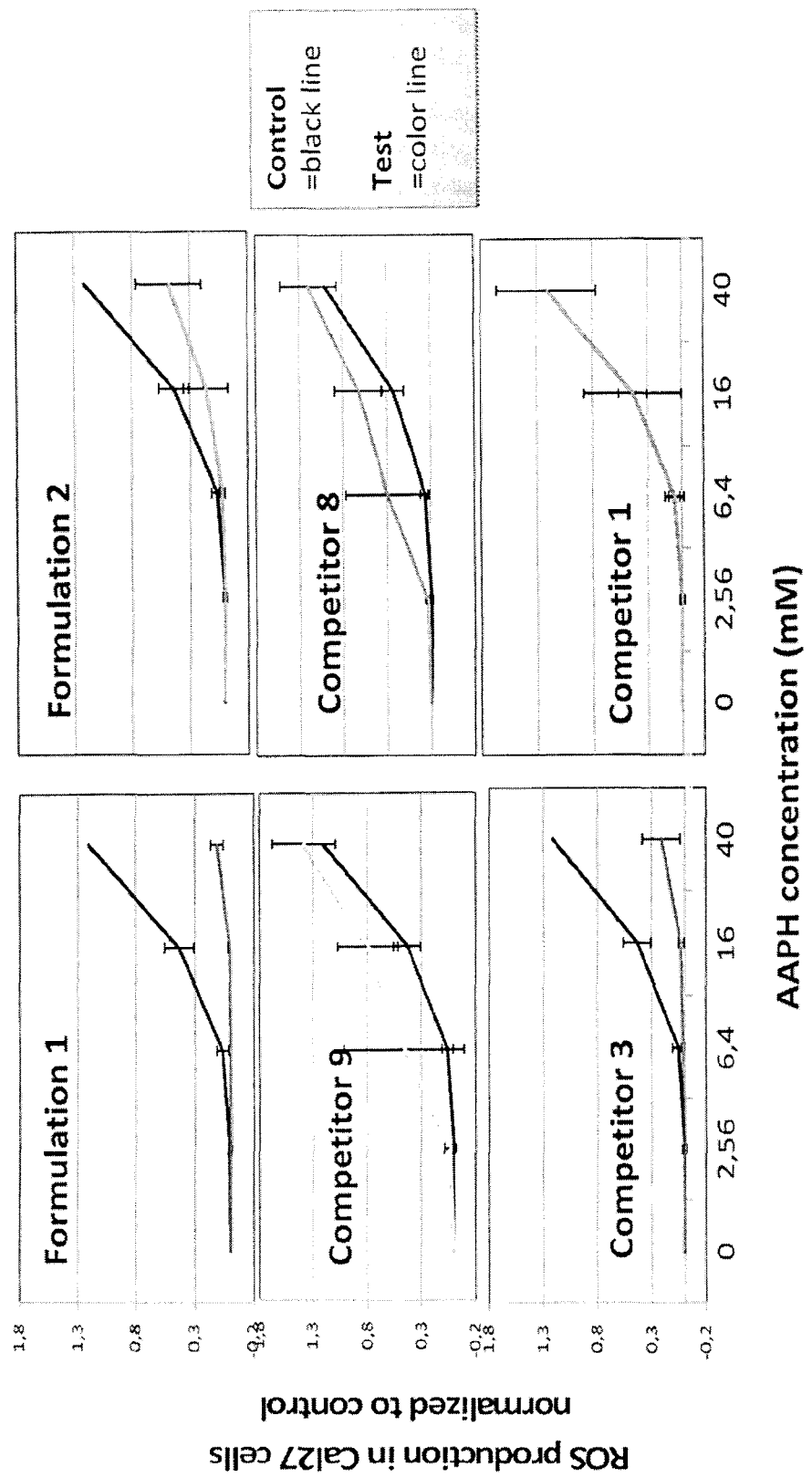
FIG. 18 shows that formulations, used as functional beverages, developed by Applicant have high antioxidant biochemical potential compared to competitors products as shown by a reduction in ROS production in Cal27 cells. Values of ROS production were normalized to control (40AAPH in cells not exposed HBSS). This data are expressed as mean+/−SEM of n=3.

FIG. 18 shows that formulations, used as functional beverages, developed by Applicant have high antioxidant biochemical potential compared to competitors products as shown by a reduction in ROS production in Cal27 cells using various concentrations of AAPH. Of all formulations tested, formulation 1 was the best formulation at inhibiting ROS production in oral mucosal cells. HBSS buffer, used as sample diluent, was used as control.

Figure 19:
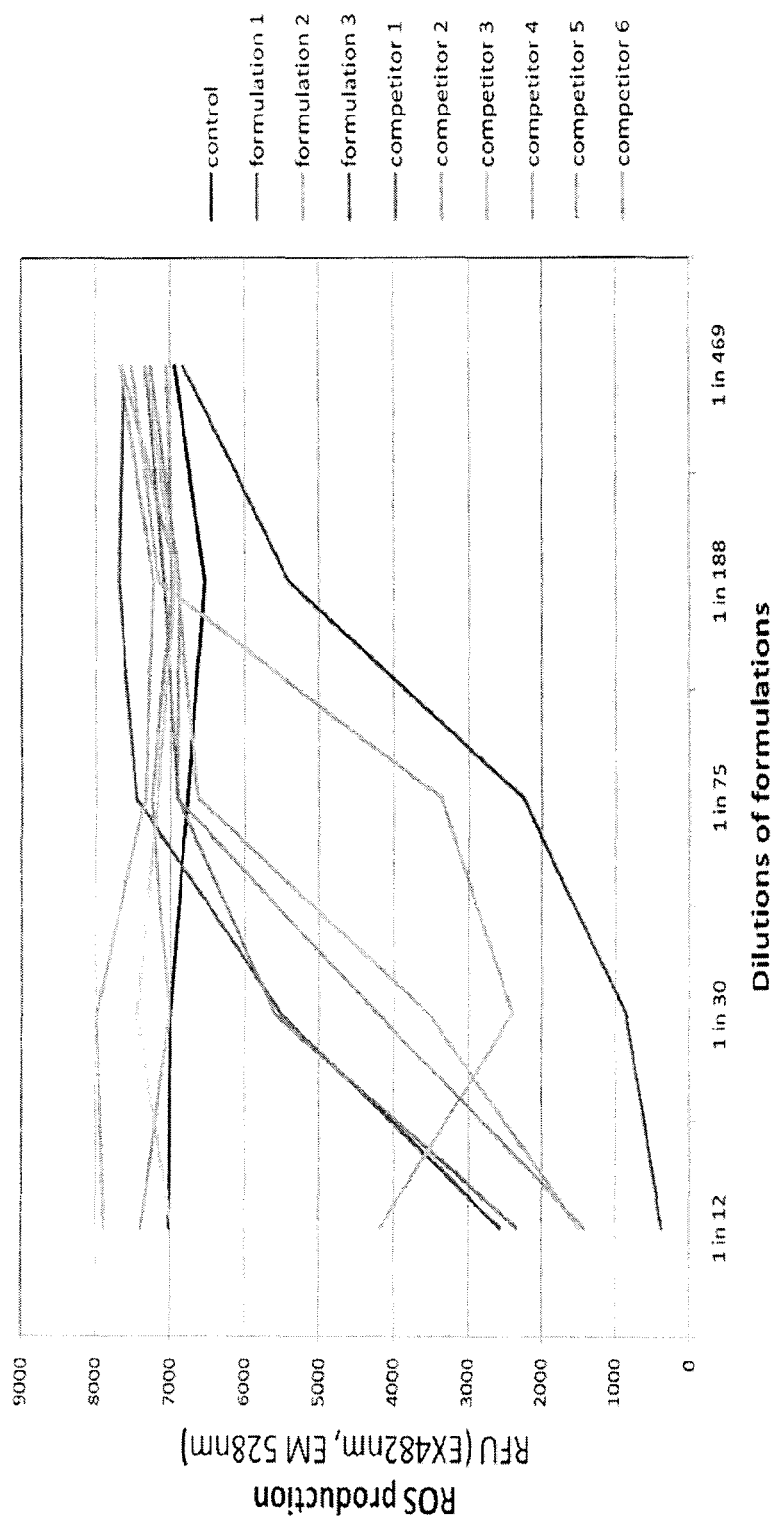
FIG. 19 shows the antioxidant potential of functional beverages developed by Applicant. Values are representative of two separate experiments, and ROS production is expressed as Relative Fluorescence Unit (RFU).

FIG. 19 shows the antioxidant potential that functional beverages developed by Applicant, formulations 1, 3, and 2 have high antioxidant biochemical potential when compared to competitors as shown by a reduction in ROS production induced with a sus-maximal dose of AAPH (40 mM) in THP-1 cells in suspension (30 minutes). Since whole formulations never come in contact with monocytic cells, THP-1 cells were only used as model of ROS production. Thus, results obtained from this assay should be considered physiologically relevant. Of all formulations tested, formulation 1 has the highest anti-ROS activity. Various concentrations of samples were tested with a fixed dose of AAPH.

Figure 20:
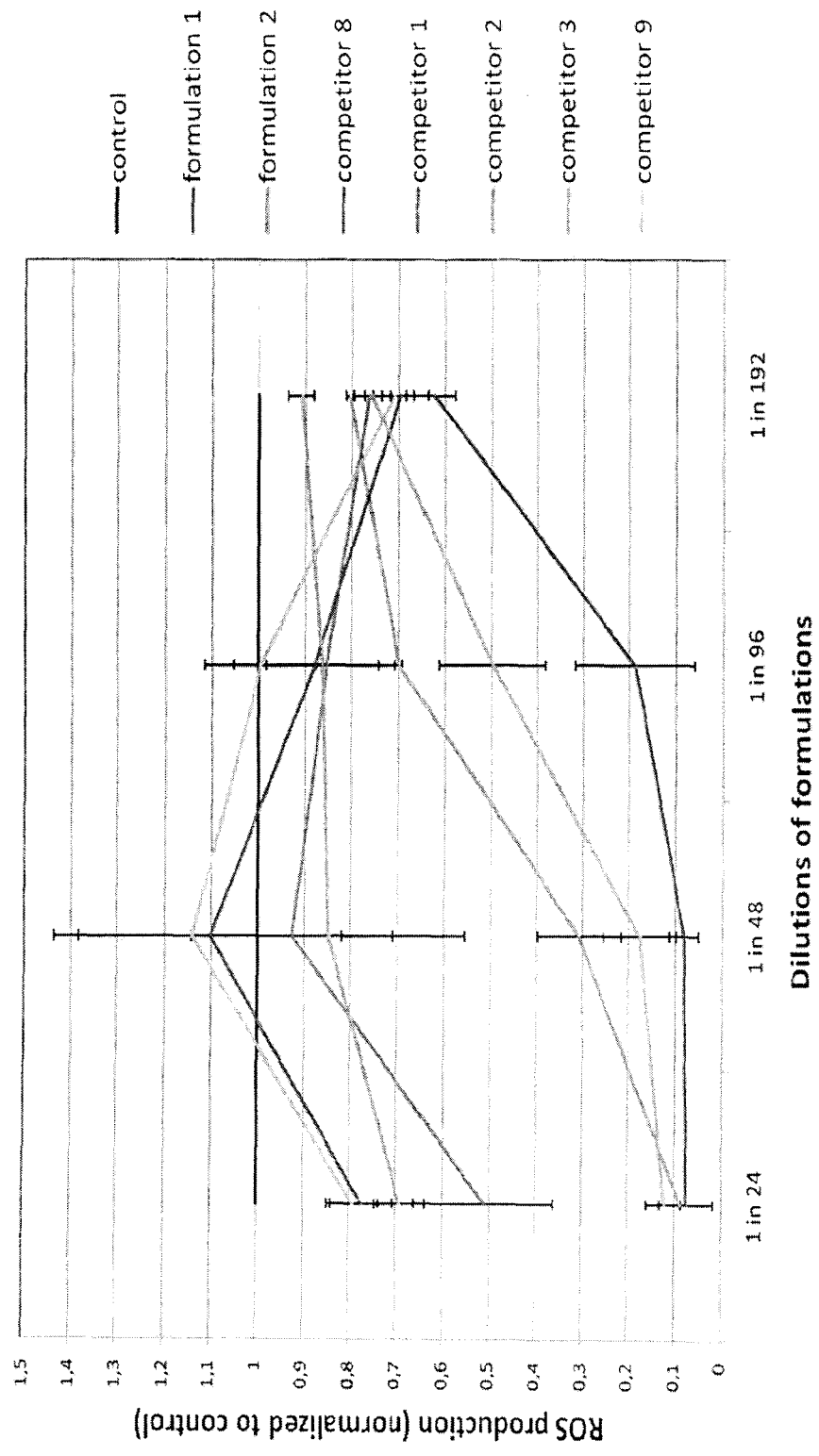
FIG. 20 shows the anti-ROS activity of various dilutions of functional beverages developed by Applicant and competitors in tongue epithelial cells (Cal27). Values normalized to control are mean+/−SEM of minimum n=3.

FIG. 20 shows the anti-ROS activity of various dilutions of functional beverages developed by Applicant and competitors in tongue epithelial cells (Cal27). Since whole formulations never come in contact with oral epithelium, results from this assay are applicable physiologically. Data show that formulations 1 has the highest antioxidant potential when compared to all other formulations tested, including the 4 competitors, as shown by a reduction in ROS production induced with a high dose of AAPH (40 mM) for 60 minutes in Cal27 cells.

Figure 21:
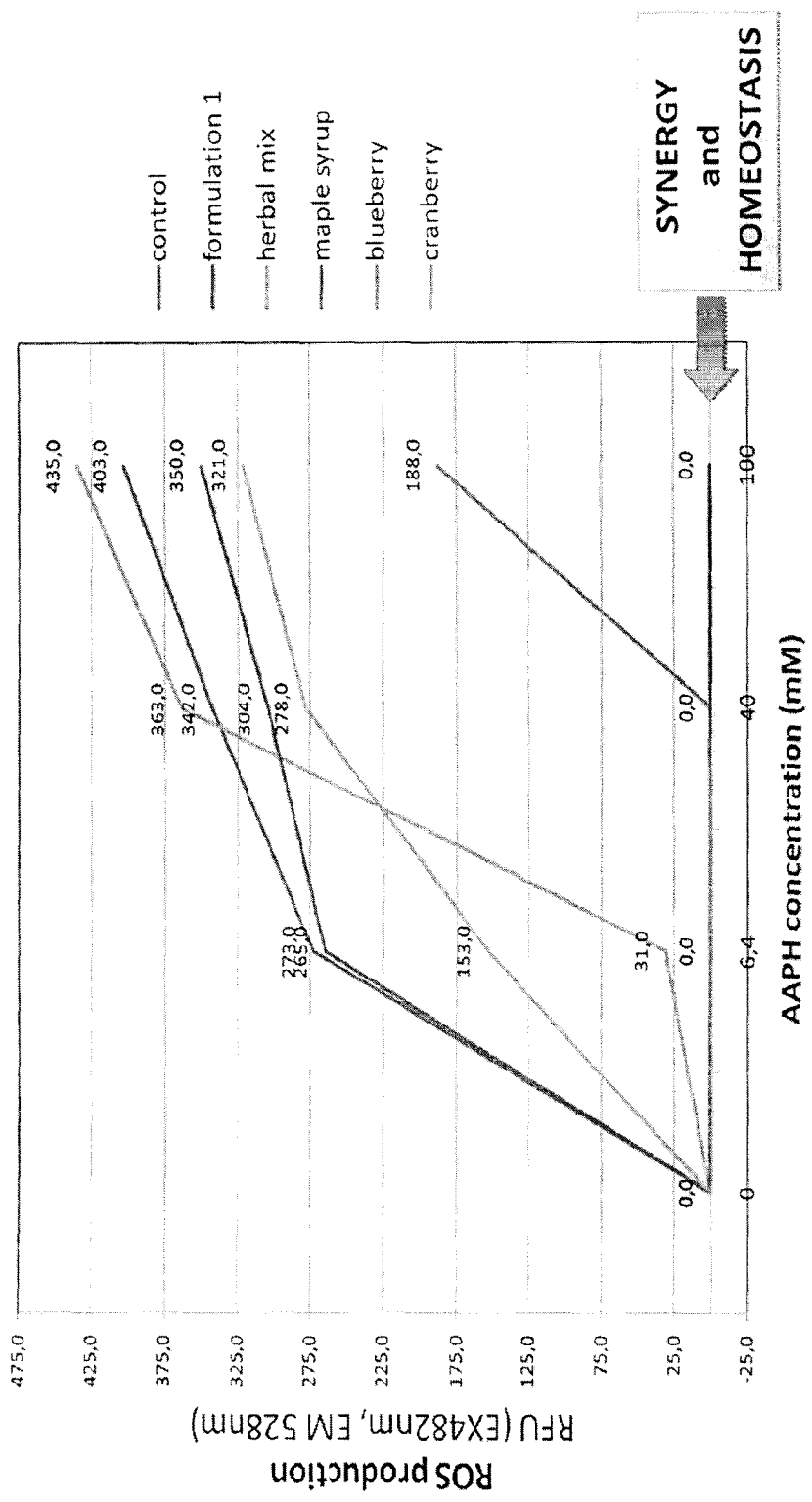
FIG. 21 shows that ingredients of Formulation 1 act in synergy to modulate ROS production artificially induced by AAPH in tongue epithelial CAL27 cells treated for up to 120 minutes. Values are representative of two separate experiments, and ROS production is expressed as Relative Fluorescence Unit (RFU).

FIG. 21 shows that ingredients of Formulation 1 act in synergy to modulate ROS production artificially induced by AAPH in tongue epithelial CAL27 cells treated for up to 120 minutes. Ingredients act in synergy to promote homeostasis by maintaining non-damaging levels of ROS, this effect can last more than 2 hours after mucosal exposure.

Figure 22:
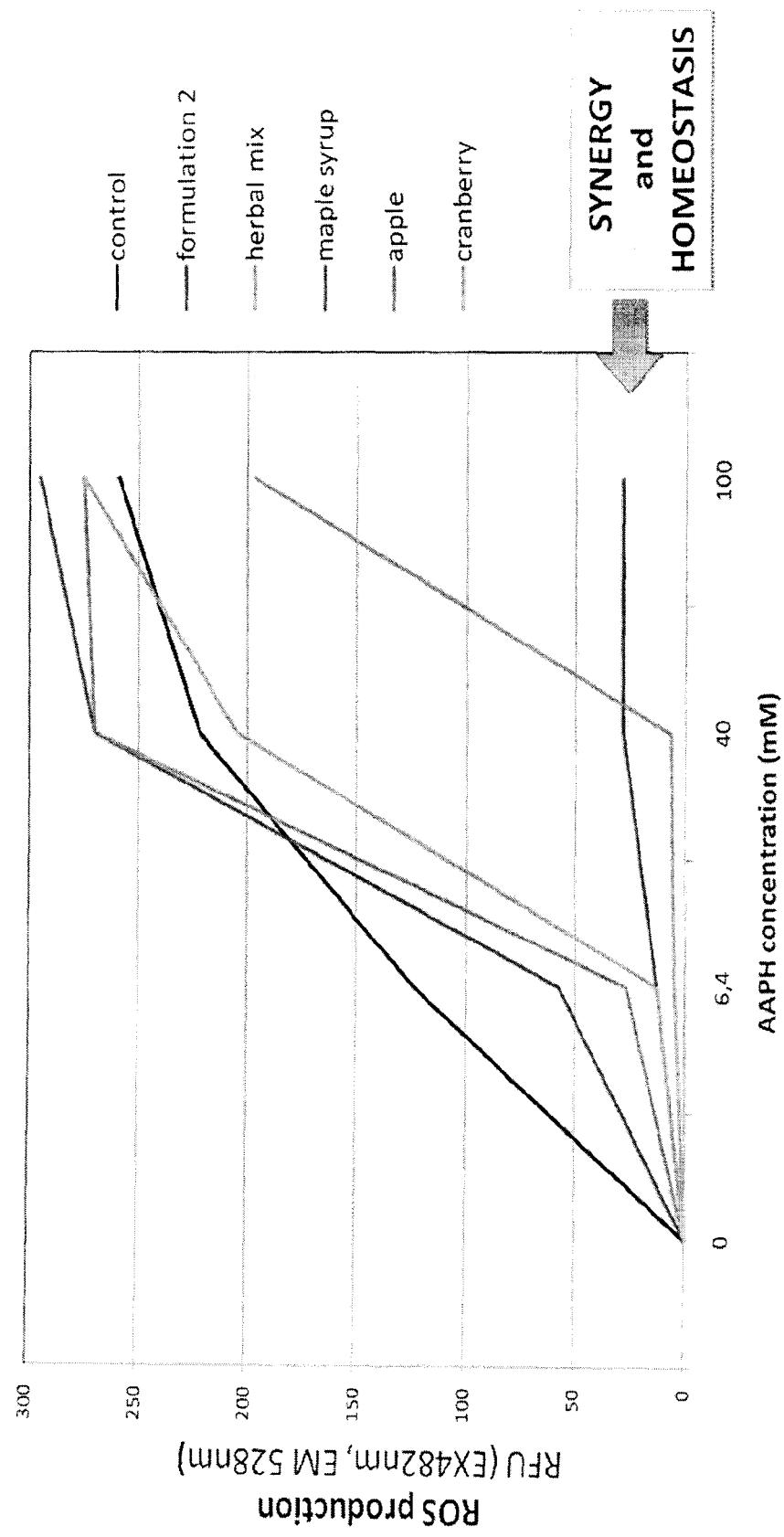
FIG. 22 shows that ingredients of Formulation 2 act in synergy to modulate ROS production artificially induced by AAPH in tongue epithelial CAL27 cells treated for 60 minutes. Values are representative of two separate experiments, and ROS production is expressed as Relative Fluorescence Unit (RFU).

FIG. 22 shows that ingredients of Formulation 2 act in synergy to modulate ROS production artificially induced by AAPH in tongue epithelial CAL27 cells treated for 60 minutes. Ingredients act in synergy to promote homeostasis by maintaining non-damaging levels of ROS.

Figure 23:
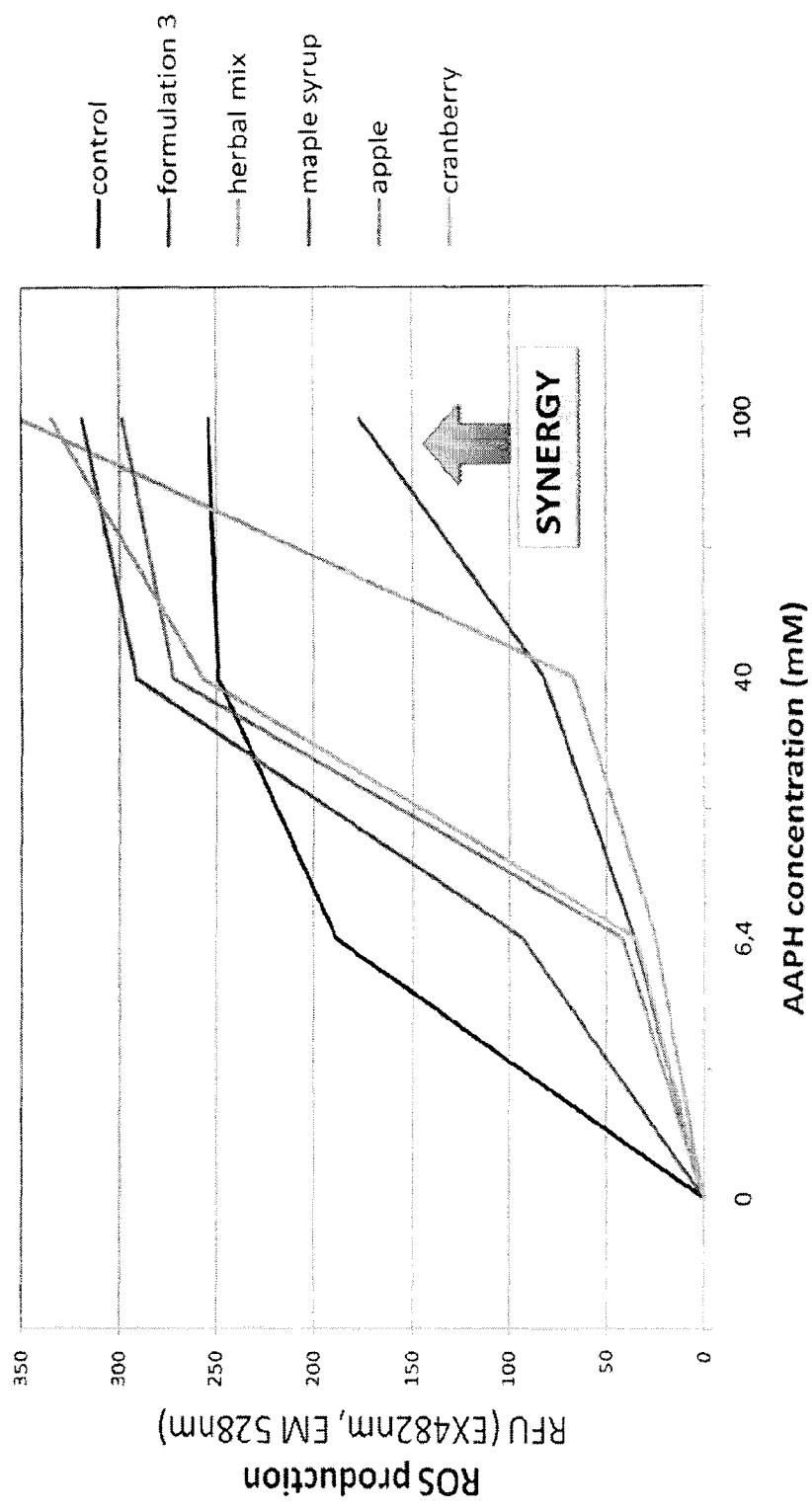
FIG. 23 shows that ingredients of Formulation 3 act in synergy to modulate ROS production artificially induced by AAPH in tongue epithelial CAL27 cells treated for 60 minutes. Values are representative of two separate experiments, and ROS production is expressed as Relative Fluorescence Unit (RFU).

FIG. 23 shows that ingredients of Formulation 3 act in synergy to modulate ROS production artificially induced by AAPH in tongue epithelial CAL27 cells treated for 60 minutes.

Figure 24:
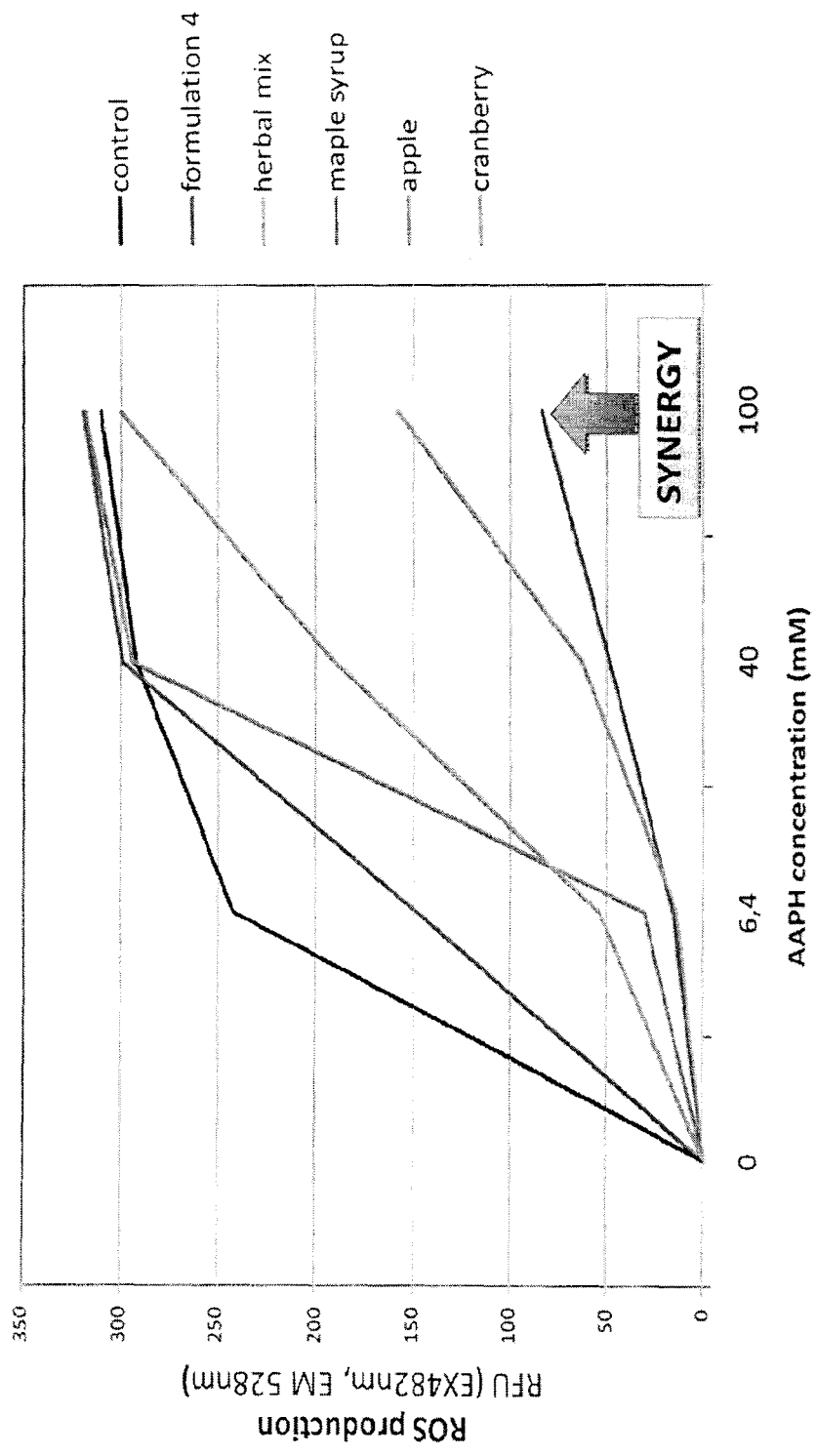
FIG. 24 shows that ingredients of Formulation 4 act in synergy to modulate ROS production artificially induced by AAPH in tongue epithelial CAL27 cells treated for 60 minutes. Values are representative of two separate experiments, and ROS production is expressed as Relative Fluorescence Unit (RFU).

FIG. 24 shows that ingredients of Formulation 4 act in synergy to modulate ROS production artificially induced by AAPH in tongue epithelial CAL27 cells treated for 60 minutes.

Figure 25:
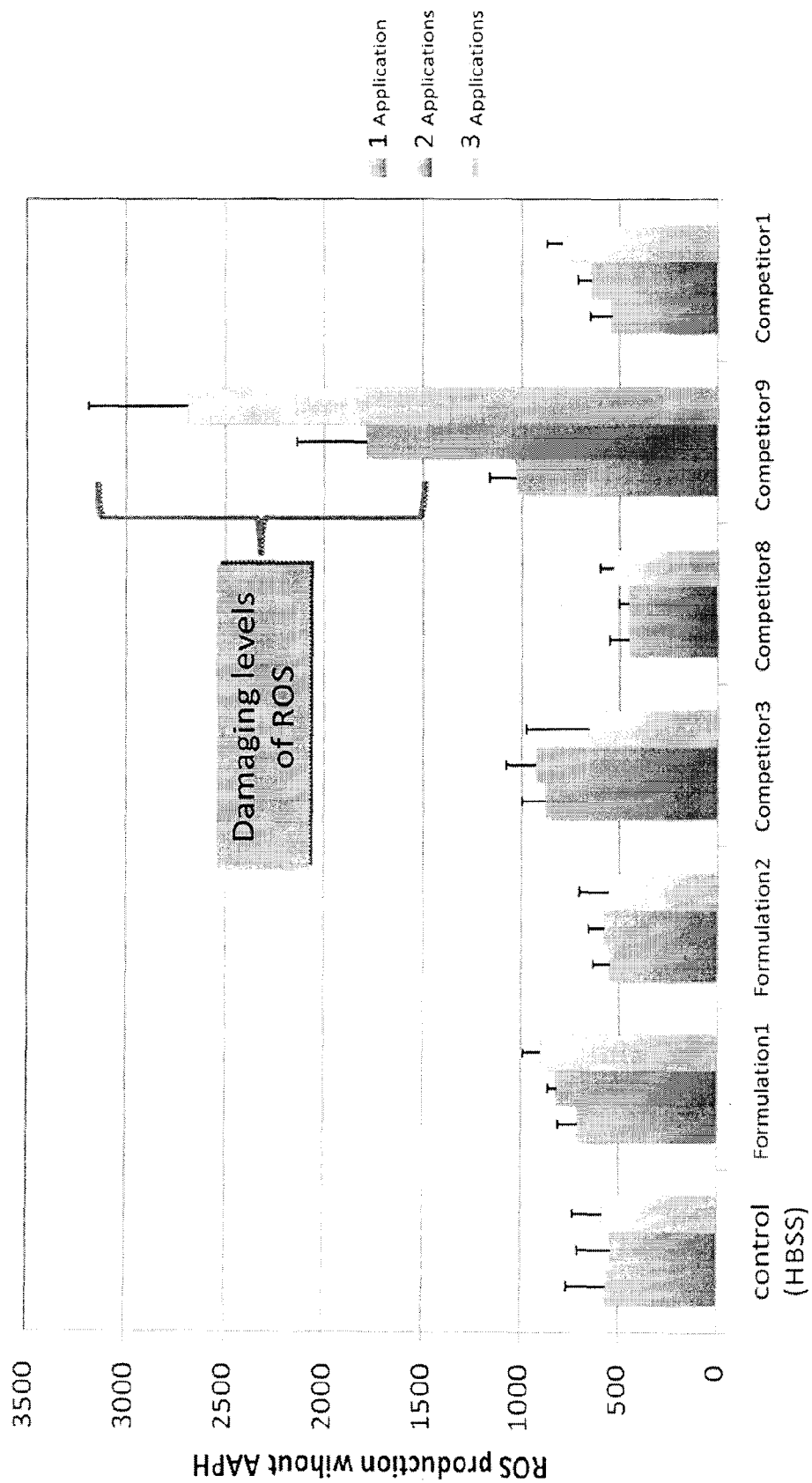
FIG. 25 shows the impact of various formulations on basal ROS production (without the addition of the ROS inducer AAPH) in Cal27 cells. Values of ROS production are expressed as mean+/−SEM of n=3.

Data from FIG. 25 demonstrate that most formulations, except competitor 9, will have little or no impact on basal ROS production, maintaining cells within homeostasis ROS levels. Formulation 1 and 2 did not cause mucosal toxicity by inducing high levels of ROS. High production of ROS by competitor 9 suggests that the formulation is toxic for mucosal cells, and that the formulation can create oxidative stress in a dose-dependent manner by increasing after each application.

Figure 26:
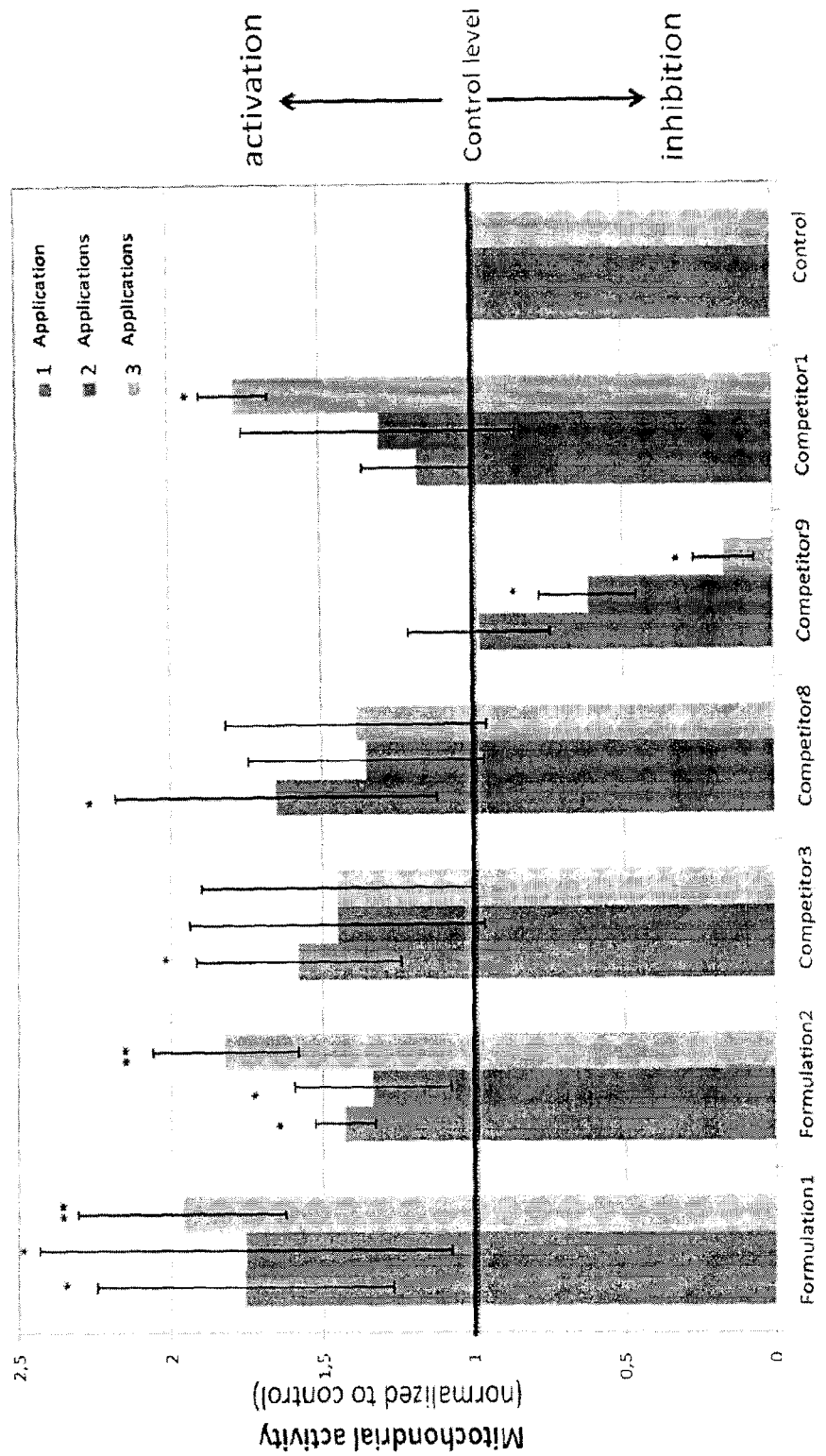
FIG. 26 shows the impact of various formulations on mitochondrial activity of Cal27 cells. MTT results measuring mitochondrial activity were normalized to control levels. Values are expressed as mean+/−SEM of n=3.

Of all products tested, as shown in FIG. 26, formulations developed by Application were best at increasing mitochondria activity in oral epithelium Cal27 cells, and this increase is most pronounced upon a third application of the formulation. Competitor 1 increased mitochondria activity only after the third application of the beverage suggesting this formulation act more slowly than formulations 1 and 2 or that a higher dose of this drink is required to enhance mitochondria activity. Competitor 3 and 8 both increased mitochondria activity of Cal27, but this increase is not maintained after the second and third application. These data suggest that formulations may have a mucosal protective effect by increasing mitochondria activity. Competitor 9 is the only formulation tested that had the opposite effect by inhibiting mitochondria activity in Cal27 cells, suggesting that this formulation causes mucosal toxicity.

Figure 27:
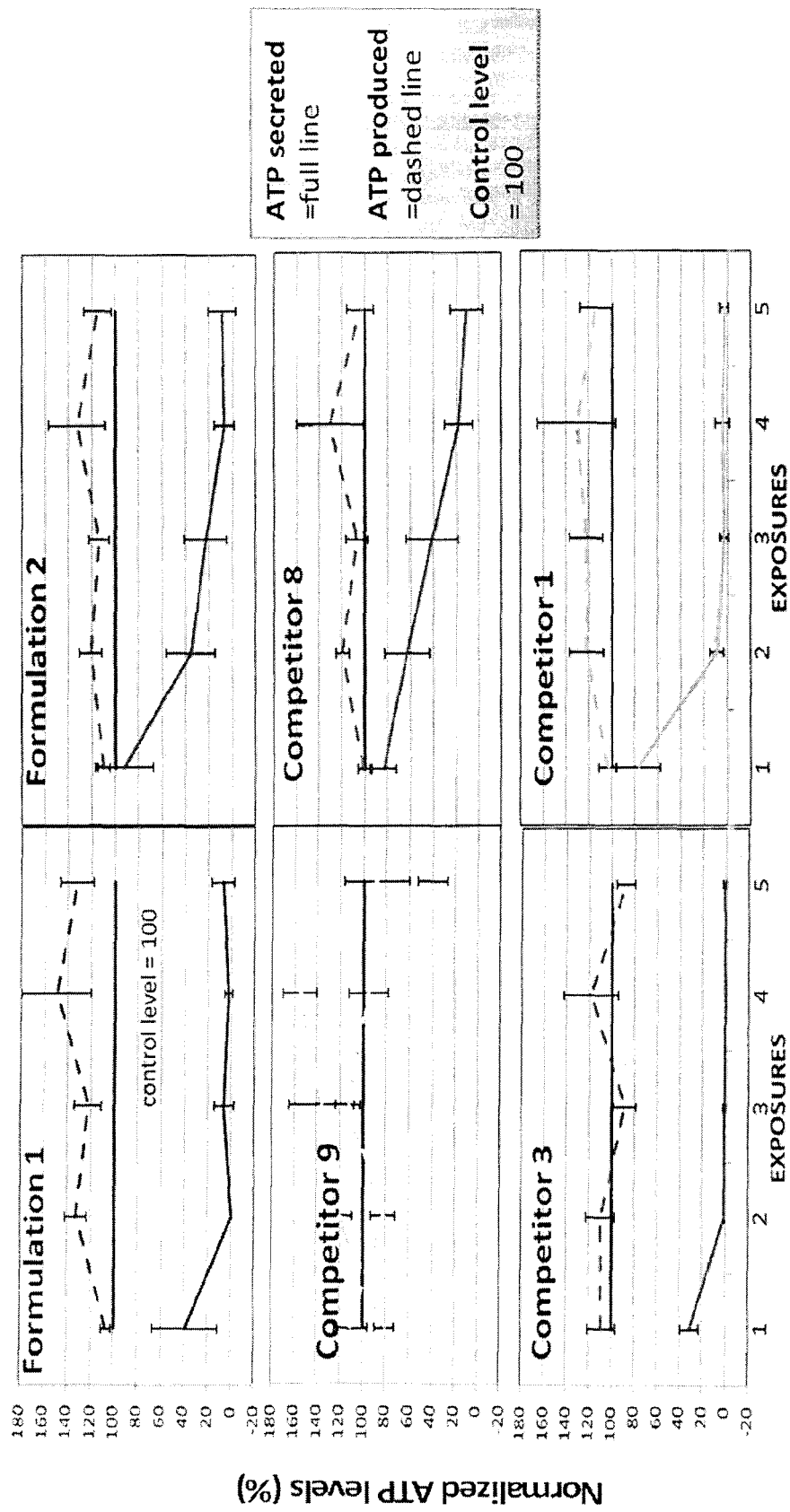
FIG. 27 shows ATP responses of Cal27 cells exposed to various formulations. Extracellular levels of ATP were used as a measure of ATP secretion. Data from 3 separate experiments (n=3) were normalized to control, and values are expressed as mean of normalized ATP levels+/−SEM, where control equals 100%.

For the assay presented in FIG. 27, ATP levels were measured from the conditioned culture media collected following exposure to the different formulations tested. Results show that all formulations, except Competitor 9, inhibit ATP secretion from Cal27 cells in a dose-dependent manner as shown by the inhibition getting stronger upon exposures, suggesting that the retention of ATP is favored for energy conservation purposes. Formulation 1 developed by Applicant was the only formulation tested to block ATP secretion upon the first exposure, suggesting that it is the strongest blocker of ATP secretion. Interestingly, the strong inhibition of ATP secretion by formulation 1 and competitor 3 (the two strongest) correlates with their anthocyanin levels detected in these beverages, suggesting that anthocyanins may be responsible for the energy conservation induced by these formulations. By inducing ATP secretion from Cal27, application of Competitor 9 depletes mucosal cells from their energy fuel that could be required for intracellular reactions. Intracellular levels of ATP from whole cell lysates were used as a measure of ATP synthesis. Again, Formulation 1 was better than other formulation at increasing ATP synthesis of Cal27, while Formulation 2 and Competitor 1 caused a lower increase in ATP synthesis. Competitor 3 and 8 did not cause an energy lift in these cells. Competitor 9 was the only formulation to cause an inhibition of ATP synthesis after the fifth exposure, suggesting that it can act as an energy blocker upon repeated exposures.

Figure 28:
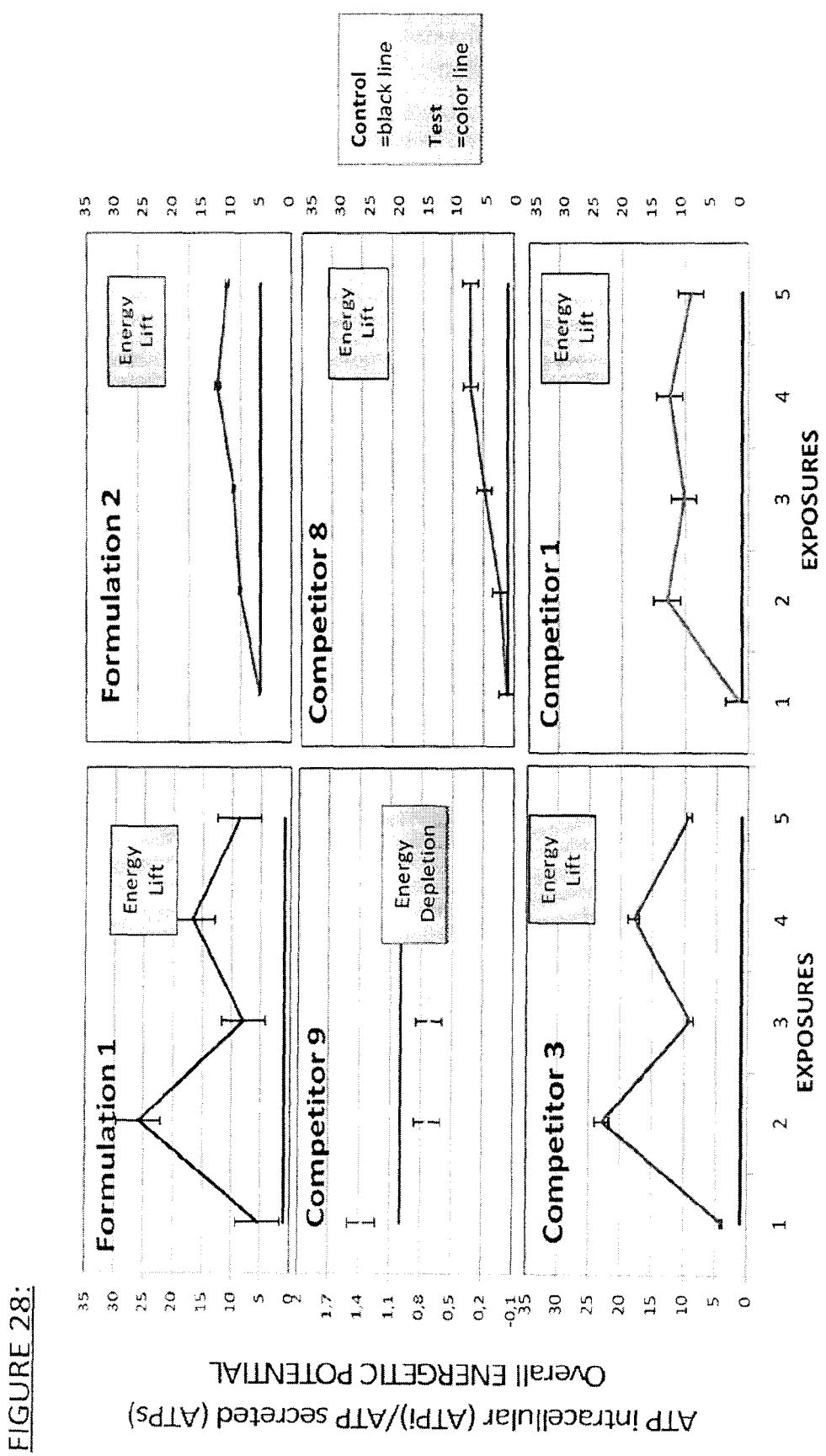
FIG. 28 shows the overall energetic potential of Cal27 cells exposed to various formulations. Data were obtained for 3 separate experiments (n=3). Values are expressed as mean+/−SEM.

By measuring the ratio between intracellular versus extracellular ATP generated upon mucosal exposures to the various formulations, data from FIG. 28 confirm that Formulation 1 developed by Applicant is the best formulation at augmenting the energetic potential of mucosal cells causing an energy lift, while Competitor 9 is the worst of all causing a energy depletion because more ATP is being secreted than produced causing the drainage of cellular fuel. Formulation 2, Competitor 1, 3 and 8 also enhance the energetic potential of mucosal cells. Intracellular ATP levels (ATPi) were divided by extracellular ATP levels (ATPs) to obtain ATPi/ATPs ratio.

Figure 29:
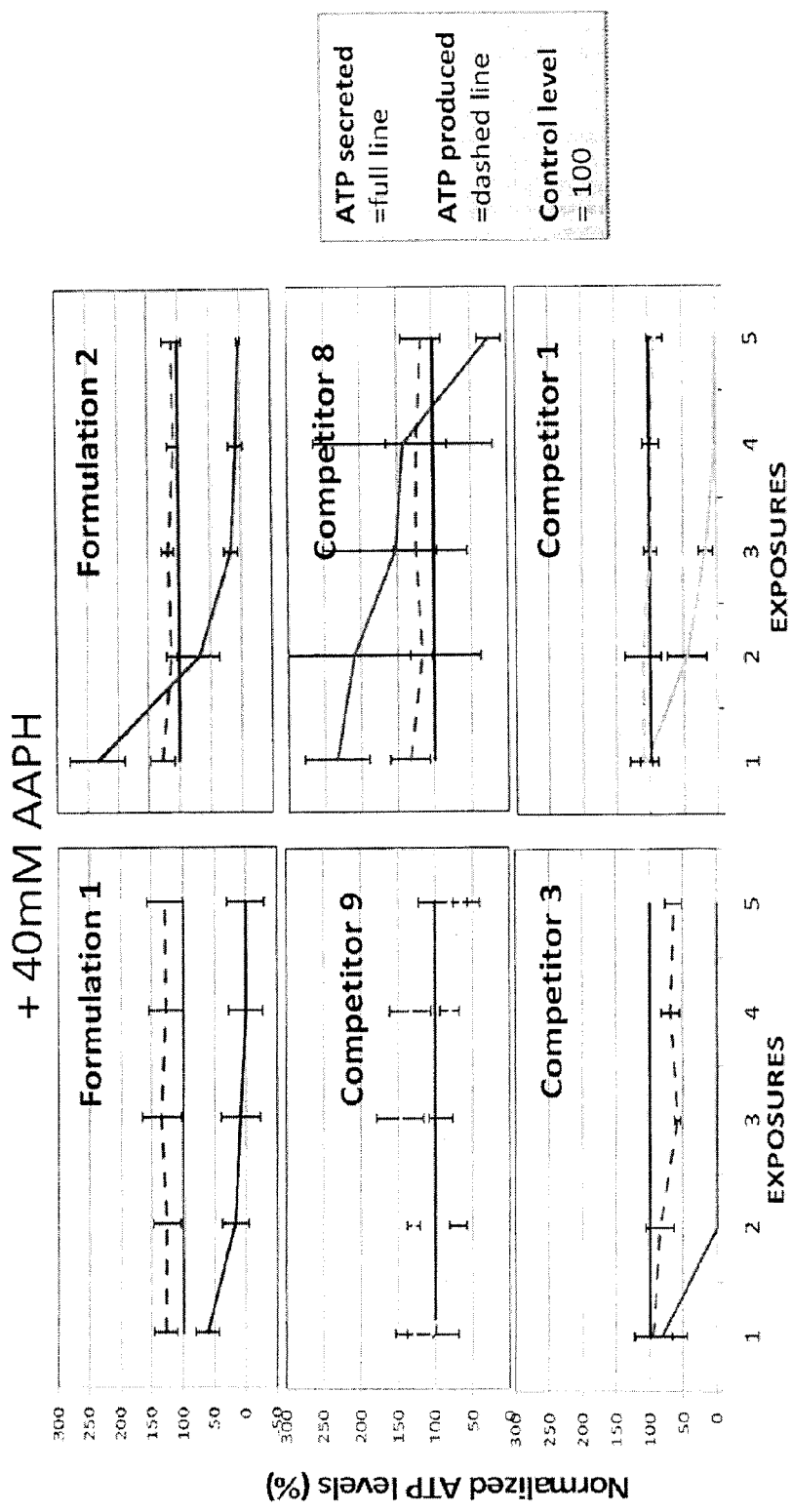
FIG. 29 shows ATP responses in Cal27 cells undergoing oxidative stress (treated with 40 mM AAPH), and exposed to various formulations. Extracellular ATP levels were measured to determine levels of ATP secreted (dashed lines). Values were normalized to control levels, and are expressed as mean+/−SEM of normalized ATP levels of three separate experiments (n=3).

Like in normal Cal27 cells (see FIG. 21), FIG. 29 shows data indicating that formulation 1 as well as competitors 1 and 3 inhibit ATP secretion in stressed Cal27. However, in contrast to what was observed in normal cells (FIG. 21), ATP secretion was induced upon the first application of competitor 8 and formulation 2 developed by Applicant, suggesting they can provide a rapid energy boost in stressed conditions. Like in normal cells (FIG. 21), competitor 9 induced ATP secretion from Cal27 cells. Intracellular ATP produced (full lines) upon exposure to various formulations were measured from whole cell lysates. Formulation 1 and 2 slightly, but significantly, induced ATP production in stressed Cal27 cells. Others formulations did not, and competitor 3 even caused its inhibition after 3 exposures.

Figure 30:
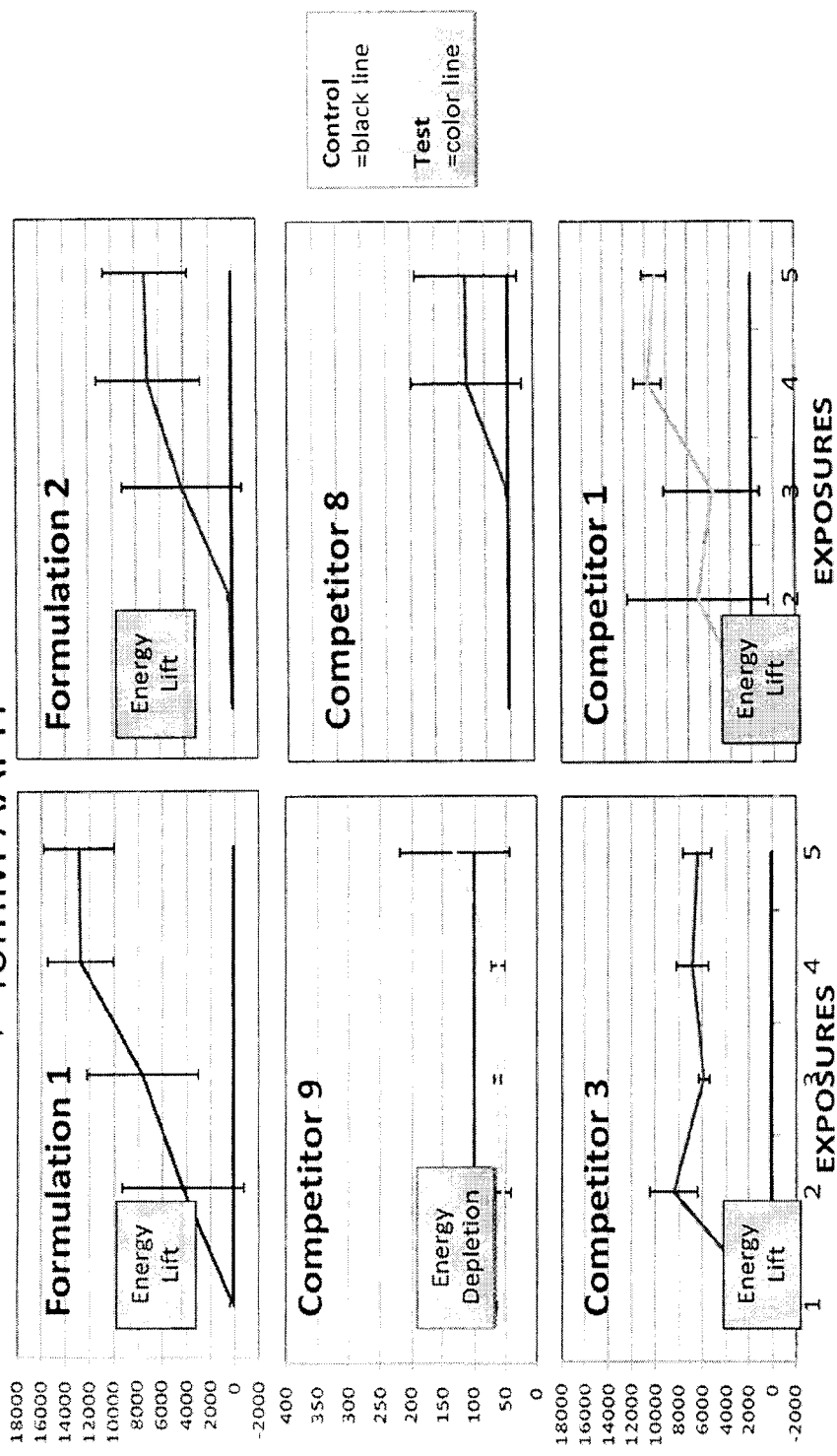
FIG. 30 shows the overall energetic potential of Cal27 cells exposed to various formulations. Values of three separate experiments (n=3) were normalized to control levels, and are expressed as mean+/−SEM of normalized ATP levels produced.

By measuring the ratio between intracellular versus extracellular ATP generated upon mucosal exposures to the various formulations, FIG. 30 shows data confirming that formulation 1 developed by Applicant was best at inducing a strong energy lift in stressed Cal27 cells, and ATPi/ATPs ratio were much higher (100× more) than those observed in normal cells (FIG. 22) indicating that formulation is better at inducing an energy lift in stressed cells than normal cells. Formulation 2, competitor 1 and competitor 8 also induced ATP production in stressed Cal27 cells causing a significant energy lift, but in contrast to what was observed in normal cells (FIG. 22), competitor 3 did not induce a significant energy lift. Like in normal cells, competitor 9 inhibited the production of ATP causing an energy depleted state.

Figure 31:
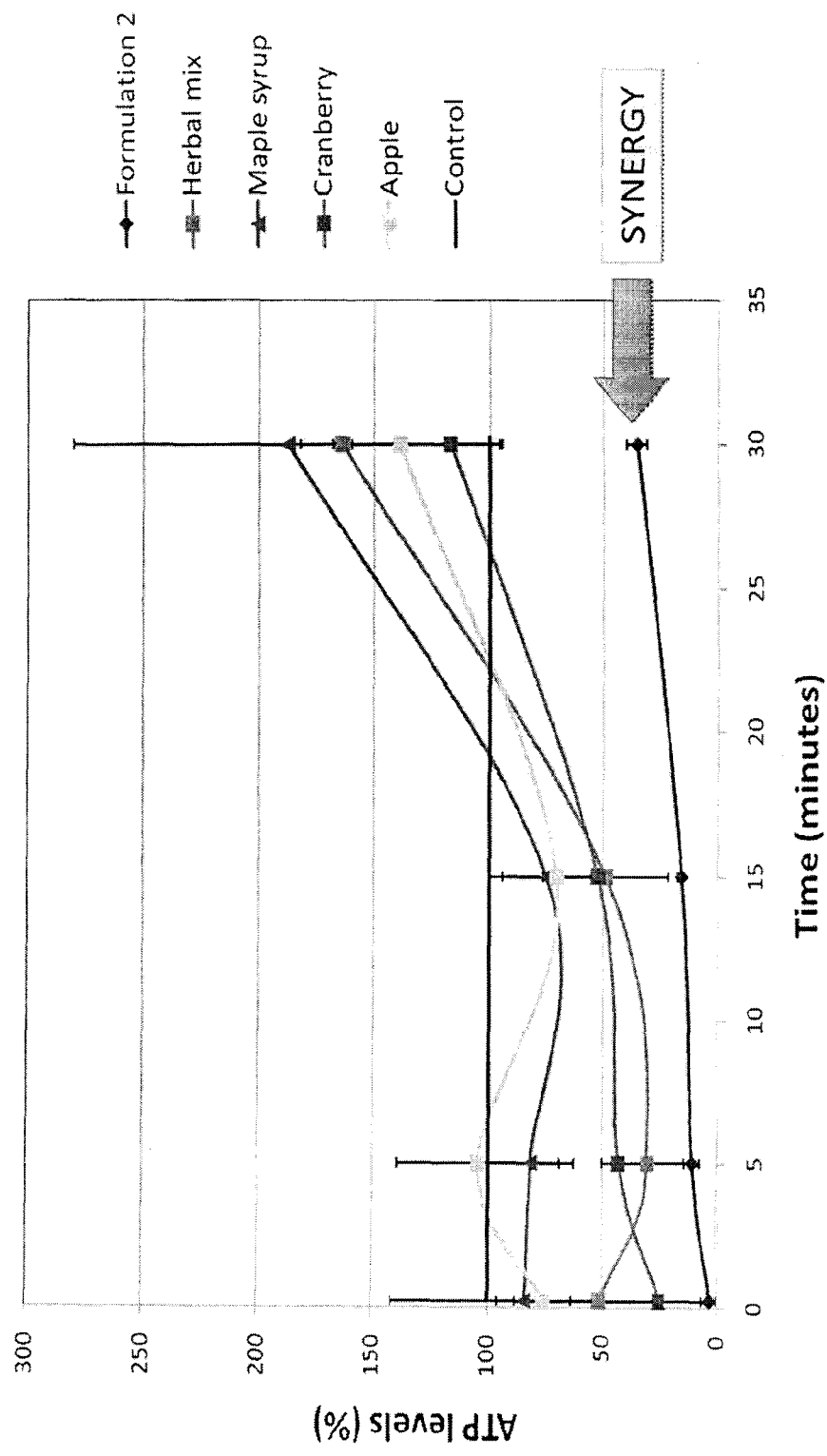
FIG. 31 shows that ingredients of formulation 2 act in synergy to block ATP secretion in Cal27 to cause a maintained state of energy conservation. Extracellular ATP levels were normalized to untreated control (100%). Values are mean+/−SEM of n=2.

FIG. 31 shows that ingredients of formulation 2 act in synergy to block ATP secretion in Cal27 to cause a maintained state of energy conservation. The synergy can be observed 30 minutes after exposure with whole formulations, when compared to individual ingredients.

Figure 32:
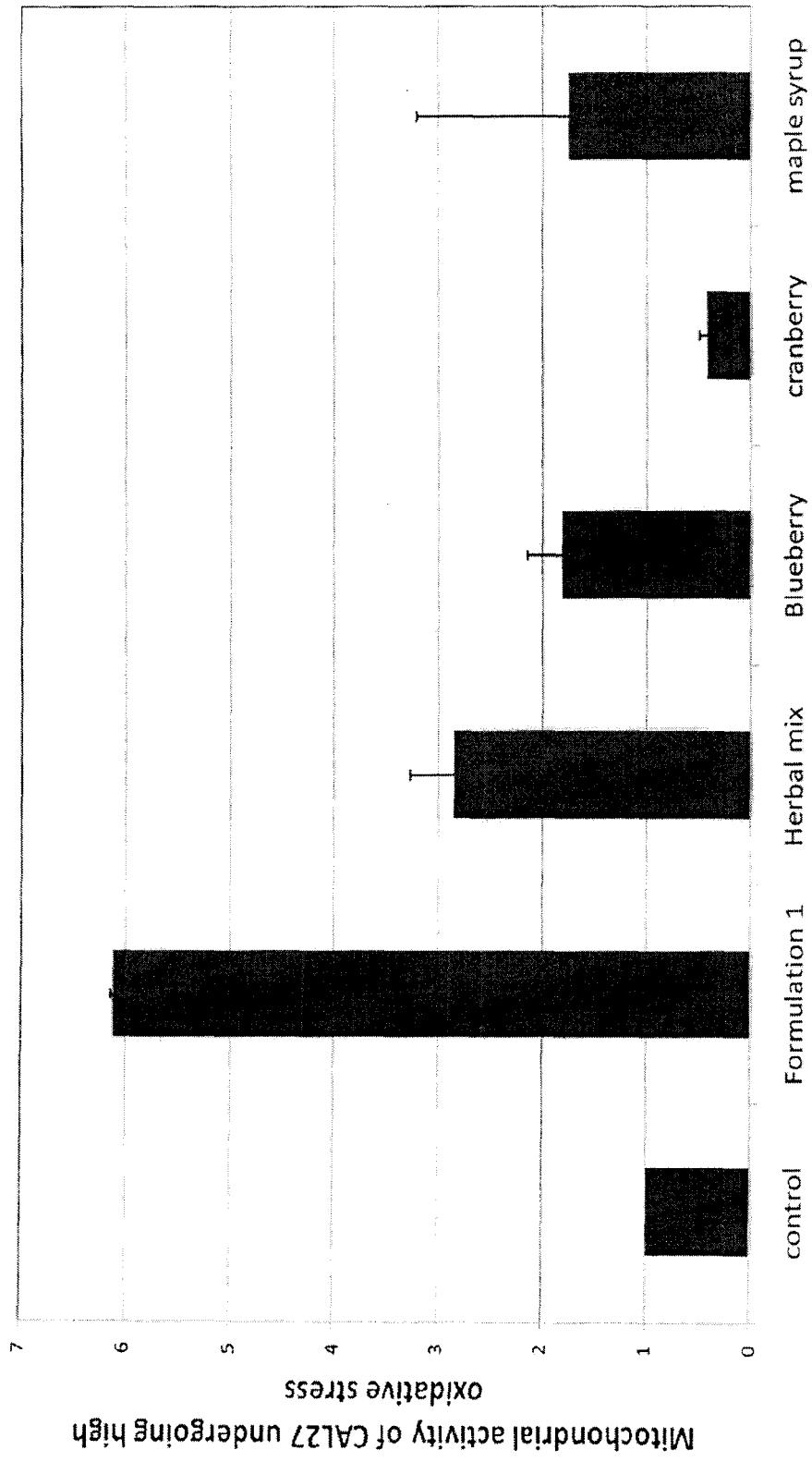
FIG. 32 demonstrates that ingredients of formulation 1 act in synergy to enhance mitochondrial activity of CAL27 cells undergoing high oxidative stress. Values are expressed as mean+/−SEM of n=3.

FIG. 32 demonstrates that ingredients of formulation 1 act in synergy to enhance mitochondrial activity of CAL27 cells undergoing high oxidative stress. Cal27 were treated with 100 mM AAPH for 120 minutes.

Figure 33:
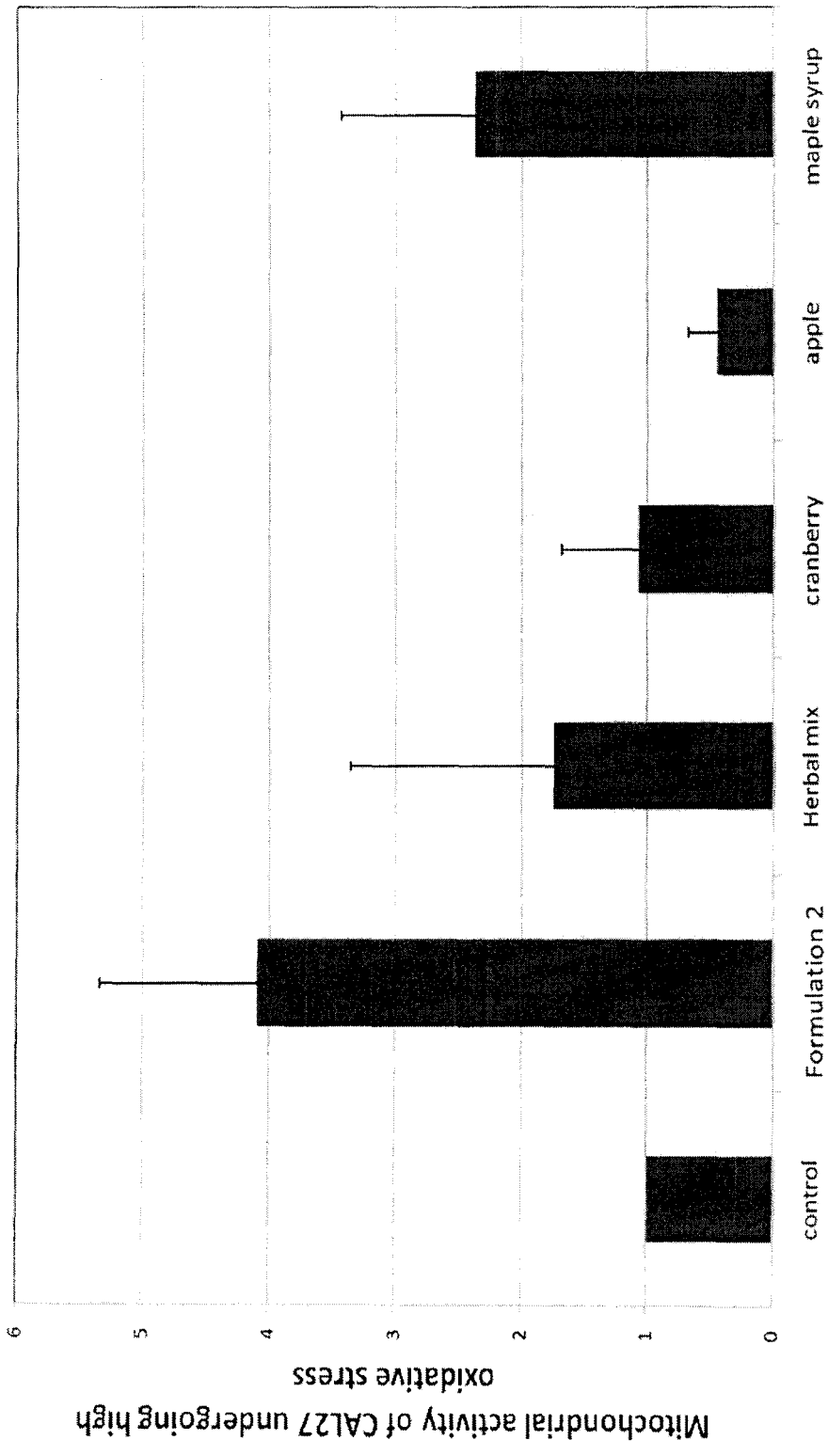
FIG. 33 demonstrates that ingredients of formulation 2 act in synergy to enhance mitochondrial activity of CAL27 cells undergoing high oxidative stress. Values are expressed as mean+/−SEM of n=3.

FIG. 33 demonstrates that ingredients of formulation 2 act in synergy to enhance mitochondrial activity of CAL27 cells undergoing high oxidative stress. Cal27 were treated with 100 mM AAPH for 120 minutes.

Figure 34:
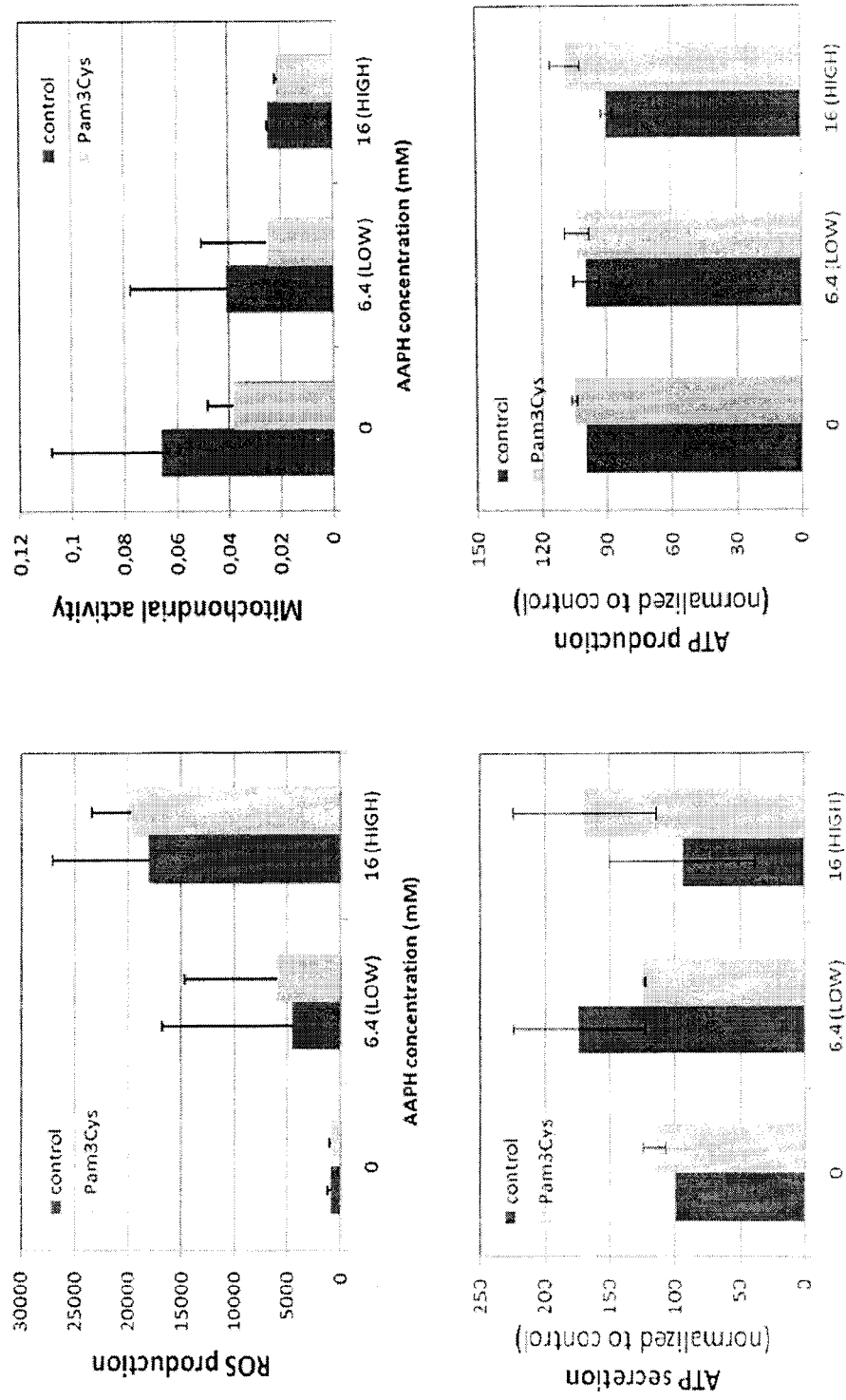
FIG. 34 shows the impact of TLR2 activation with TLR2 agonist Pam3Cys (500 ng/ml) on ROS production, mitochondrial activity and ATP responses in Cal27 cells undergoing low or high oxidative stress upon treatment with 6.4 mM and 16 mM AAPH respectively. Values are expressed as mean+/−SEM of n=3.

FIG. 34 shows the impact of TLR2 activation with TLR2 agonist Pam3Cys (500 ng/ml) on ROS production, mitochondrial activity and ATP responses in Cal27 cells undergoing low or high oxidative stress upon treatment with 6.4 mM and 16 mM AAPH respectively. ROS production increases upon AAPH treatment while mitochondrial activity decreases, and TLR2 agonist had no significant impact on these responses. ATP secretion and ATP production were not affected by low or high MPH treatment, TLR2 agonist slightly increased ATP secretion in cells without AAPH, while it increases ATP production in cell undergoing high oxidative stress.

Figure 35:
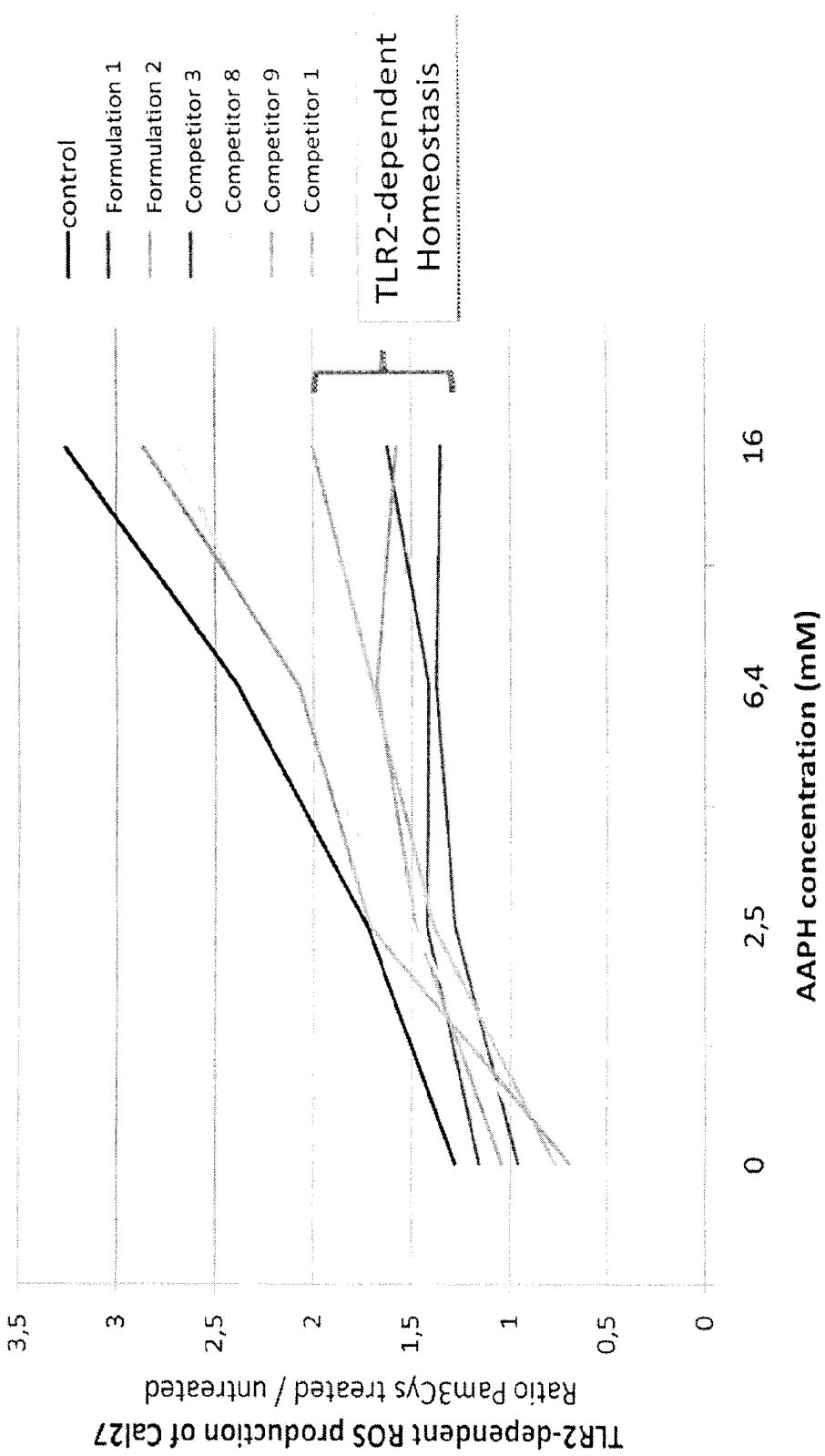
FIG. 35 demonstrates the impact of various formulations on TLR2-dependent ROS production in Cal27 exposed for 30 minutes to various concentrations of AAPH. Data is representative of two separate experiments.

FIG. 35 demonstrates the impact of various formulations on TLR2-dependent ROS production in Cal27 exposed for 30 minutes to various concentrations of AAPH. TO obtain TLR2-specific ROS production, ROS values of Pam3Cys treated cells were divided by that of untreated cells to obtain the ratio shown in the graph. As expected, in control cells, TLR2-dependent ROS production increased in a dose-dependent manner. However, when cells were exposed to formulation 1, formulation 2, competitor 3, and to a lesser extent competitor 1, TLR2-dependent ROS production was significantly reduced to maintain homeostasis levels of ROS. Competitor 8 and 9 did not significantly affect TLR2-dependent ROS production.

Figure 36:
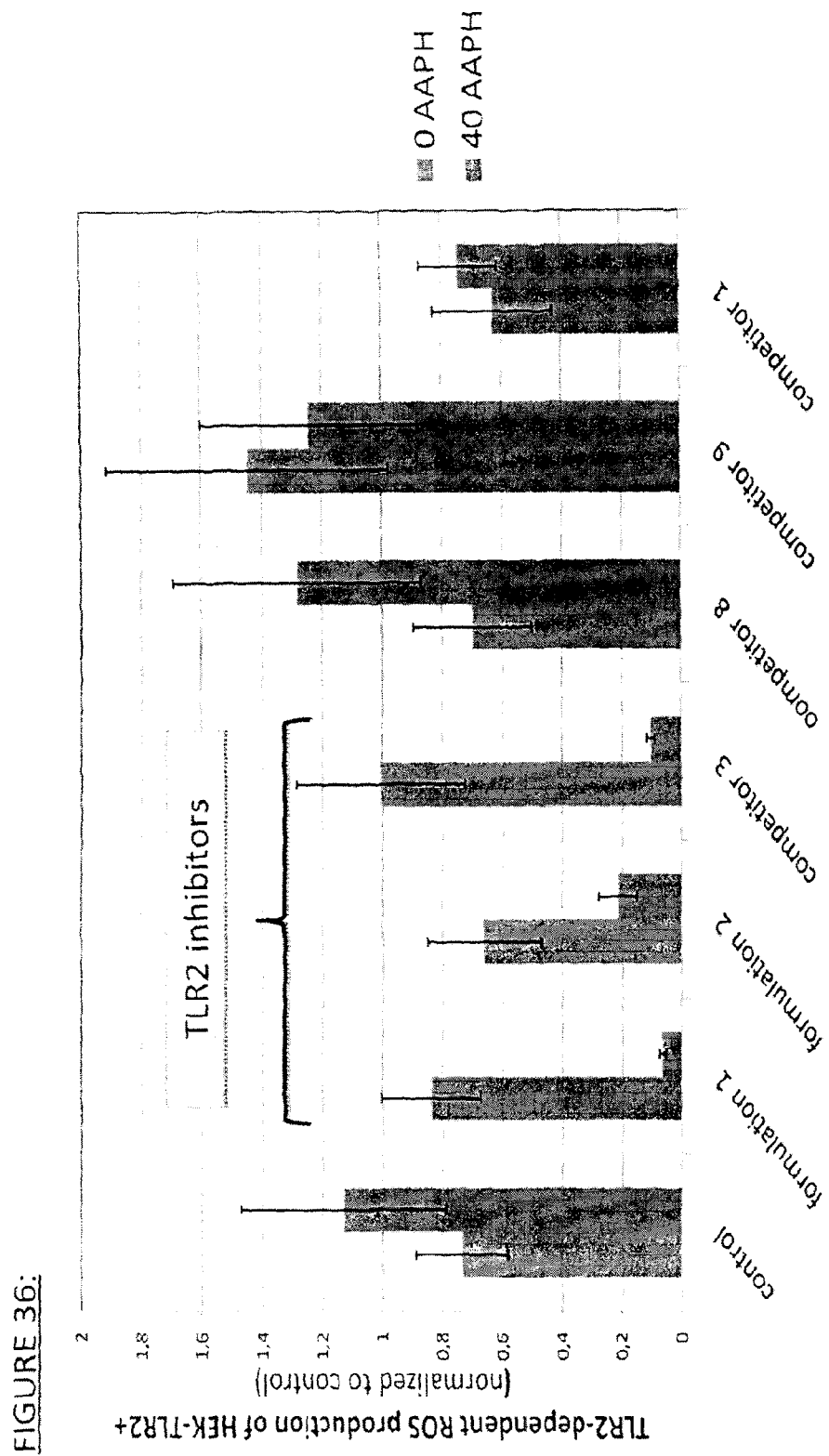
FIG. 36 shows TLR2-specific ROS production in HEK-TLR2+ cells treated for 3 hours with Pam3Cys (500 ng/ml). Values are expressed as mean+/−SEM of n=4.

FIG. 36 shows TLR2-specific ROS production in HEK-TLR2+ cells treated for 3 hours with Pam3Cys (500 ng/ml). Cells were then exposed to various formulations with or without ROS inducer (40 mM AAPH) for 30 minutes. TLR2-specific ROS production was inhibited in MPH-treated Cal27 by formulation 1, formulation 2, and competitor 3 providing evidence that they can act as TLR2 inhibitors when cells are undergoing high oxidative stress. This TLR2 inhibition was not observed in normal cells. Other formulations tested had no impact on TLR2-specific ROS production in cells undergoing oxidative stress. One should note that formulation 2 had no longer TLR2-inhibitory effect after 60 minutes, while formulation 1 and competitor 3 conserved its TLR2-inhibitory potential as long as 120 minutes (data not shown).

Figure 37:
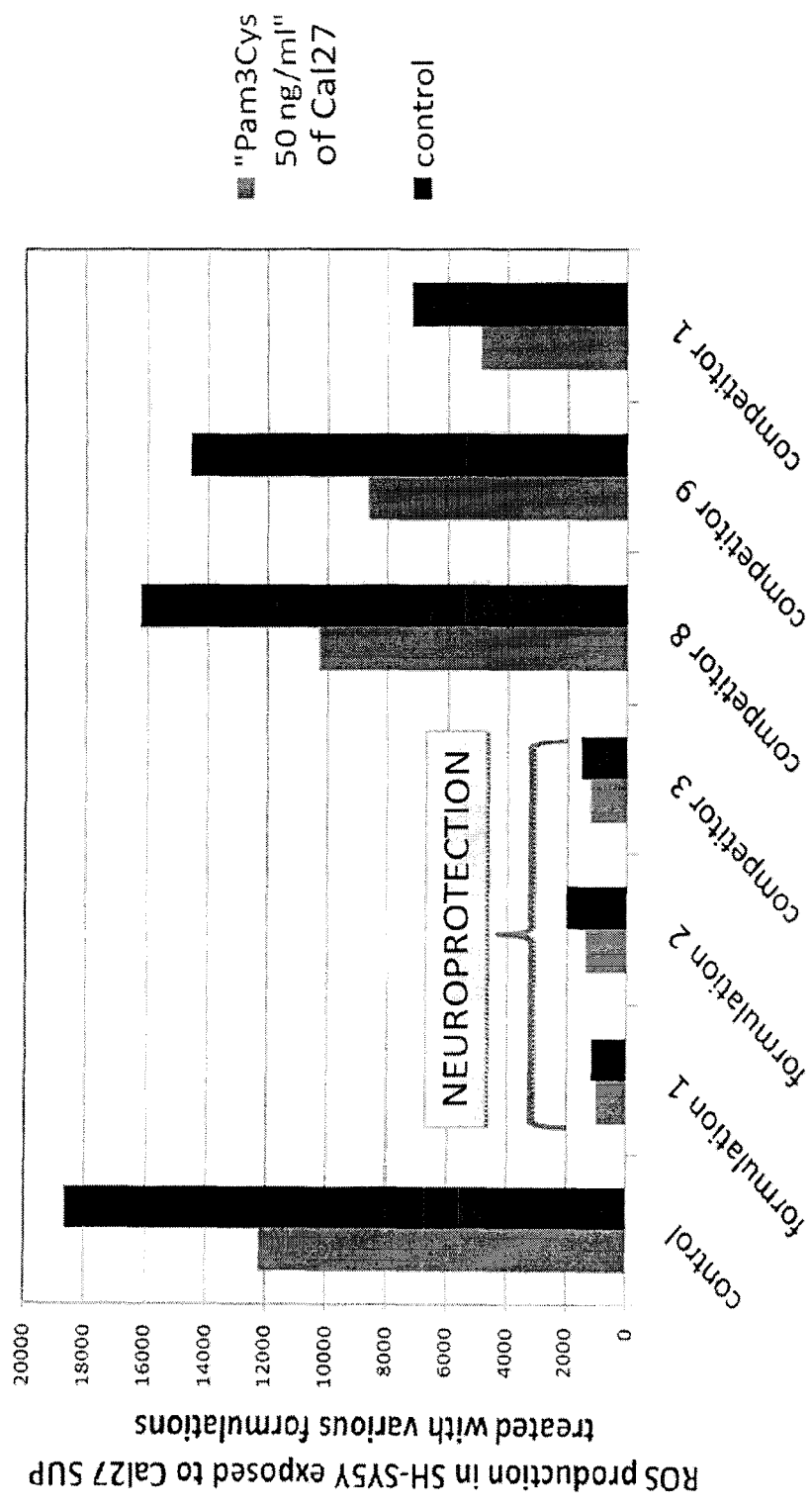
FIG. 37 shows ROS production by dopaminergic SH-SY5Y neurons exposed to supernatant of Cal27 cells exposed to various formulations and the impact of low TLR2 activation induced with 50 ng/ml of Pam3Cys. Data are representative of 2 separate experiments.

FIG. 37 shows ROS production by dopaminergic SH-SY5Y neurons exposed to supernatant of Cal27 cells exposed to various formulations and the impact of low TLR2 activation induced with 50 ng/ml of Pam3Cys. This assay mimics the impact of mucosal cells on subepithelial neuronal cells. Results demonstrate that TLR2 activation of Cal27 cells can reduce ROS production by dopaminergic neurons, suggesting a neuroprotective role for mucosal TLR2. One should note that higher dose of Pam3Cys (250 or 500 ng/ml) did not have this neuroprotective role, suggesting that mucosal TLR2 can only be neuroprotective under low activity. Exposure to formulation 1, formulation 2, and competitor 3 had a neuroprotective effect, inhibiting ROS production in dopaminergic cells, while competitor 8 and competitor 9 did not. Competitor 1 had a low neuroprotective potential compared to formulation 1.

Figure 38:
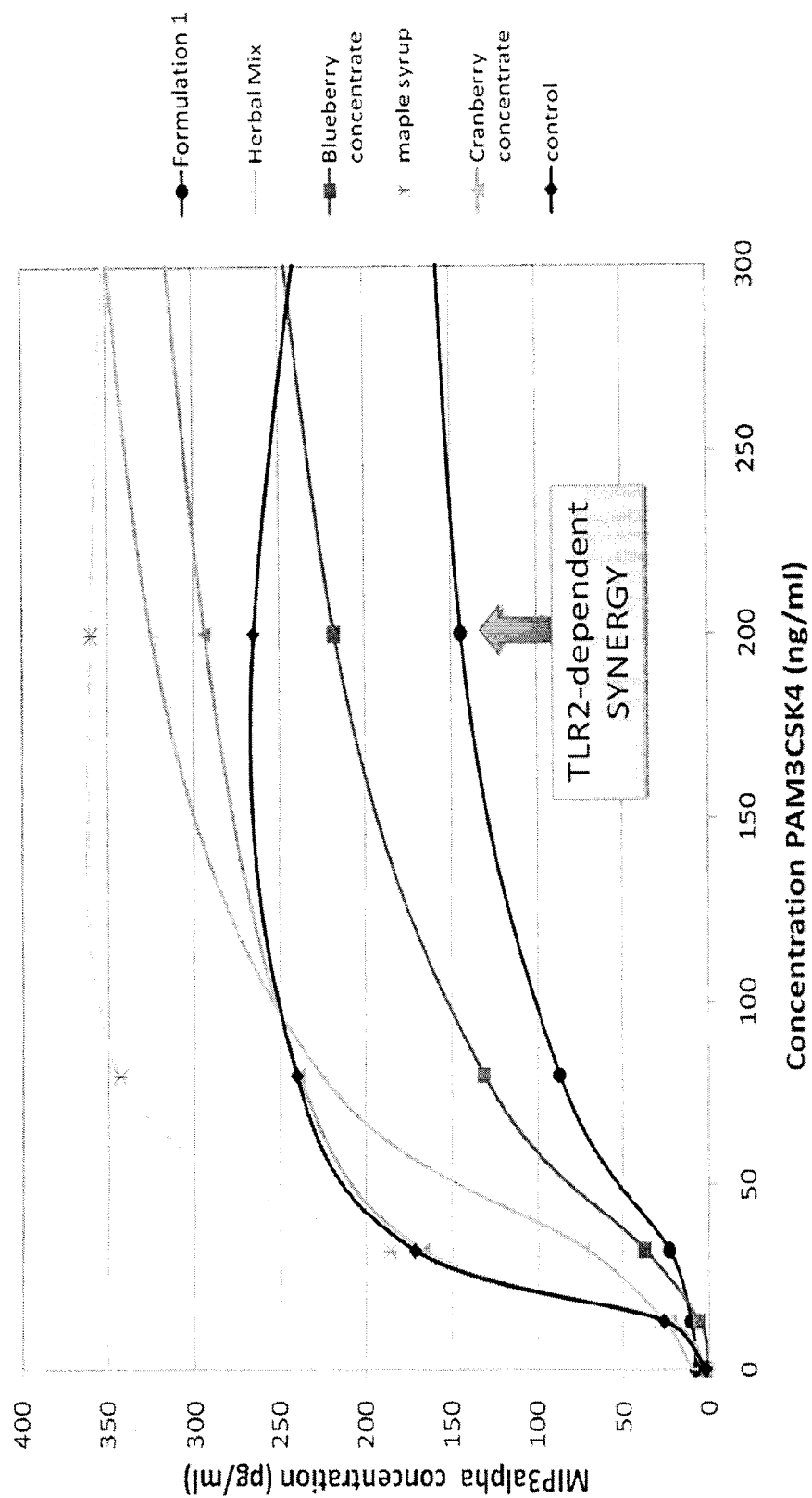
FIG. 38 shows that Ingredients of functional beverage developed by Applicant (Formulation 1) act in synergy to modulate the TLR2-dependent release of DC-attracting chemokine MIP3α from HEK-TLR2+ cells (16 hours incubation). This data is representative of two separate experiments.

FIG. 38 shows that Ingredients of functional beverage developed by Applicant (Formulation 1) act in synergy to modulate the TLR2-dependent release of DC-attracting chemokine MIP3α from HEK-TLR2+ cells (16 hours incubation), suggesting that formulation 1 can cause the recruitment of DCs via TLR2 modulation to promote the activation of innate immune responses.

Figure 39:
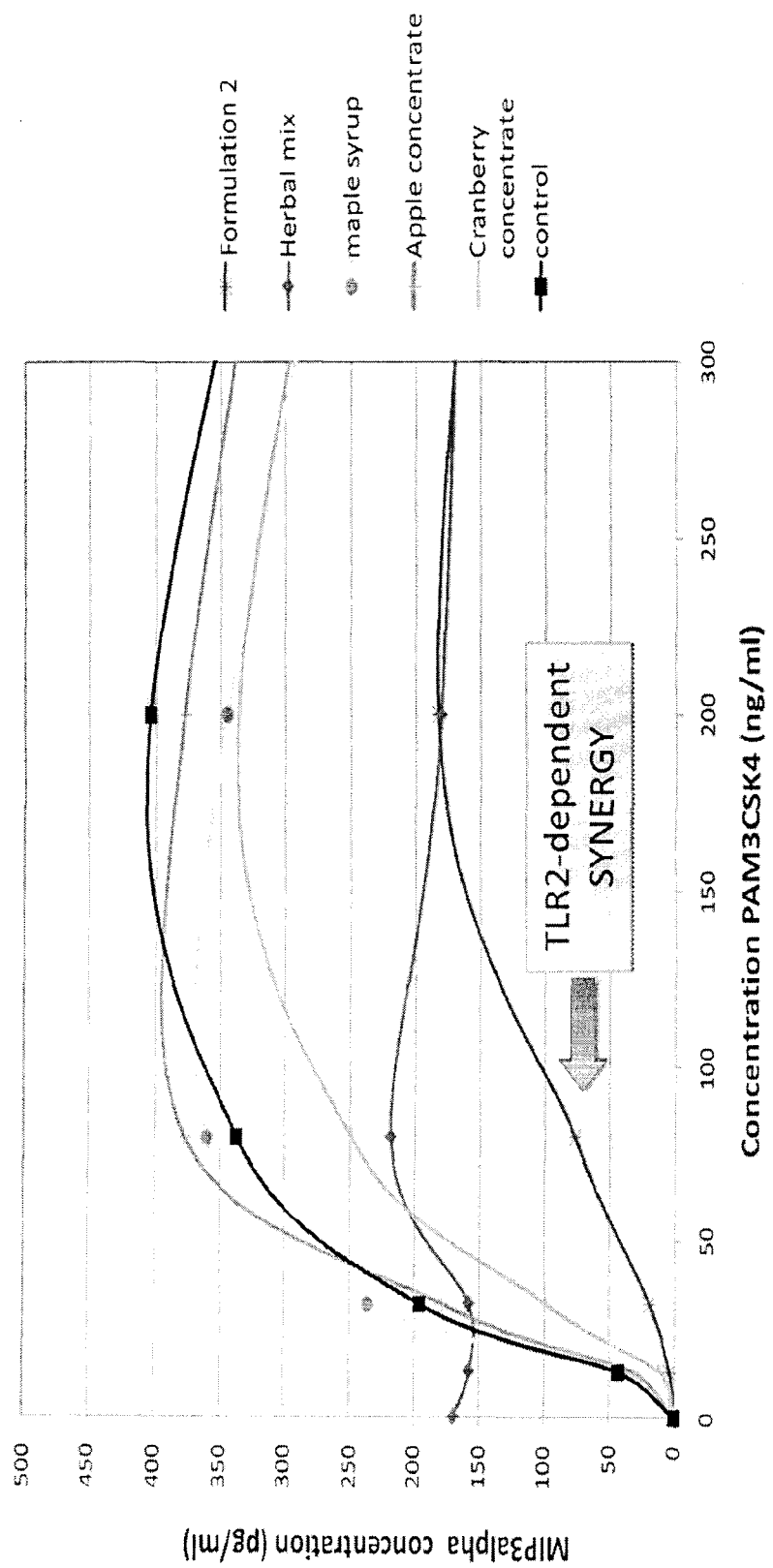
FIG. 39 Ingredients of functional beverage developed by Applicant (Formulation 2) act in synergy to modulate the TLR2-dependent release of DC-attracting chemokine MIP3α from HEK-TLR2+ cells (16 hours incubation). This data is representative of two separate experiments.

FIG. 39 Ingredients of functional beverage developed by Applicant (Formulation 2) act in synergy to modulate the TLR2-dependent release of DC-attracting chemokine MIP3α from HEK-TLR2+ cells (16 hours incubation), suggesting that formulation 2 can cause the recruitment of DCs via TLR2 modulation to modulate innate immune responses.

Figure 40:
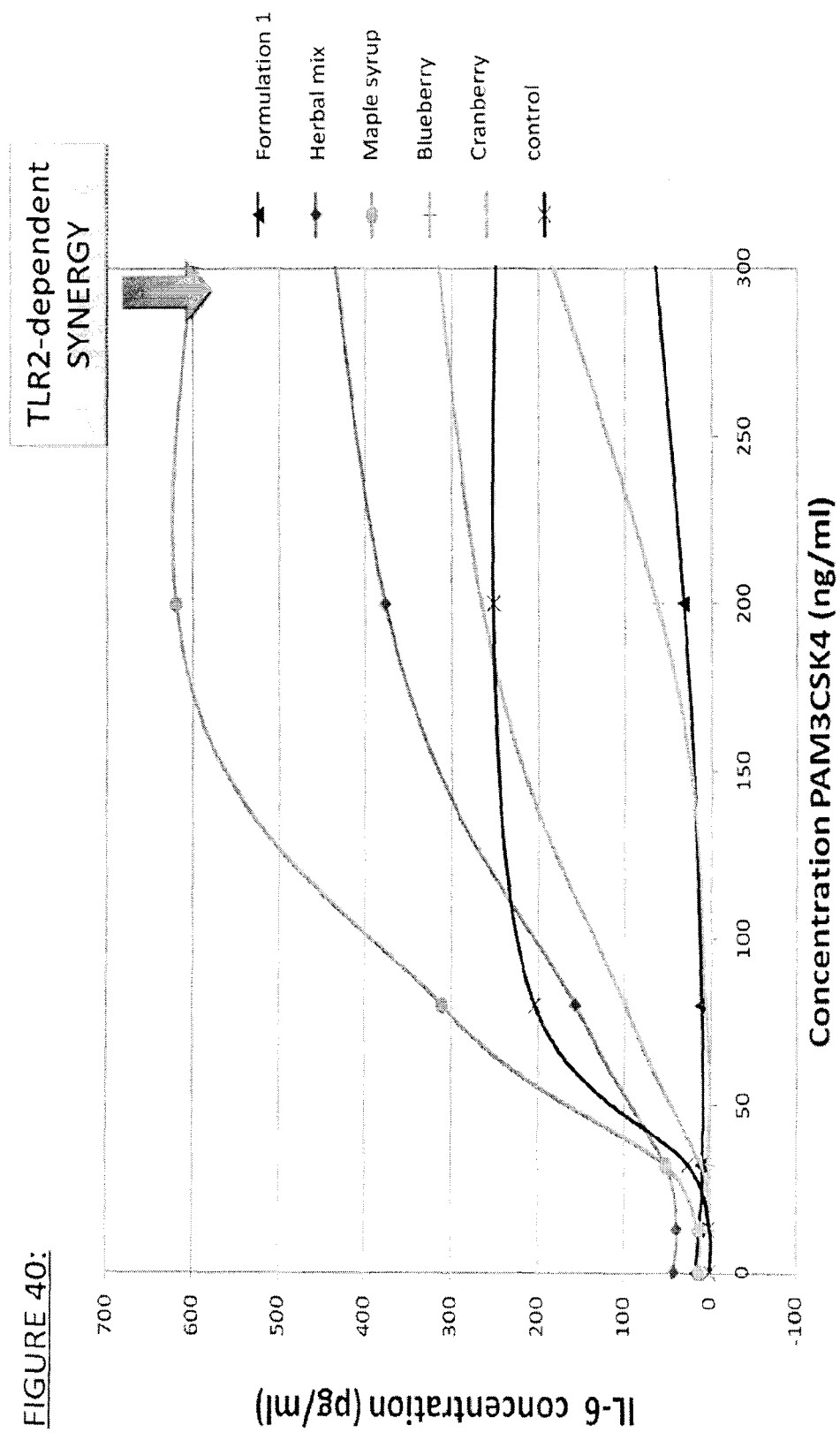
FIG. 40 shows that ingredients of Formulation 1 (SN) act in synergy to inhibit release of pro-inflammatory cytokine IL-6 in THP1-PMA cells treated with PAM3CSK4 for 22 hours. This data is representative of two separate experiments.

FIG. 40 shows that ingredients of Formulation 1 (SN) act in synergy to inhibit release of pro-inflammatory cytokine IL-6 in THP1-PMA cells treated with PAM3CSK4 for 22 hours, suggesting that formulation 1 can have an impact on pain regulation via an impact on IL-6 release.

Figure 41:
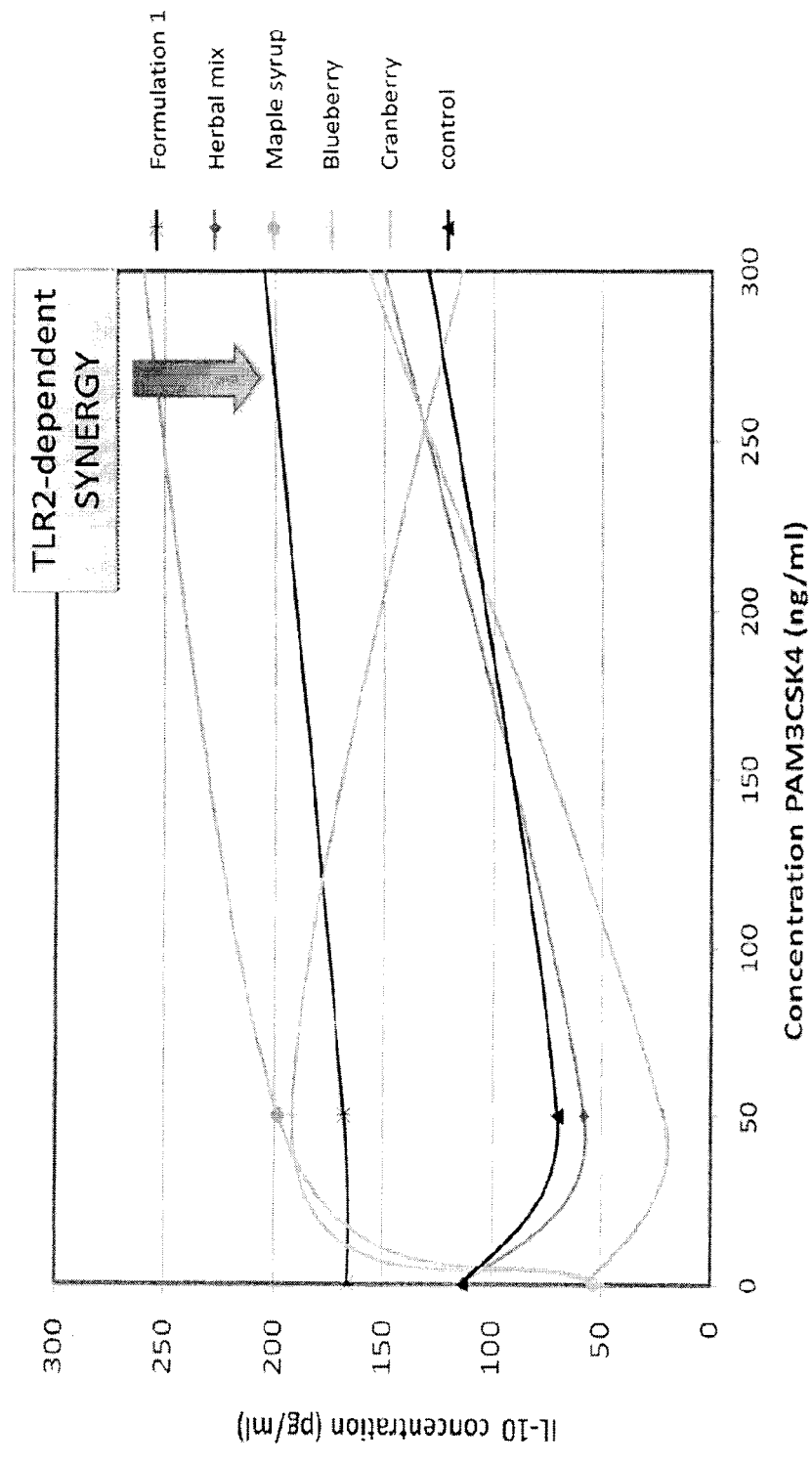
FIG. 41 shows that ingredients of Formulation 1 act in synergy to enhance release of anti-inflammatory cytokine IL-10 in THP1-PMA cells at basal condition. Values are expressed as pg/ml of human IL10.

FIG. 41 shows that ingredients of Formulation 1 act in synergy to enhance release of anti-inflammatory cytokine IL-10 in THP1-PMA cells at basal condition, suggesting that formulation 1 can promote a tolerant response in normal condition and via TLR2 modulation.

Figure 42:
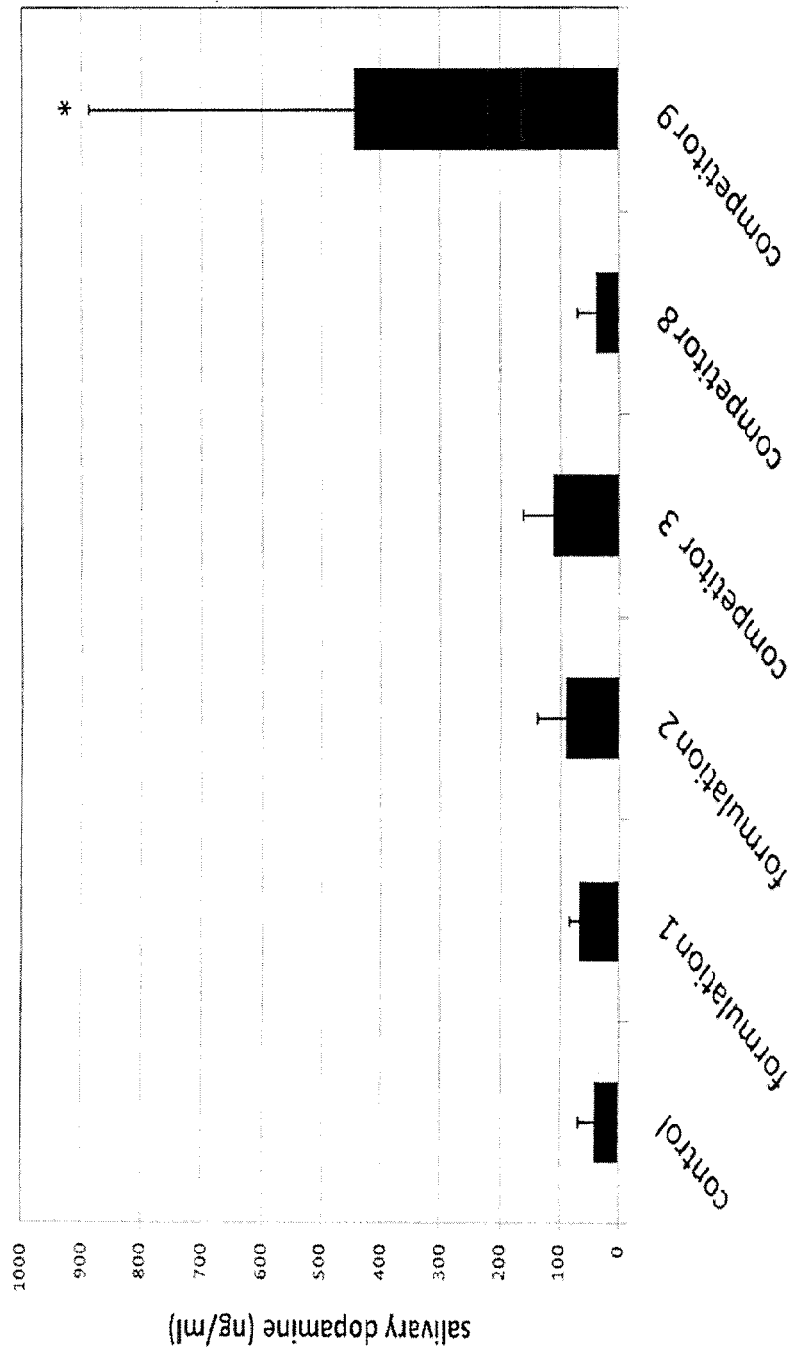
FIG. 42 shows the levels of salivary dopamine detected 5 minutes after drinking 20 ml of various beverages in healthy human individuals. Values are expressed as Mean+/−SEM of salivary dopamine ng/ml of at least n=6.

FIG. 42 shows the levels of salivary dopamine detected 5 minutes after drinking 20 ml of various beverages in healthy human individuals. Competitor 9 significantly enhanced levels of salivary dopamine compared to control (water), whereas all other formulations tested did not. This data suggests that, in contrast to competitor 9, formulations developed by Applicant do not induce an addictive response.

Figure 43:
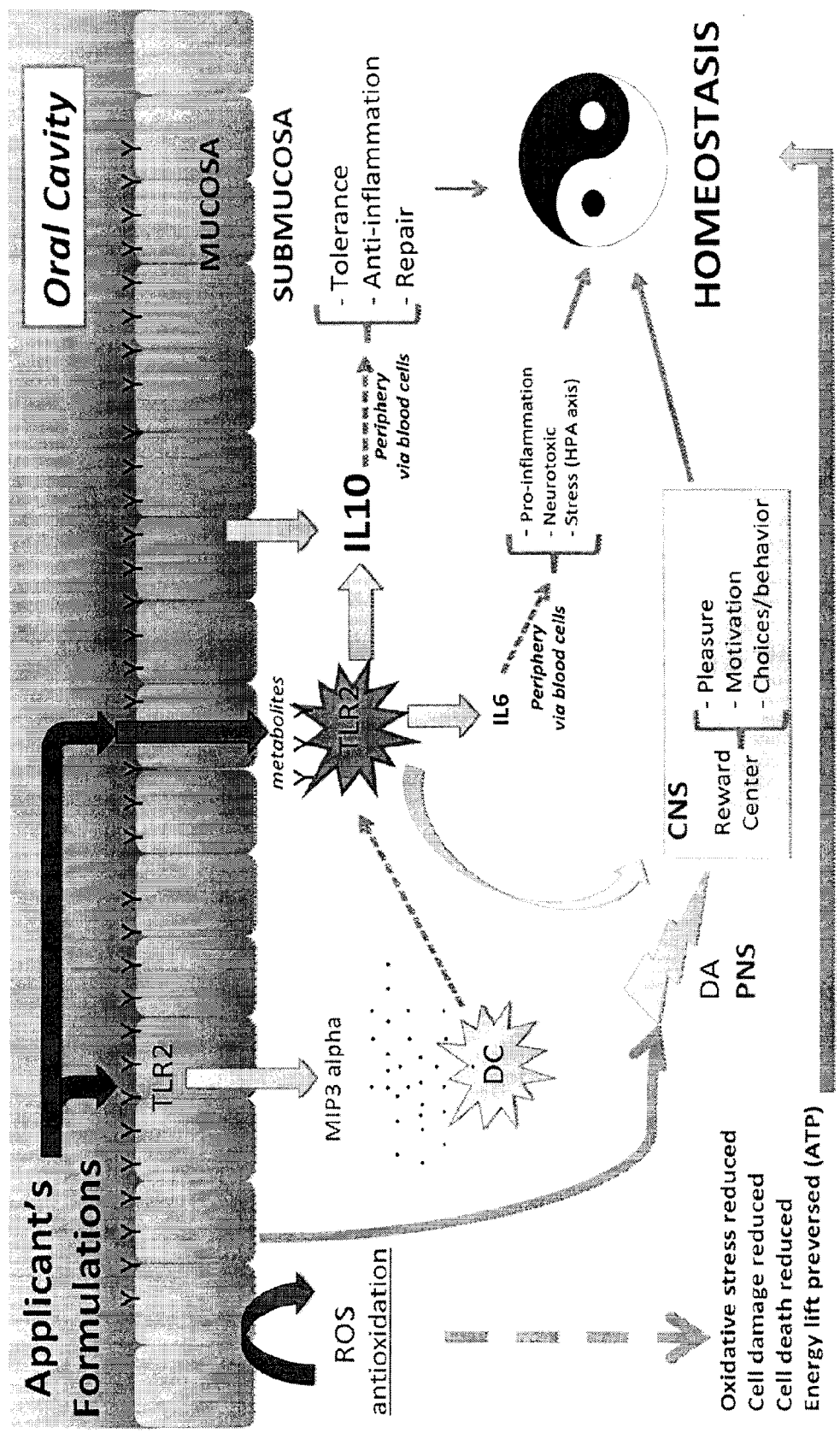
FIG. 43 is a schematic representation of the mechanism of action of Applicant's invention. Formulations developed by Applicant, delivered at oral mucosal surfaces, can regulate mucosal and sub mucosal responses to promote homeostasis.

FIG. 43 is a schematic representation of Applicant's invention. Formulations developed by Applicant, delivered at oral mucosal surfaces, can regulate mucosal and submucosal responses to promote homeostasis. The responses modulated by formulations developed by Applicant include oxidative stress, TLR2 activation, mitochondrial activity, ATP and inflammatory responses.

Figure 44:
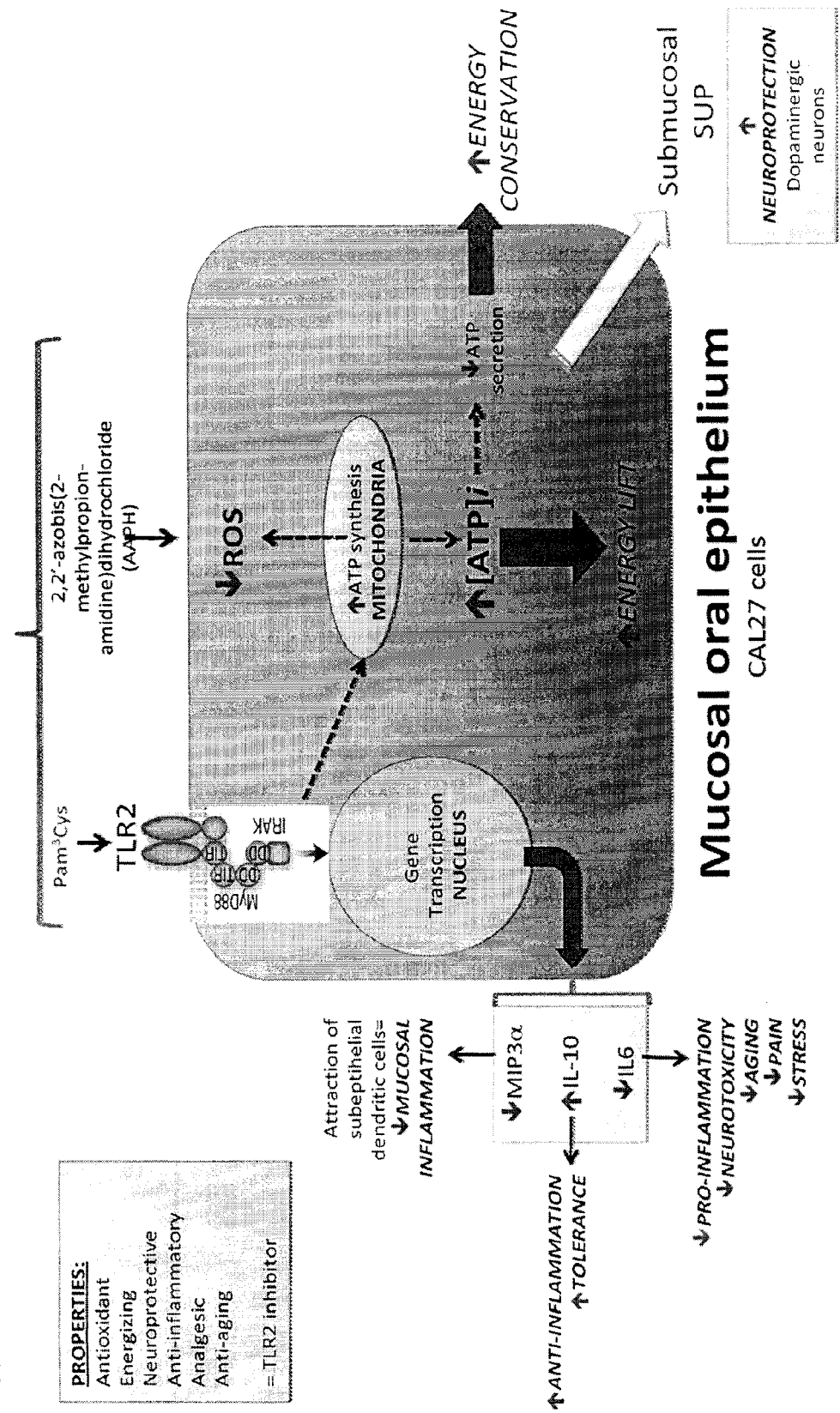
FIG. 44 is a schematic representation of results obtained with formulation 1.

FIG. 44 is a schematic representation of results obtained with formulation 1. In summary, formulation 1 has the following properties: antioxidant, energizing, neuroprotective, anti-inflammatory, pro-tolerant (via IL-10) and a possible analgesics and anti-aging formulation.

FIG. 45 is a table that summarizes results obtained for all formulations tested.

The ORAC measures for different natural sweeteners shown in FIG. 46 were compared to the sum of the ORAC value of maple syrup added that of individual ingredients (SUM of SE+ingredient). Maple syrup combined with stevia-derived molecules (whole stevia extract or stevioside or Rebaudiside A) act in synergy to potentiate the antioxidant potential. Combination of maple syrup with aspartame and sucralose does not create this synergy. This result suggest that diet products could be formulated maple and stevia to obtain additional antioxidant activity.

CONCLUSIONS

Mucosal TLR2 regulates oxidative and energetic responses and adaptogenic formulations of the present invention act via this pathway to promote homeostasis.

Formulations developed using the adaptogen concept of herbalism according to the present invention promote homeostasis. This finding provides scientific evidence to support the concept of adaptogens.

Ingredients of adaptogenic formulations according to the present invention act in synergy to promote homeostasis. Synergy potentiates the antioxidant potential, mitochondrial activity and neuroprotective property of formulations.

Formulation 1 of the present invention developed by Applicant prevents increase of salivary dopamine levels in humans, while inducing an energy lift in mucosal cells, suggesting that the formulation can energize without causing addiction.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All patents, patent applications and publications mentioned in this specification are herein incorporated by reference to the same extent as if each independent patent, patent application, or publication was specifically and individually indicated to be incorporated by reference.

REFERENCES

Abreu M L. 2010. Toll-like receptor signaling in the intestinal epithelium: how bacterial recognition shapes intestinal function. Nat Rev Immunol 10(2):131-44.

Backhed, F., R. E. Ley, J. L. Sonnenburg, D. A. Peterson, and J. I. Gordon. 2005. Host-bacterial mutualism in the human intestine. Science 307:1915-1920.

Byun et al. TLR4 signaling inhibitory pathway induced by green tea polyphenol epigallocatechin-3-gallate through 67-kDa laminin receptor. J. Immunol. 2010 185(1):33-45.

Cario E, Gerken G, Podolsky D K. 2007. Toll-like receptor 2 controls mucosal inflammation by regulating epithelial barrier function. 132(4):1359-74.

Cario E. 2008. Barrier-protective function of intestinal epithelial Toll-like receptor 2. Mucosal Immunol 1 Suppl 1:S62-6.

Cario E. 2010. Toll-like receptors in inflammatory bowel diseases: a decade later. Inflamm Bowel Dis 16(9):1583-97.

Chabot, S., J. S. Wagner, S. Farrant, and M. R. Neutra. 2006. Toll-like receptors regulate the gatekeeping functions of the intestinal follicle-associated epithelium. J Immunol 176:4275-4283.

Cook, D. N., D. M. Prosser, R. Forster, J. Zhang, N. A. Kuklin, S. J. Abbondanzo, X. D. Niu, S. C. Chen, D. J. Manfra, M. T. Wiekowski, L. M. Sullivan, S. R. Smith, H. B. Greenberg, S. K. Narula, M. Lipp, and S. A. Lira. 2000. CCR6 mediates dendritic cell localization, lymphocyte homeostasis, and immune responses in mucosal tissue. Immunity 12:495-503.

Crimi, E., V. Sica, S. Williams-Ignarro, H. Zhang, A. S. Slutsky, L. J. Ignarro. C. Napoli. 2006. The role of oxidative stress in adult critical care. Free Radical Biology & Medicine 40: 398-406.

D'Autréaux, B., and Toledano, M. B. 2007. ROS as signaling molecules: mechanisms that generate specificity in ROS homeostasis. Nature Reviews. Mol Cell Bio 8: 813-824.

Datla, P., M. D. Kalluro, K. Basha, R. Kshirsagar, Y. Kanekar, S. Upadhyay, S. Singh, V. Rajagopal. 2010. 9,10-dihydro-2,5-dimethoxyphenanthrene-1,7-diol, from *Eulophia ochreata*, inhibits inflammatory signalling mediated by Toll-like receptors. Br J Pharmacol 160(5): 1158-1170.

Didierlaurent, A., J.-C. Sirard, and J.-P. Kraehenbuhl. 2002. How the gut senses its content. Cell. Microbiol. 4:61-72.

Finkel, T., and N. J. Holbrook. 2000. Oxidants, oxidative stress and the biology of ageing. Nature. 408: 239-247.

Fu et al. Dioscorin isolated from *Dioscorea alata* activates TLR4-signaling pathways and induces cytokine expression in macrophages Biochemical and biophysical research communications. 2006 339(1):137-144.

Heim, K E, Tagliaferro, A R and Bobilya, D J. 2002. Flavonoid antioxidants: chemistry, metabolism and structure-activity relationships. The journal of nutritional biochemistry, Vol 13, Issue 10: 572-584.

Iwasaki, A., and B. L. Kelsall. 2000. Localization of distinct Peyer's patch dendritic cell subsets and their recruitment by chemokines macrophage inflammatory protein (MIP)-3, MIP-3, and secondary lymphoid organ chemokine. J Exp Med 191:1381-1394.

Levites, Y, Amit, T, Mandel S, Youdim M B. 2003. Neuroprotection and neurorescue against Abeta toxicity and PKC-dependent release of nonamyloidogenic soluble precursor protein by green tea polyphenol (–)-epigallocatechin-3-gallate. FASEB J. 2003 17(8):952-4

Macheix, J-J, Fleuriet, A, and Billot, J. 1990. Fruit phenolics. Florida: CRC Press, Inc. Using Integrative Management. Alternative Medicine Review, Vol 10, Number 4: 268-293. Mazzio E A, Reams R R, Soliman K F. 2004. The role of oxidative stress, impaired glycolysis and mitochondrial respiratory redox failure in the cytotoxic effects of 6-hydroxydopamine in vitro. Brain Res. 1004 (1-2):29-44.

Mossman, 1983, J Immunol Methods, 65:55-63

Ortega-Cava, C. F., S. Ishihara, M. A. Rumi, K. Kawashima, N. Ishimura, H. Kazumori, J. Udagawa, Y. Kadowaki, and Y. Kinoshita. 2003. Strategic compartmentalization of Toll-like receptor 4 in the mouse gut. J. Immunol. 170: 3977-3985.

Prior, R. L., Hoang, H., Gu, L., Wu, X., Bacchiocca, M., Howard, L., Hampsch-Woodill M, Huang, D., Ou, B., Jacob, R. 2003. Assays for hydrophilic and lipophilic antioxidant capacity (oxygen radical absorbance capacity (ORACFL) of plasma and other biological and food samples. J. Agric. Food Chem. 51: 3273-3279.

Rakoff-Nahoum, S., J. Paglino, F. Eslami-Varzaneh, S. Edberg, and R. Medzhitov. 2004. Recognition of commensal microflora by toll-like receptors is required for intestinal homeostasis. Cell 118:229-241.

Singh M, Arsenault M, Sanderson T, Murthy V and C Ranassany. 2008. Challenges for research on polyphenols from foods and Alzheimer's disease: bioavailability, metabolism and cellular and molecular mechanism. J. Agr. Food Chem 56: 4855-4873.

Thériault, M, Caillet, S, Kermasha, S. and Lacroix, M. 2005. Antioxidant, antiradical and antimutagenic activities of phenolic compounds present in maple products. Food Chemistry, Vol 98, Issue 3: 490-501.

Yao, Y and Vieira, A. 2007. Protective activities of *Vaccinium* antioxidants with potential relevance to mitochondrial dysfunction and neurotoxicity. Neuro Toxicology, Vol 28, Issue 1: 93-100.

Wang, H., M. Zhou, J. Brand, L. Huang. 2009. Inflammation and taste disorders: mechanisms in taste buds. Ann N Y Acad Sci 1170: 596-603.

West A. P., I. E. Brodsky, C. Rahner, D. K. Woo, H. Erdjument-Bromage, P. Tempst, M. C. Walsh, Y. Choi, G. S. Shadel, S. Ghosh. 2011. TLR signaling augments macrophage bactericidal activity through mitochondrial ROS. Nature. 472: 476-480.

West. A. P., G. S. Shadel, S. Ghosh. 2011. Mitochondria in innate immune responses. Nature Reviews Immunology 11: 389-40.

Wlasiuk G., M. W. Nachman. 2010. Adaptation and constraint at Toll-like receptors in primates. Mol Biol Evol 27(9): 2172-2186.

Zafra-Stone S, Yasmin T, Bagchi M, Chatterjee A, Vinson J A, Bagchi D. 2007. Berry anthocyanins as novel antioxidants in human health and disease prevention. Mol Nutr Food Res 51(6):675-83.

The invention claimed is:

1. A method for increasing energy levels in a mammalian cell, comprising administering an intracellular increasing ATP-production-amount and/or ATP-conserving amount of a composition consisting essentially of:
- an antioxidant polyphenol-containing herbal extract of Raspberry leaf and Yarrow; in a concentration corresponding to at least 2000 ORAC value;
- an antioxidant polyphenol-containing fruit extract of blueberry and cranberry; in a concentration corresponding to at least 200 ORAC value;
- an antioxidant sweetener in a concentration corresponding to at least 20 ORAC value, wherein the antioxidant sweetener is a maple product; and
- optionally, a flavor or aroma;

wherein composition has a total polyphenol content higher than 100 mg to achieve increased intracellular ATP-production and/or ATP-conservation, thus increasing energy levels in a mammalian cell.

2. The method of claim 1, wherein said composition is in a form of a liquid, solid, or semi-solid.

3. The method of claim 2, wherein the composition is in a solid form selected from a tablet, a capsule, a caplet, a bar, and a powder.

4. The method of claim 3, wherein said composition is in the form of a powder dissolvable in water to form a drink for a human.

5. The method of of claim 2, wherein said composition is in a semi-solid form selected from pudding and yogurt.

6. The method of claim 2, wherein said composition is a liquid in the form of a drink for human consumption.

7. The method according to claim 1, wherein the maple product is maple syrup.

* * * * *